Figure 1A:
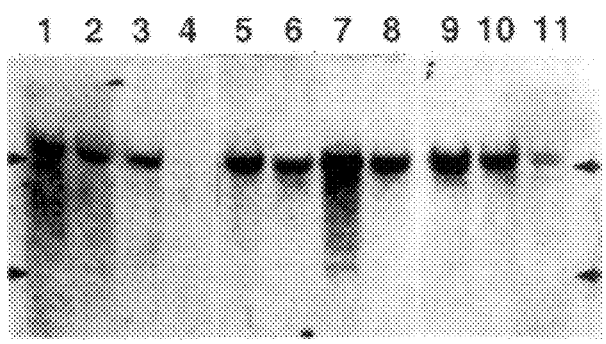

United States Patent [19]
Wilks et al.

[11] Patent Number: 5,910,426
[45] Date of Patent: Jun. 8, 1999

[54] PROTEIN TYROSINE KINASE

[75] Inventors: Andrew Frederick Wilks, Doneaster East, Australia; Andrew Ziemiecki, Berne, United Kingdom; Ailsa Harpur, Mooroolbark, Australia

[73] Assignee: Ludwig Institute for Cancer Research, New York, N.Y.

[21] Appl. No.: 09/066,208

[22] Filed: Apr. 24, 1998

Related U.S. Application Data

[62] Division of application No. 08/805,445, Feb. 25, 1997, Pat. No. 5,821,069, which is a division of application No. 08/446,038, May 19, 1995, Pat. No. 5,658,791, which is a division of application No. 08/064,067, filed as application No. PCT/US91/08889, Nov. 26, 1991, Pat. No. 5,852,184.

[30] Foreign Application Priority Data

Nov. 28, 1990 [AU] Australia .............. PK3594/90

[51] Int. Cl.⁶ .............. C12P 21/06; C07K 1/00
[52] U.S. Cl. .............. 435/68.1; 530/402
[58] Field of Search .............. 435/68.1; 530/402

*Primary Examiner*—Karen Cochrane Carlson
*Assistant Examiner*—Maryam Monshipouri
*Attorney, Agent, or Firm*—Fulbright and Jaworski, LLP

[57] ABSTRACT

The present invention is directed to a novel protein tyrosine kinase comprising a polypeptide having multiple protein kinase catalytic domains and, more particularly, two kinase catalytic domains and to genetic sequences encoding same. Two such kinases are described and designated JAK1 and JAK2.

7 Claims, 34 Drawing Sheets

FIG. 2A

```
TGGCCGCCTA GCGAGCTGCC GGTCGACCCC AGCCAGCCCC AGCCAGCCGA GCGACGGGCG CTGCCTGGCC 60

CAGGGCACAC GGAAGTGCGC TTCTCTGAAG TAGCTTTGGA AAGTAGAGAA GAAAATCCAG 120

TTTGCTTCTT GGAGAACACT GGACAGCTGA ATAA ATG CAG TAT CTA AAT
169                                    Met Gln Tyr Leu Asn
                                                    -10

ATA AAA GAG GAC TGC AAT GCC ATG GCT TTC TGT GCT AAA ATG AGG    214
Ile Lys Glu Asp Cys Asn Ala Met Ala Phe Cys Ala Lys Met Arg
         -5                  +1                   5

AGC TCC AAG AAG ACT GAG GTG AAC CTG GAG GCC CCT GAG CCA GGG    259
Ser Ser Lys Lys Thr Glu Val Asn Leu Glu Ala Pro Glu Pro Gly
         10                  15                  20

GTG GAA GTG ATC TTC TAT CTG TCG GAC AGG GAG CCC CTC CGG CTG    304
Val Glu Val Ile Phe Tyr Leu Ser Asp Arg Glu Pro Leu Arg Leu
         25                  30                  35

GGC AGT GGA GAG TAC ACA GCA GAG GAA CTG TGC ATC AGG GCT GCA    349
Gly Ser Gly Glu Tyr Thr Ala Glu Glu Leu Cys Ile Arg Ala Ala
         40                  45                  50
```

FIG. 2B

```
CAG GCA TGC CGT ATC TCT CCT CTT TGT CAC AAC CTC TTT GCC CTG    394
Gln Ala Cys Arg Ile Ser Pro Leu Cys His Asn Leu Phe Ala Leu
 55                      60                  65

TAT GAC GAG AAC ACC AAG ACC AAG CTC TGG TAT GCT CCA AAT CGC ACC ATC    439
Tyr Asp Glu Asn Thr Lys Thr Lys Leu Trp Tyr Ala Pro Asn Arg Thr Ile
         70                  75                  80

ACC GTT GAT GAC AAG ATG TCC CTC CGG CTC CAC TAC CGG ATG AGG    484
Thr Val Asp Asp Lys Met Ser Leu Arg Leu His Tyr Arg Met Arg
             85                  90                  95

TTC TAT TTC ACC AAT TGG CAT GGA ACC AAC GAC AAT GAG CAG TCA    529
Phe Tyr Phe Thr Asn Trp His Gly Thr Asn Asp Asn Glu Gln Ser
         100                 105                 110

GTG TGG CGT CAT TCT CCA AAG AAG CAG AAA AAT GGC TAC GAG AAA    574
Val Trp Arg His Ser Pro Lys Lys Gln Lys Asn Gly Tyr Glu Lys
         115                 120                 125

AAA AAG ATT CCA GAT GCA ACC CCT CTC CTT GAT GCC AGC TCA CTG    619
Lys Lys Ile Pro Asp Ala Thr Pro Leu Leu Asp Ala Ser Ser Leu
         130                 135                 140

GAG TAT CTG TTT GCT CAG GGA CAG TAT GAT TTG GTG AAA TGC CTG    664
Glu Tyr Leu Phe Ala Gln Gly Gln Tyr Asp Leu Val Lys Cys Leu
         145                 150                 155
```

FIG. 2C

```
GCT CCT ATT CGA GAC CCC AAG ACC GAG CAG GAT GGA CAT GAT ATT    709
Ala Pro Ile Arg Asp Pro Lys Thr Glu Gln Asp Gly His Asp Ile
160                 165                 170

GAG TGT CTA GGG ATG GCT GTC CTG GCC ATC TCA CAC TAT            754
Glu Cys Leu Gly Met Ala Val Leu Ala Ile Ser His Tyr
    175                 180                 185

GCC ATG AAG AAG ATG CAG TTG CCA GAA CTG CCC AAG GAC ATC        799
Ala Met Lys Lys Met Gln Leu Pro Glu Leu Pro Lys Asp Ile
190                 195                 200

AGC TAC AAG CGA TAT ATT CCA GAA ACA TTG AAT AAG TCC ATC AGA    844
Ser Tyr Lys Arg Tyr Ile Pro Glu Thr Leu Asn Lys Ser Ile Arg
    205                 210                 215

CAG AGG AAC CTT CTC ACC AGG ATG CGG ATA AAT GTT TTC AAG        889
Gln Arg Asn Leu Leu Thr Arg Met Arg Ile Asn Val Phe Lys
220                 225                 230

GAT TTC CTA AAG GAA TTT AAC AAG ACC ATT TGT GAC AGC AGC        934
Asp Phe Leu Lys Glu Phe Asn Lys Thr Ile Cys Asp Ser Ser
    235                 240                 245
```

FIG. 2D

```
GTG TCC ACG CAT GAC CTG AAG GTG AAA TAC TTG GCT ACC TTG GAA      979
Val Ser Thr His Asp Leu Lys Val Lys Tyr Leu Ala Thr Leu Glu
250                 255                 260

ACT TTG ACA AAA CAT TAC GGT GCT GAA ATA TTT GAG ACT TCC ATG     1024
Thr Leu Thr Lys His Tyr Gly Ala Glu Ile Phe Glu Thr Ser Met
    265                 270                 275

TTA CTG ATT TCA TCA GAA AAT GAG ATG AAT TGG TTT CAT TCG AAT     1069
Leu Leu Ile Ser Ser Glu Asn Glu Met Asn Trp Phe His Ser Asn
        280                 285                 290

GAC GGT GGA AAC GTT CTC TAC TAC GAA GTG ATG GTG ACT GGG AAT     1114
Asp Gly Gly Asn Val Leu Tyr Tyr Glu Val Met Val Thr Gly Asn
            295                 300                 305

CTT GGA ATC CAG TGG AGG CAT AAA CCA AAT GTT TCT GTT GAA         1159
Leu Gly Ile Gln Trp Arg His Lys Pro Asn Val Ser Val Glu
310                 315                 320

AAG GAA AAA AAT AAA CTG AAA CGG AAA AAA CTG GAA AAT AAA GAC     1204
Lys Glu Lys Asn Lys Leu Lys Arg Lys Lys Leu Glu Asn Lys Asp
    325                 330                 335

AAG AAG GAT GAG GAG AAA AAC AAG ATC CGG GAA GAG TGG AAC AAT     1249
Lys Lys Asp Glu Glu Lys Asn Lys Ile Arg Glu Glu Trp Asn Asn
        340                 345                 350
```

FIG. 2E

```
TTT TCA TTC TTC CCT GAA ATC ACT CAC ATT GTA ATA AAG GAG TCT    1294
Phe Ser Phe Phe Pro Glu Ile Thr His Ile Val Ile Lys Glu Ser
355                 360                 365

GTG GTC AGC ATT AAC AAG CAG GAC AAC AAG AAA ATG GAA CTG AAG    1339
Val Val Ser Ile Asn Lys Gln Asp Asn Lys Lys Met Glu Leu Lys
370                 375                 380

CTC TCT TCC CAC GAG GAG GCC TTG TCC TTT GTG TCC CTG GTA GAT    1384
Leu Ser Ser His Glu Glu Ala Leu Ser Phe Val Ser Leu Val Asp
385                 390                 395

GGC TAC TTC CGG CTC ACA GCA GAT GCC CAT TAC CTC TGC ACC        1429
Gly Tyr Phe Arg Leu Thr Ala Asp Ala His Tyr Leu Cys Thr
400                 405                 410

GAC GTG GCC CCC CCG TTG ATC GTC CAC AAC ATA CAG AAT GGC TGT    1474
Asp Val Ala Pro Pro Leu Ile Val His Asn Ile Gln Asn Gly Cys
415                 420                 425

CAT GGT CCA ATC TGT ACA GAA TAC GCC ATC AAT AAA TTG CGG CAA    1519
His Gly Pro Ile Cys Thr Glu Tyr Ala Ile Asn Lys Leu Arg Gln
430                 435                 440
```

FIG. 2F

```
GAA GGA AGC GAG GAG GGG ATG TAC GTG CTG AGG TGG AGC TGC ACC   1564
Glu Gly Ser Glu Glu Gly Met Tyr Val Leu Arg Trp Ser Cys Thr
445                 450                 455

GAC TTT GAC AAC ATC CTC ATG ACC GTC ACC TGC TTT GAG AAG TCT   1609
Asp Phe Asp Asn Ile Leu Met Thr Val Thr Cys Phe Glu Lys Ser
        460                 465                 470

GAG CAG GTG CAG GGT GCC CAG AAG CAG TTC AAG AAC TTT CAG ATC   1654
Glu Gln Val Gln Gly Ala Gln Lys Gln Phe Lys Asn Phe Gln Ile
475                 480                 485

GAG GTG CAG AAG GGC CGC TAC AGT CTG CAC GGT TCG GAC CGC AGC   1699
Glu Val Gln Lys Gly Arg Tyr Ser Leu His Gly Ser Asp Arg Ser
490                 495                 500

TTC CCC AGC TTG GGA GAC CTC ATG AGC CAC CTC AAG AAG CAG ATC   1744
Phe Pro Ser Leu Gly Asp Leu Met Ser His Leu Lys Lys Gln Ile
505                 510                 515

CTG CGC ACG GAT AAC ATC AGC TTC ATG CTA AAA CGC TGC TGC CAG   1789
Leu Arg Thr Asp Asn Ile Ser Phe Met Leu Lys Arg Cys Cys Gln
520                 525                 530
```

FIG. 2G

```
CCC AAG CCC CGA GAA ATC TCC AAC CTG CTG GTG GCT ACT AAG AAA    1834
Pro Lys Pro Arg Glu Ile Ser Asn Leu Leu Val Ala Thr Lys Lys
535                     540                 545

GCC CAG GAG TGG CAG CCC TAC GTC TAC CCC ATG AGC CAG CTG AGT TTC    1879
Ala Gln Glu Trp Gln Pro Tyr Val Tyr Pro Met Ser Gln Leu Ser Phe
        550                 555                 560

GAT CGG ATC CTC AAG AAG AAG GAT CTG GTG CAG GGC GAG CAC CTT GGG    1924
Asp Arg Ile Leu Lys Lys Lys Asp Leu Val Gln Gly Glu His Leu Gly
565                 570                 575
    I_a

AGA GGC ACG AGA ACA CAC ATC TAT TCT GGG ACC CTG ATG GAT TAC    1969
Arg Gly Thr Arg Thr His Ile Tyr Ser Gly Thr Leu Met Asp Tyr
580                 585                 590

AAG GAT GAC GAA GGA ACT TCT GAA GAG AAG AAG ATA AAA GTG ATC    2014
Lys Asp Asp Glu Gly Thr Ser Glu Glu Lys Lys Ile Lys Val Ile
595                 600                 605
II_a

CTC AAA GTC TTA GAC CCC AGC CAC AGG GAT ATT TCC CTG GCC TTC    2059
Leu Lys Val Leu Asp Pro Ser His Arg Asp Ile Ser Leu Ala Phe
605                 615                 620
```

FIG. 2H

```
     IIIa                                                    IVa
TTC GAG GCA GCC AGC ATG AGA CAG GTC TCC CAC AAA CAC ATC      2104
Phe Glu Ala Ala Ser Met Arg Gln Val Ser His Lys His Ile
    625                 630                 635

GTG TAC CTC TAT GGC GTC TGT GTC CGC GAC GTG GAG AAT ATC ATG  2149
Val Tyr Leu Tyr Gly Val Cys Val Arg Asp Val Glu Asn Ile Met
    640                 645                 650
                         Va
GTG GAA GAG TTT GTG GAA GGG GGT CCT CTG GAT CTC TTC ATG CAC  2194
Val Glu Glu Phe Val Glu Gly Gly Pro Leu Asp Leu Phe Met His
    655                 660                 665

CGG AAA AGT GAT GTC CTT ACC ACA CCA TGG AAA TTC AAA GTT GCC  2239
Arg Lys Ser Asp Val Leu Thr Thr Pro Trp Lys Phe Lys Val Ala
    670                 675                 680

AAA CAG CTG GCC AGT GCC CTG AGC TAC TTG GAG GAT AAA GAC CTG  2284
Lys Gln Leu Ala Ser Ala Leu Ser Tyr Leu Glu Asp Lys Asp Leu
    685                 690                 695
     VIa
GTC CAT GGA AAT GTG TGT ACT AAA AAC CTC CTC CTG GCC CGT GAG  2329
Val His Gly Asn Val Cys Thr Lys Asn Leu Leu Leu Ala Arg Glu
    700                 705                 710
```

FIG. 21

```
                                                                                          VII_a
GGA ATC GAC AGT GAG TGT GGC CCA TTC ATC AAG CTC AGT GAC CCC     2374
Gly Ile Asp Ser Glu Cys Gly Pro Phe Ile Lys Leu Ser Asp Pro
715                             720                 725

GGC ATC CCC ATT ACG GTG CTG TCT AGG CAA GAA TGC ATT GAA CGA     2419
Gly Ile Pro Ile Thr Val Leu Ser Arg Gln Glu Cys Ile Glu Arg
        730                             735                 740
    VIII_a
ATC CCA TGG ATT GCT CCT GAG TGT GTT GAG GAC TCC AAG AAC CTG     2464
Ile Pro Trp Ile Ala Pro Glu Cys Val Glu Asp Ser Lys Asn Leu
            745                             750                 755
                        IX_a
AGT GTG GCT GCT GAC AAG TGG AGC TTT GGA ACC ACG CTC TGG GAA     2509
Ser Val Ala Ala Asp Lys Trp Ser Phe Gly Thr Thr Leu Trp Glu
                760                             765                 770

ATC TGC TAC AAT GGC GAG ATC CCC TTG AAA GAC AAG ACG CTG ATT     2554
Ile Cys Tyr Asn Gly Glu Ile Pro Leu Lys Asp Lys Thr Leu Ile
                    775                             780                 785
                                                            X_a
GAG AAA GAG AGA TTC TAT GAA AGC CGG TGC CGG TGC CCA GTG ACA CCA     2599
Glu Lys Glu Arg Phe Tyr Glu Ser Arg Cys Arg Cys Pro Val Thr Pro
                        790                             795                 800
                                                                    XI_a
TCA TGT AAG GAG CTG GCT GAC CTC ATG ACC CGC TGC TGG ATG AAC TAT     2644
Ser Cys Lys Glu Leu Ala Asp Leu Met Thr Arg Cys Trp Met Asn Tyr
                            805                             810                 815
```

FIG. 2J

```
GAC CCC AAT CAG AGG CCT TTC CGA GCC ATC ATG AGA GAC ATT    2689
Asp Pro Asn Gln Arg Pro Phe Arg Ala Ile Met Arg Asp Ile
            820             825             830

AAT AAG CTT GAA GAG CAG CAG AAT CCA GAT ATT GTT TCC AGA AAA AAA    2734
Asn Lys Leu Glu Glu Gln Gln Asn Pro Asp Ile Val Ser Arg Lys Lys
            835             840             845

AAC CAG CCA ACT GAA GTG GAC CCC ACA CAT TTT GAG AAG CGC TTC    2779
Asn Gln Pro Thr Glu Val Asp Pro Thr His Phe Glu Lys Arg Phe
            850             855             860
                                     I
CTA AAG AGG ATC CGT GAC TTG GGA GAG GGC CAC TTT GGG AAG GTT    2824
Leu Lys Arg Ile Arg Asp Leu Gly Glu Gly His Phe Gly Lys Val
            865             870             875

GAG CTC TGC AGG TAT GAC CCC GAA GAC AAT ACA GGG GAG CAG GTG    2869
Glu Leu Cys Arg Tyr Asp Pro Glu Asp Asn Thr Gly Glu Gln Val
        880             885             890
    II

GCT GTT AAA TCT CTG AAG CCT GAG AGT GGA GGT AAC CAC ATA GCT    2914
Ala Val Lys Ser Leu Lys Pro Glu Ser Gly Gly Asn His Ile Ala
            895             900             905
        III

GAT CTG AAA AAG GAA ATC TTA AGG AAC CTC TAT CAT GAG    2959
Asp Leu Lys Lys Glu Ile Leu Arg Asn Leu Tyr His Glu
            910             915             920
```

FIG. 2K

```
      IV
AAC ATT GTG AAG TAC AAA GGA ATC TGC ACA GAA GAC GGA GGA AAT      3004
Asn Ile Val Lys Tyr Lys Gly Ile Cys Thr Glu Asp Gly Gly Asn
        925                 930                 935
                                                 V
GGT ATT AAG CTC ATC ATG GAA TTT CTG CCT TCG GGA AGC CTT AAG      3049
Gly Ile Lys Leu Ile Met Glu Phe Leu Pro Ser Gly Ser Leu Lys
        940                 945                 950

GAA TAT CTT CCA AAG AAT AAA ATA AAC CTC AAA CAG CAG             3094
Glu Tyr Leu Pro Lys Asn Lys Ile Asn Leu Lys Gln Gln
        955                 960                 965

CTA AAA TAT GCC GTT CAG ATT TGT AAG GGG ATG GAC TAT TTG GGT      3139
Leu Lys Tyr Ala Val Gln Ile Cys Lys Gly Met Asp Tyr Leu Gly
        970                 975                 980
                            VI
TCT CGG CAA TAC GTT CAC CGG GAC TTG GCA AGA GCA AGA AAT GTC CTT  3184
Ser Arg Gln Tyr Val His Arg Asp Leu Ala Arg Ala Arg Asn Val Leu
        985                 990                 995
                                    VII
GTT GAG AGT GAA CAC CAA GTG AAA ATT GGA GAC TTC GGT TTA ACC      3229
Val Glu Ser Glu His Gln Val Lys Ile Gly Asp Phe Gly Leu Thr
        1000                1005                1010

AAA GCA ATT GAA ACC GAT AAG GAG TAT TAC ACC GTC AAG GAT GAC      3279
Lys Ala Ile Glu Thr Asp Lys Glu Tyr Tyr Thr Val Lys Asp Asp
        1015                1020                1025
```

FIG. 2L

```
       VIII
CGG GAC AGC CCT GTG TTT TGG TAT GCT CCA GAA TGT TTA ATG CAA
Arg Asp Ser Pro Val Phe Trp Tyr Ala Pro Glu Cys Leu Met Gln    3319
         1030                    1035                 1040
                                                  IX
TCT AAA TTT TAT ATT GCC TCT GAC GTC TGG TCT TTT GGA GTC ACT
Ser Lys Phe Tyr Ile Ala Ser Asp Val Trp Ser Phe Gly Val Thr    3364
         1045                    1050                 1055

CTG CAT GAG CTG CTG ACT TAC TGT GAT TCA GAT TCT AGT CCC ATG
Leu His Glu Leu Leu Thr Tyr Cys Asp Ser Asp Ser Ser Pro Met    3409
         1060                    1065                 1070

GCT TTG TTC CTG AAA ATG ATA GGC CCA ACC CAT GGC CAG ATG ACA
Ala Leu Phe Leu Lys Met Ile Gly Pro Thr His Gly Gln Met Thr    3454
         1075                    1080                 1085
                                                  X
GTC ACA AGA CTT GTG AAT ACG TTA AAA GAA GGA AAA CGC CTG CCG
Val Thr Arg Leu Val Asn Thr Leu Lys Glu Gly Lys Arg Leu Pro    3499
         1090                    1095                 1100

TGC CCA CCT AAC TGT CCA GAT GAG GTT TAT CAG CTT ATG AGA AAA
Cys Pro Pro Asn Cys Pro Asp Glu Val Tyr Gln Leu Met Arg Lys    3544
         1105                    1110                 1115
```

FIG. 2M

```
                XI
TGC TGG GAA TTC CAA CCA TCC AAT CGG ACA AGC TTT CAG AAC CTT   3589
Cys Trp Glu Phe Gln Pro Ser Asn Arg Thr Ser Phe Gln Asn Leu
    1120                    1125                    1130

ATT GAA GGA TTT GAA GCA CTT TTA AAA TAAGAAGCAT GAATAACATT
3636
Ile Glu Gly Phe Glu Ala Leu Leu Lys
    1135                    1140

TAAATTCCAC AGATTATCAA GTCCTTCTCC TGCAACAAAT GCCCAAGTCA TTTTTTAAAA 3696
ATTTCTAATG AAAGAAGTTT GTGTTCTGTC CAAAAAGTCA CTGAACTCAT ACTTCAGTAC 3756
ATATACATGT ATAAGGCACA CTGTAGTGCT ACATAATGAC AAGGACTTCC TCTTTAAATT 3816
TGCACCAGTA ACTTAGTGAC ACATAATGAC AACCAAAATA TTTGAAAGCA CTTAAGCACT 3876
CCTCCTTGTG GAAAGAATAT ACCACCATTT CATCTGGCTA GTTCACCATC ACAACTGCAT 3936
TACCAAAAGG GGATTTTTGA AAACGAGGAG TTGACCAAAA TAATATCTGA AGATGATTGC 3996
TTTTCCCTGC TGCCAGCTGA CTGAAATGTT TTCCTGGCAC ATTAATCATA GATAAAGAAG 4056
ATTGATGGAC TTAGCCCTCA AACAGTATCT ATACAGTACT AGACCATGCA TTCTTAAAAT 4116
ATTAGATACC AGGTAGTATA TATTGTTTCT GTACAAAAAT GACTGTATTC TCTCACCAGT 4176
AGGACTTAAA CTTTGTTTCT CCAGTGGCTT AGCTCCTGTT CCTTTGGGTG ATCACTAG 4234
```

FIG. 3A

```
              I                                          II                         III
Domain 1  HLGRGTRTHIYSGTLMDYKDDEGTSEEKKIKVILKVLDPS...HRDISLAGGEAASM    -60aa-
Domain 2  DLGEGHFGKVELCRT.DPEDNTGE.......QVAVKSLKPES.GGNHIADLKKEIEIL    -63aa-
CDC2-H    KIGEGTYGVVYKGRH......KYYG......QVVAMKKIRLESEEGVPSTAIREISLL    -55aa- IV                                       V
                                                                                           IX
Domain 1  SYLEDKDLVHGNVCTKNLLLAREGIDSECGPFIKLSDPGIPITVLS......RQECIERIPW.IAPECVEDSKNLSVAADKWSFGTTLWEIC  -20aa-
Domain 2  DYLGSRQYVHRDLAARNVLVESE.........VKIGDFGLTKAIETDKEYTVKDDRDSPCFW.YAPECLMQSKF.YIASDVWSFGVTLHELL  -38aa-
CDC2-H    VFCHSRRVLHRDLKPQNLLIDDKG......TIKLADGGLARAFGIPIRVYTHE...VVT.LMYRSPEVLLGSARYSTPVDIWSIGTIFAELA  -50aa- XI
Domain 1  SRCRPVTPSCKELADLMTRCMNYDPNQRPF
Domain 2  LPCPPNCPDEVYQ..LMRKCWEFQPSNRTS
CDC2-H    LASHHVKNLDENGLDLLSKMLIYDPAKRIS
```

FIG. 5

```
              Ia                                    IIa         IIIa  70
VFHKIRNEDL IFNESLGQGT FTKIFKGVRR EVGDYGQLHE TE...VLLKV LDKAHRNYSE SFFEAASMMS   MJAK2
 *$*    ** $  * ** ** * *$ *     $  *    *    *$*** **  **  *   ********
SFDRILKKDL VQGEHLGRGT RTHIYSGTLM DYKDDEGTSE EKKIKVILKV LDPSHRDISL AFFEAASMMR   HJAK1

IVa                Va                                                140
QLSHKHLVLN YGVCVCGEEN ILVQEFVKFG SLDTYLKKNK NSINILWKLG VAKQLAWAMH FLEEKSLIHG   MJAK2
 *$****$*  *****    ** * * ***  *   ** $  $    $   ** ****** *  $**$* *$**
QVSHKHIVYL YGVCVRDVEN IMVEEFVEGG PLDLFMHRKS DVLTTPWKFK VAKQLASALS YLEDKDLVHG   HJAK1

VIa                VIIa                          VIIIa              210
NVCAKNILLI REEDRRTGNP PFIKLSDPGI SITVLPKDIS SCCFQVLQER IPWVPPECIE NPKNLTLATD   MJAK2
 *** **$**  **      *  *********  **** $             *  ** ***$ ***$*  ***$$*  *
NVCTKNLLLA REGIDSECGP .FIKLSDPGI PITVLSR... ....QECIER IPWIAPECVE DSKNLSVAAD   HJAK1

IXa                Xa                            XIa                280
KWSFGTTLWE ICSGGDKPLS ALDSQRKLQF YEDKHQLPAP KWTELANLIN NCMDYEPDFR PAFRAVIRDL   MJAK2
 **********  **  *$ **       * ** $    *    *** *   ** *$*  * *  ***$ **$
KWSFGTTLWE ICYNGEIPLK DKTLIEKERF YESRCRPVTP SCKELADLMT RCMNYDPNQR PFFRAIMRDI   HJAK1

I         350
NSLFTPDYEL LTENDMLPNM RIGALGFSGA FEDRDPTQFE ERHLKFLQQL GKGNFGSVEM CRYDPLQDNT   MJAK2
 * *      $ $$    *            *** *  * ** $ * * * ** ** *****   ***
NKLEEQNPDI VSRKKNQPTE V......... ....DPTHFT KRFLKRIRDL GEGHFGKVEL CRYDPE.DNT   HJAK1

II                 III         IV                          V       420
GEVVAVKKLQ H.STEEHLRD FEREIEILKS LQHDNIVKYK GVCYSAGRRN LRLIMEYLPY GSLRDYLQKH   MJAK2
 ** **** *    *    *$ *  $*****$  * *$****** *$*   *   $$****$**  ***$$** *
GEQVAVKSLK PESGGNHIAD LKKEIEILRN LYHENIVKYK GICTEDGGNG IKLIMEFLPS GSLKEYLPKN   HJAK1

VI          VII                       490
KERIDHKKLL QYTSQICKGM EYLGTKRYIH RDLATRNILV ENENRVKIGD FGLTKVLPQD KEYYKVKEPG   MJAK2
 * $*  *  *  *  ****** $***$$ *$* **** **$** * *  *****  *****$$   * **** **$
KNKINLKQQL KYAVQICKGM DYLGSRQYVH RDLAARNVLV ESEHQVKIGD FGLTKAIETD KEYYTVKDDR   HJAK1

VIII               IX                                              560
ESPIFWYAPE SLTESKFSVA SDVWSFGVVL YELFTYIEKS KSPPVEFMRM IGNDKQGQMI VFHLIELLKS   MJAK2
 $**$******  *  *** $* ******** *  ** ** $  ** $ * $* **   ***   *  *$   **
DSPVFWYAPE CLMQSKFYIA SDVWSFGVTL HELLTYCDSD SSPMALFLKM IGPTH.GQMT VTRLVNTLKE   HJAK1

X                 XI         600
NGRLPRPEGC PDEIYVIMTE CWNNNVSQRP SFRDLSFGWI KSGTV          MJAK2
 *** *  * ***$* $*    **    * *   ** *  *
GKRLPCPPNC PDEVYQLMRK CWEFQPSNRT SFQNLIEGFE ALLK           HJAK1
```

FIG. 8A

```
CTG CTT GAT GAC TTT GTC ATG TCT TAC CTT TCC CCT CAG TGG CGG      45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA      90
His Asp Phe Val His Gly Trp Ile Lys Val Pro Val Thr His Glu
                20                  25                  30

ACT CAG GAA GAG TGT CTT GGG ATG GCG GTG TTA GAC ATG ATG AGA     135
Thr Gln Glu Glu Cys Leu Gly Met Ala Val Leu Asp Met Met Arg
                35                  40                  45

ATA GCT AAG GAG AAA GAC CAG ACT CCA CTG GCT GTC TAT AAC TCT     180
Ile Ala Lys Glu Lys Asp Gln Thr Pro Leu Ala Val Tyr Asn Ser
                50                  55                  60

GTC AGC TAC AAG ACA TTC TTA CCA AAG TGC GTT CGA GCG AAG ATC     225
Val Ser Tyr Lys Thr Phe Leu Pro Lys Cys Val Arg Ala Lys Ile
                65                  70                  75

CAA GAC TAT CAC ATT TTA ACC CGG AAG CGA ATC AGG TAC AGA TTT     270
Gln Asp Tyr His Ile Leu Thr Arg Lys Arg Ile Arg Tyr Arg Phe
                80                  85                  90

CGC AGA TTC ATT CAG CAA TTC AGT CAA TGT AAA GCC ACT GCC AGG     315
Arg Arg Phe Ile Gln Gln Phe Ser Gln Cys Lys Ala Thr Ala Arg
                95                 100                 105

AAC CTA AAA CTT AAG TAT CTT ATA AAC CTG GAA ACC CTG CAG TCT     360
Asn Leu Lys Leu Lys Tyr Leu Ile Asn Leu Glu Thr Leu Gln Ser
               110                 115                 120

GCC TTC TAC ACA GAA CAG TTT GAA GTA AAA GAA TCT GCA AGA GGT     405
Ala Phe Tyr Thr Glu Gln Phe Glu Val Lys Glu Ser Ala Arg Gly
               125                 130                 135

CCT TCA GGT GAG GAG ATT TTT GCA ACC ATT ATA ATA ACT GGA AAC     450
Pro Ser Gly Glu Glu Ile Phe Ala Thr Ile Ile Ile Thr Gly Asn
               140                 145                 150

GGT GGA ATT CAG TGG TCA AGA GGG AAA CAT AAG GAA AGT GAG ACA     495
Gly Gly Ile Gln Trp Ser Arg Gly Lys His Lys Glu Ser Glu Thr
               155                 160                 165
```

FIG. 8B

```
CTG ACA GAA CAG GAC GTA CAG TTA TAT TGT GAT TTC CCT GAT ATT        540
Leu Thr Glu Gln Asp Val Gln Leu Tyr Cys Asp Phe Pro Asp Ile
            170                 175                 180

ATT GAT GTC AGT ATT AAG CAA GCA AAT CAG GAA TGC TCA ACT GAA        585
Ile Asp Val Ser Ile Lys Gln Ala Asn Gln Glu Cys Ser Thr Glu
            185                 190                 195

AGT AGA GTT GTG ACC GTC CAC AAG CAG GAC GGG AAG GTC TTG GAA        630
Ser Arg Val Val Thr Val His Lys Gln Asp Gly Lys Val Leu Glu
            200                 205                 210

ATA GAA CTT AGC TCA TTA AAA GAA GCC TTG TCA TTC GTG TCA TTA        675
Ile Glu Leu Ser Ser Leu Lys Glu Ala Leu Ser Phe Val Ser Leu
            215                 220                 225

ATT GAC GGG TAT TAC AGA CTA ACT GCG GAT GCA CAC CAT TAC CTC        720
Ile Asp Gly Tyr Tyr Arg Leu Thr Ala Asp Ala His His Tyr Leu
            230                 235                 240

TGC AAA GAG GTG GCT CCC CCA GCT GTG TTC GAG AAC ATA CAC AGC        765
Cys Lys Glu Val Ala Pro Pro Ala Val Phe Glu Asn Ile His Ser
            245                 250                 255

AAC TGC CAC GGC CCA ATT TCA ATG GAT TTT GCC ATC AGC AAA CTA        810
Asn Cys His Gly Pro Ile Ser Met Asp Phe Ala Ile Ser Lys Leu
            260                 265                 270

AAG AAG GCA GGA AAC CAG ACT GGA CTG TAT GTA CTT CGA TGT AGC        855
Lys Lys Ala Gly Asn Gln Thr Gly Leu Tyr Val Leu Arg Cys Ser
            275                 280                 285

CCT AAG GAC TTC AAC AAA TAC TTC CTG ACC TTT GCC GTT GAG CGA        900
Pro Lys Asp Phe Asn Lys Tyr Phe Leu Thr Phe Ala Val Glu Arg
            290                 295                 300

GAA AAT GTT ATT GAA TAT AAA CAC TGT TTG ATT ACA AAG AAT GAG        945
Glu Asn Val Ile Glu Tyr Lys His Cys Leu Ile Thr Lys Asn Glu
            305                 310                 315
```

FIG. 8C

```
AAT GGA GAG TAC AAC CTC AGT GGG ACT AAG AGG AAC TTC AGT AGT       990
Asn Gly Glu Tyr Asn Leu Ser Gly Thr Lys Arg Asn Phe Ser Ser
                320                 325                 330

CTT AAG GAC CTT TTG AAT TGC TAC CAG ATG GAA ACT GTG CGC TCA      1035
Leu Lys Asp Leu Leu Asn Cys Tyr Gln Met Glu Thr Val Arg Ser
                335                 340                 345

GAC AGT ATC ATC TTC CAG TTC ACC AAA TGC TGT CCT CCA AAG CCG      1080
Asp Ser Ile Ile Phe Gln Phe Thr Lys Cys Cys Pro Pro Lys Pro
                350                 355                 360

AAA GAT AAA TCA AAC CTT CTT GTC TTC AGA ACA AAT GGT GTT TCT      1125
Lys Asp Lys Ser Asn Leu Leu Val Phe Arg Thr Asn Gly Val Ser
                365                 370                 375

GAT GTT CAG CTC TCA CCA ACA TTA CAG AGG CAT AAT AAT GTG AAT      1170
Asp Val Gln Leu Ser Pro Thr Leu Gln Arg His Asn Asn Val Asn
                380                 385                 390

CAA ATG GTG TTT CAC AAA ATC AGG AAT GAA GAT TTG ATA TTT AAT      1215
Gln Met Val Phe His Lys Ile Arg Asn Glu Asp Leu Ile Phe Asn
                395                 400                 405
                        Iₐ
GAA AGC CTT GGC CAA GGC ACT TTT ACA AAA ATA TTT AAA GGT GTA      1260
Glu Ser Leu Gly Gln Gly Thr Phe Thr Lys Ile Phe Lys Gly Val
                410                 415                 420

AGA AGA GAA GTT GGA GAT TAT GGT CAG CTG CAC GAA ACC GAA GTT      1305
Arg Arg Glu Val Gly Asp Tyr Gly Gln Leu His Glu Thr Glu Val
                425                 430                 435
   IIₐ
CTT TTG AAA GTC CTA GAT AAA GCA CAT AGA AAC TAT TCA GAG TCT      1350
Leu Leu Lys Val Leu Asp Lys Ala His Arg Asn Tyr Ser Glu Ser
                440                 445                 450
    IIIₐ
TTC TTT GAA GCA GCA AGC ATG ATG AGT CAG CTT TCT CAC AAG CAT      1395
Phe Phe Glu Ala Ala Ser Met Met Ser Gln Leu Ser His Lys His
                455                 460                 465
```

FIG. 8D

```
  IVa
TTG GTT TTG AAT TAT GGA GTA TGT GTC TGT GGA GAG GAG AAC ATT      1440
Leu Val Leu Asn Tyr Gly Val Cys Val Cys Gly Glu Glu Asn Ile
            470             475             480

TTG GTT CAA GAG TTT GTA AAA TTT GGA TCA CTG GAT ACA TAC CTG      1485
Leu Val Gln Glu Phe Val Lys Phe Gly Ser Leu Asp Thr Tyr Leu
            485             490             495

AAG AAG AAC AAA AAT TCT ATA AAT ATA TTA TGG AAA CTT GGA GTG      1530
Lys Lys Asn Lys Asn Ser Ile Asn Ile Leu Trp Lys Leu Gly Val
            500             505             510

GCG AAG CAG TTG GCA TGG GCC ATG CAC TTC CTC GAA GAA AAA TCC      1575
Ala Lys Gln Leu Ala Trp Ala Met His Phe Leu Glu Glu Lys Ser
            515             520             525
                  VIa
CTT ATT CAT GGG AAT GTG TGT GCT AAA AAT ATC CTG CTT ATC AGA      1620
Leu Ile His Gly Asn Val Cys Ala Lys Asn Ile Leu Leu Ile Arg
            530             535             540

GAA GAA GAC AGG AGA ACG GGG AAC CCA CCT TTC ATC AAA CTT AGT      1665
Glu Glu Asp Arg Arg Thr Gly Asn Pro Pro Phe Ile Lys Leu Ser
            545             550             555
   VIIa
GAT CCT GGC ATT AGC ATT ACA GTT CTA CCG AAG GAC ATT TCT TCC      1710
Asp Pro Gly Ile Ser Ile Thr Val Leu Pro Lys Asp Ile Ser Ser
            560             565             570
                                                VIIIa
TGT TGT TTC CAA GTT CTT CAG GAG AGA ATA CCA TGG GTA CCA CCT      1755
Cys Cys Phe Gln Val Leu Gln Glu Arg Ile Pro Trp Val Pro Pro
            575             580             585

GAG TGC ATT GAG AAT CCT AAA AAT CTA ACT CTG GCA ACA GAC AAG      1800
Glu Cys Ile Glu Asn Pro Lys Asn Leu Thr Leu Ala Thr Asp Lys
            590             595             600
      IXa
TGG AGC TTC GGG ACC ACT CTG TGG GAG ATC TGC AGT GGA GGA GAT      1845
Trp Ser Phe Gly Thr Thr Leu Trp Glu Ile Cys Ser Gly Gly Asp
            605             610             615
```

FIG. 8E

```
AAG CCC CTG AGT GCT CTG GAT TCT CAA AGA AAG CTG CAG TTC TAT      1890
Lys Pro Leu Ser Ala Leu Asp Ser Gln Arg Lys Leu Gln Phe Tyr
            620             Xa              625             630
GAA GAT AAG CAT CAG CTT CCT GCA CCC AAG TGG ACA GAG TTG GCA      1935
Glu Asp Lys His Gln Leu Pro Ala Pro Lys Trp Thr Glu Leu Ala
            635             640             645
                                            XIa
AAC CTT ATA AAT AAT TGC ATG GAC TAT GAG CCA GAT TTC AGG CCT      1980
Asn Leu Ile Asn Asn Cys Met Asp Tyr Glu Pro Asp Phe Arg Pro
            650             655             660
GCT TTC AGA GCT GTC ATC CGT GAT CTT AAC AGC CTG TTT ACT CCA      2025
Ala Phe Arg Ala Val Ile Arg Asp Leu Asn Ser Leu Phe Thr Pro
            665             670             675
GAT TAT GAA CTA CTA ACA GAA AAT GAC ATG CTA CCA AAC ATG AGA      2070
Asp Tyr Glu Leu Leu Thr Glu Asn Asp Met Leu Pro Asn Met Arg
            680             685             690
ATA GGT GCC CTA GGG TTT TCT GGT GCT TTT GAA GAC AGG GAC CCT      2115
Ile Gly Ala Leu Gly Phe Ser Gly Ala Phe Glu Asp Arg Asp Pro
            695             700             705
ACA CAG TTT GAA GAG AGA CAC TTG AAG TTT CTA CAG CAG CTT GGC      2160
Thr Gln Phe Glu Glu Arg His Leu Lys Phe Leu Gln Gln Leu Gly
            710             715             720
 I
AAA GGT AAC TTC GGG AGT GTG GAG ATG TGC CGC TAT GAC CCG CTG      2205
Lys Gly Asn Phe Gly Ser Val Glu Met Cys Arg Tyr Asp Pro Leu
            725             730             735
                                            II
CAG GAC AAC ACT GGC GAG GTG GTC GCT GTG AAG AAA CTC CAG CAC      2250
Gln Asp Asn Thr Gly Glu Val Val Ala Val Lys Lys Leu Gln His
            740             745             750
                                                III
AGC ACT GAA GAG CAC CTC CGA GAC TTT GAG AGG GAG ATC GAG ATC      2295
Ser Thr Glu Glu His Leu Arg Asp Phe Glu Arg Glu Ile Glu Ile
            755             760             765
                    IV
CTG AAA TCC TTG CAG CAT GAC AAC ATC GTC AAG TAC AAG GGA GTG      2340
Leu Lys Ser Leu Gln His Asp Asn Ile Val Lys Tyr Lys Gly Val
            770             775             780
```

FIG. 8F

```
TGC TAC AGT GCG GGT CGG CGC AAC CTA AGA TTA ATT ATG GAA TAT        2385
Cys Tyr Ser Ala Gly Arg Arg Asn Leu Arg Leu Ile Met Glu Tyr
            785                 790                 795
         V
TTA CCA TAT GGA AGT TTA CGA GAC TAT CTC CAA AAA CAT AAA GAA        2430
Leu Pro Tyr Gly Ser Leu Arg Asp Tyr Leu Gln Lys His Lys Glu
            800                 805                 810

CGG ATA GAT CAC AAA AAA CTT CTT CAA TAC ACA TCT CAG ATA TGC        2475
Arg Ile Asp His Lys Lys Leu Leu Gln Tyr Thr Ser Gln Ile Cys
            815                 820                 825

AAG GGC ATG GAA TAT CTT GGT ACA AAA AGG TAT ATC CAC AGG GAC        2520
Lys Gly Met Glu Tyr Leu Gly Thr Lys Arg Tyr Ile His Arg Asp
            830                 835                 840
VI
CTG GCA ACA AGG AAC ATA TTG GTG GAA AAT GAG AAC AGG GTT AAA        2565
Leu Ala Thr Arg Asn Ile Leu Val Glu Asn Glu Asn Arg Val Lys
            845                 850                 855
         VII
ATA GGA GAC TTC GGA TTA ACC AAA GTC TTG CCG CAG GAC AAA GAA        2610
Ile Gly Asp Phe Gly Leu Thr Lys Val Leu Pro Gln Asp Lys Glu
            860                 865                 870

TAC TAC AAA GTA AAG GAG CCA GGG GAA AGC CCC ATA TTC TGG TAC        2655
Tyr Tyr Lys Val Lys Glu Pro Gly Glu Ser Pro Ile Phe Trp Tyr
            875                 880                 885
VIII
GCA CCT GAA TCC TTG ACG GAG AGC AAG TTT TCT GTG GCC TCA GAT        2700
Ala Pro Glu Ser Leu Thr Glu Ser Lys Phe Ser Val Ala Ser Asp
            890                 895                 900
         IX
GTG TGG AGC TTT GGA GTG GTT CTA TAC GAA CTT TTC ACA TAC ATC        2745
Val Trp Ser Phe Gly Val Val Leu Tyr Glu Leu Phe Thr Tyr Ile
            905                 910                 915

GAG AAG AGT AAA AGT CCA CCC GTG GAA TTT ATG CGA ATG ATT GGC        2790
Glu Lys Ser Lys Ser Pro Pro Val Glu Phe Met Arg Met Ile Gly
            920                 925                 930

AAT GAT AAA CAA GGG CAA ATG ATT GTG TTC CAT TTG ATA GAG CTA        2835
Asn Asp Lys Gln Gly Gln Met Ile Val Phe His Leu Ile Glu Leu
            935                 940                 945
```

FIG. 8G

```
                              X
CTG AAG AGC AAC GGA AGA TTG CCA AGG CCA GAA GGA TGC CCA GAT          2880
Leu Lys Ser Asn Gly Arg Leu Pro Arg Pro Glu Gly Cys Pro Asp
                950                 955                 960

GAG ATT TAT GTG ATC ATG ACA GAG TGC TGG AAC AAC AAT GTG AGC          2925
Glu Ile Tyr Val Ile Met Thr Glu Cys Trp Asn Asn Asn Val Ser
                965                 970                 975
            XI
CAG CGT CCC TCC TTC AGG GAC CTT TCC TTC GGG TGG ATC AAA TCC          2970
Gln Arg Pro Ser Phe Arg Asp Leu Ser Phe Gly Trp Ile Lys Ser
                980                 985                 990

GGG ACA GTA TAGCTGCGTG AAAGAGATGG CCTTACTCAG AGACCAAGCA              3019
Gly Thr Val

GACTTCCAGA ACCAGAACAA AGCTCTGTAG CCTTGTGTCT ACACATCCTT               3069

ATCATGACGC TAGCTAGGCA GAAAGAAAAC TGTGACGCCG TCTGCTCAAA               3119

AGCTTTGGAA AACGCCGTGC AGGTTTGTTT CATCACCATC TGTAAAAACC               3169

ACTGCTCAAG TCTGGCAGCA TGCTTGTGGG CTGATGCATG GAGCTCACCA               3219

CAGAGTCTCT GCATCTCCTC TGACAGAAGA AGAAAAATAG ACAATTTTCA               3269

ACTCACTTTT TTGAGAAATG GAAAAAATT ATAATGTAAA TTTTTCAGTG                3319

TAGGAAATAC ACAGAACATA CATGTACAGT TTTTACCACG TGGAGTGTAT               3369

AATACTTTGG CCTCTTGTGT GATTTACATG AGGGCTGATG TTTGTTAATG               3419

TTTTCTAATT TTTCCATAGG TGATCTATAA TAACTTCATG ATACAAATTA               3469

AAATGCTCAG AAAATTAAAA AAAAAA                                         3495
```

FIG. 11A

```
         1           11          21          31          41          51          61          71          81          91
     MQYLNIKEDCNAMAFCAKMRSSKKTEVNLEAPEPGVEVIFYLSDREPLRLGSGEYTAEELCIRAAQACRISPLCHNLFALYDENTKLWYAPNRTITVDDK
J1
J2
T2   MPLRHWGMARGSKPVGDGAQPMAAMGGLKVLLHWAGPGGGEPWVTFSESSLI.....AEEVCIHIAHKVGITPPCFNLFALFDAQAQVWLPPNHILEIPRD
                                                                AEE-CI--------P-C-NLFAL------W--PN--------

101         111         121         131         141         151         161         171         181         191
     MSLRLHYRMRFYFTNWHGTNDNEQSVWRHSPKKQKNGYEKKKIP DATPLLDASSLEYLFAQGQYDLVKCLAPIRDPK.TEQDGHDIENECLGMAVLAISHY
J1
J2                                               LLDDFVMSYLSPQWRHDFVHGWIKVPVTHETQEE........CLGMAVLDMRI
T2   ASLMLYFRIRFYFRNWHGMNPREPAGYRCGPPGTEASSDQTAQGMQ..LLDPASFEYLFEQGKHEFENDVASLWELS.TEEEIHHFKNESLGMAFLHLCHL
     -SL-L--R--RFYF--NWHG---N---E-----R--P------ ----LLD---S-EYLF--QG-HDFV---A------TEEE-H----NECLGMAVL---H--
                                                JH6→

201         211         221         231         241         251         261         271         281         291
J1   AMMKKMQLPELPKDISYKRYIPETLNKSIRQRNLLTRMRINNVFKDFLKEFNNKTICDSSVSTHDLKVKYLATLETLTKHYGAEIFETSMLLISSENEMN
J2   AKEKDQTPLAVYNSVSYKTFLPKCVRAKIQDYHILTRKRIRYRFRRFIQQFSQCKATARN......LKLKYLINLETLQSAFYTEQFEVKESARGPSGEEI
T2   ALRHGIPLEEVAKKTSFKDCIPRSFRRHIRQHSALTRLRLRNVFRRFLRDFQPGRLSQQM......VMVKYLATLERLAPRFGTERVPVCHLRLLAQAEGE
     A---K----L-EV-K---SYK---IP----R---IRQ-----IRQ-----LTR--RIRNVFRRFL---F--------   LKVKYLATLETL---FGTE-FEV--L-----E----
                                                                                                        JH6→

301         311         321         331         341         351         361         371         381         391
J1   WFHSNDGGNVLYY..........           .EVMVTGNLGIQWRHKPNVVSVEKEKNKLKRKKLENKDKKDEEKNK......   IREEWNNFSFFPEITHIVIKESV
J2   FAT...........                    IIITGNGGIQWSRGKHKESETL TEQDLQLYCDFP..........             DIIDVSIKQANQECSTESRI
T2   PSYIRDSGVAPTDPGPESAAGPP THEVLVTGTGGIQWPVEEEVNKEE GSGSSSARNPQASLFGKKAKAHKAFGQP ADRPREPLMAYFCDITHVVLKEHC
     -----D-G-----                     EV-VTGNGGIQW------VS-E                              -R------S-F---ITH-V-KE--
                                       JH5→                       JH5→                    JH4→

401         411         421         431         441         451         461         471         481         491
J1   VSINKQDNKKMELKLSSHEEALSFVSLVDGYFRLTADAHHYLCTDVAPPLIVHNIQNGCHGPIC-EYAI.NKLRQEGSEEGMYVLRWSCTDFDNILMTVT
J2   VTVHKQDGEVLEIELSSLKEALSFVSLIDGYYRLTADAHHYLCKEVAPPAVLENIHSNCHGPISMDFAI.SKLKKAGNQTGLYVLRCSPKDFNKYFLTFA
T2   VSIHRQDNKCLELSLPSRAAALSFESLVDGYFRLTADSSHYLCHEVAPPRLVMSIRDGIHGPLLEPFVQQAKLRP..LEDGLYLIHWSTSHPYRLILTVA
     VSIHKQDNK-LEL-LSS--EALSFVSLVDGYFRLTADAHHYLC-EVAPP--V--NI---GCHGPI----FAI---KLR---G-E-GLYVLRWS--DF----LTVA
                                                                                                    JH4→
```

FIG. 11B

```
     501                   511        521        531        541        551        561        571        581        591
J1   CFEKSEQVQGAQKQFKNFQIEVQKGRYSLHGSDRSFPSLGDLMSHLKKQILRTDNISFMLKRCCQPKPREISNLLVATKKAQEWQPVYPMSQLSFDRILK
J2   VER.....ENVIEYKHCLITKNENGEYNLSGTKRNFSSLKDLLNCYQMETVRSDSIIFQFTKCCPPKPKDKSNLLVFRTNGVSDVQLSPTLQRHNNVNQM
T2   QRSQAPDGMQSLRLRKF.PIEQQDGAFVLEGWGRSFPSVRELGAALQGCLLRAGDDCFSLRRCCLPQPGETSNLIIMRGARASPRTL.NLSQLSFHRVDQ
     -------------------K---IE-Q-G-Y-L-G--RSFPSL-DL---LQ----LR-D-I-F-L-RCC-PKP-E-SNLLV-R-----S---L-P-SQLSF-R---
                          JH3

601                   611        621        631        641        651        661        671        681        691
J1   KD.....LVQGEHLGRGTRTHIYSGTLMDYKDDEGTSEEKK........IKVILKVLDPSHRDISLAFFEAASMRQVSHKHIVVLYGVC
J2   VFHKIRNEDLIFNESLGQTFTKIFKGVRREVGDY.GQLHETE.......VLLKVLDKAHRNYSESFFEAASMSQLSHKHLVLNYGVC
T2   KE.....ITQLSHLGQGTRTNVYEGRLRVEGS..GDPEEGKMDDEDPLVPGRDRGQELRVLKVLDPSHHDIALAFYETASLMSQVSHTHLAFVHGVC
     K-      L-Q-EHLGQGTRT-IY-G-LR---GD-  G--EE-K          --V-LKVLDPSHRDISLAFFEAASMMSQVSHKHLV--YGVC
      JH2

701                   711        721        731        741        751        761        771        781        791
J1   VRDVENIMVEEFVEGGPLDLFMHRKSDVLTTPWKFKVAKQLASALSYLEDKDLVHGNVCTKNLLLAREGIDSECGPFIKLSDPGIPITVLSRQECIERIP
J2   VCGEENILVQEFVKFGSLDTYLKKNKNSINILWKLGVAKQLAWAMHFLEEKSLIHGNVCAKNILLIREEDRRTGNPFIKLSDPGISITVLPKDISSCCF.
T2   VRGPENSMVTEYEHGPLDVWLRERGHVPMAWKMVAQQLASALSYLENKNILVHGNVCGRNILLARLGLAEGTSPFIKLSDPGCGLALSREERVERIP
     VRG-ENIMV-EFVE-GPLD--L-R-------WK---VAKQLASALSYLE--K-LVHGNVC-KNILLAREG------PFIKLSDPGI-ITVLSR-E---ERIP 801                   811        821        831        841        851        861        871        881        891
J1   .........WIAPECVED.SKNLSVAADKWSFGTTLWEICYNGEIPLKDKTLIEKERFYESRCRPVTPSCKELADLMTRCMNYDPNQRPFFRAIMRDINKLE
J2   QVLQERIPWVPPECIEN.PKNLTLATDKWSFGTTLWEICSGGDKPLSALDSQRKLQFYEDKHQLPAPKWTELANLINNCMDYEPDFRPAFRAVIRDLNSLF
T2   .........WLAPECLPGGANSLSTAMDKWGFGATLLEICFDGEAPLQSRSPSEKEHFYQRQHRLPEPSCPQLATLTSQCLTYEPTQRPSFATILRDLTAVQ
     W--APEC--E---NNLS-A-DKWSFGTTLWEIC--------GE-PL-----EKE-FYE--HRLP-PSC-ELA-L---CM-YEP--QRP-FRAI-RDLN-L--
```

FIG. 11C

```
      901         911         921         931         941         951         961         971         981         991
J1   EQNPDIVSRKKNQP..........TEVDPTHF.KRFLKRIRDLGEGHFGKVELCRYDP.EDNTGEQVAVKSLKPESGGNHIADLKKEIEILRNLYHE
J2   TPDYELLTENDMLPNMRIGALGFSGAFEDRDPTQFEERHLKFLQQLGKGNFGSVEMCRYDPLQDNTGEVVAVKKLQH.STEEHLRDFEREIEILKSLQHD
T2   PHNLADVLTVNRDS.........PAVGPTTFHKRYLKKIRDLGEGHFGKVSLYCYDPTNDGTGEMVAVKALKADCGPQHRSGWKQEIDILRTLYHE
     --N----P-------------VDPT-F-KR-LK-IRDLGEGHFGKVELCRYDP--DNTGE-VAVK-LK--SG--H---D-K-EIEILR-LYHE
                         JH2
                                                                            JH1

1001        1011        1021        1031        1041        1051        1061        1071        1081        1091
J1   NIVKYKGICTEDGGNGIKLIMEFLPSGSLKEYLPKNKNINLKQQLKYAVQICKGMDYLGSRQYVHRDLAARNVLVESEHQVKIGDFGLTKAIETDKEYY
J2   NIVKYKGVCYSAGRRNLRLIMEYLPYGSLRDYLQKHKERIDHKKLLQYTSQICKGMEYLGTKRYIHRDLATRNILVENENRVKIGDFGLTKVLPQDKEYY
T2   HIIKYKGCC.EDQGE.KSLVMEYVPLGSLRDYLPRHS..IGLAQLLFAQQICEGMAYLHADYIHRDLAARNVLLDNDRLVKIGDFGLAKAVPEGHEYY
     NIVKYKG-C-EDGG-----LIMEYLP-GSLRDYLPKHK---I-LKQLL-YA-QICKGM-YLG----YIHRDLAARNVLVENE--VKIGDFGLTKA-P-DKEYY 1101        1111        1121        1131        1141        1151        1161        1171        1181        1191
J1   TVKDDRDSPVFWYAPECLMQSKFYIASDVWSFGVTLHELLTYCDSDSSPMALFLKMIG.PTHGQMTVTRLVNTLKEGKRLPCPPNCPDEVYQLMRKCWEF
J2   KVKEPGESPIFWYAPESLTESKFSVASDVWSFGVVLYELFTYIEKSKSPPVEFMRMIGNDKQGQMIVFHLIELLKSNGRLPRPEGCPDEIYVIMTECWNN
T2   RVREDGDSPVFWYAPECLKEYNFYYASDVWSFGVTLYELLTHCDSSQSPPTKFLELIG.IAQGQMTVLRLTELLEAGERLPRPDKCPCEVYHLMKNCWET
     -VKEDGDSPVFWYAPECL-ESKFY-ASDVWSFGVTLYELLTYCDSS-SPP--FL-MIG---QGQMTV-RL-ELLK-G-RLPRP--CPDEVY-LM--CWE- 1201        1211        1221        1231
J1   NVSQRPSFRDLSFGWIKSGTV*
J2   QPSNRTSFQNLIEGFEALLK*
T2   EASFRPTFENSIPILKTVHEKYQGQAPSVSSVC*
     --S-RPSF-NLI-G-----
                JH1
```

FIG. 12

```
JAK1    QNGCHGPIC-EYAI.NKLRQEGSEEGMYLRWSCT...DFDNILMTVICFEKSEQVQGAQKQFKNFQIEVQKGRYSLHGSDRSFPSLGDLMSHLKKQILRTDNISFMLKRCCQPKP
JAK2    HSNCHGPISMDFAI.SKLKKAGNQTGLYVLRCSPK...DFNKYFLTFAVER..;.ENVIEYKHCLITKNENGEYNLSGTKRNFSSLKDLLNCYQMETVRSDSIIFQFTKCCPPKP
TYK2    RDGIHGPLLEPFVQQAKLRP..LEDGLYLIHWSTS...HPYRLILTVAQRSQAPDGMQSLRLRKF.PIEQQDGAFVLEGWGRSFPSVRELGAALQGCLLRAGDDCFSLRRCCLPQP
        -GCHGPI----FAI--KLR--G-E-GLYVLRWS-----DF-----IE-Q--G-Y-L-G---RSFPSL-DL----LQ---LR-D-I-F-L-RCC-PKP
        WYHGKI----A-----L------GSYLIRES---PGDFVLS---------------Y-------G---R-F--SL--DL----YY---------------L-EPV
GAP-N   WYHGKLDRTIA.EERLR.QAGKSGSYLIRESDRRPGSFVLSFLSQT.NV......VNHFRI..IAMC.GDYY.IGG.RFSSLSDLIGYYSHVSCLLKGE.....KLLYPV
GAP-C   WFHGKISKQEA.YNLLM.TVGQACSFLVRPSDNTPGDYSLYF.RTSENIQ.R....FKI.CPTPN.NQFM.MGG.RYNSIGDIIDHYRKEQIVEGYY.....LKEPV
v-Crk   WYWGRLSRGDA.VSLLQ..GQRHGTFLVRDSGSIPGDFVLSV.SESSRVS......HYIVNSLGPAGGRRAGGE.[18]..FDSLPSLLEFYKIHYLDTT......TLIEPV
```

PROTEIN TYROSINE KINASE

This application is a divisional of Ser. No. 08/805,445, filed Feb. 25, 1997, now U.S. Pat. No. 5,821,069, which is a divisional of Ser. No. 08/446,038, filed May 19, 1995, now U.S. Pat. No. 5,658,791, which is a divisional of Ser. No. 08/064,067 filed Jun. 30, 1993 which is the national stage of PCT/US91/08889 filed Nov. 26, 1991, now U.S. Pat. No. 5,852,184.

The present invention relates generally to a novel protein tyrosine kinase and to genetic sequences encoding same.

Protein tyrosine kinases (PTKs) are structurally well suited to a role intracellular signal transduction. Many growth factor receptors, for example, transduce the extracellular stimulus they receive through interaction with their cognate ligand via an intracellular tyrosine kinase domain. At least one of the non-receptor PTKs, namely LCK, is believed to mediate the transduction in T-cells of a signal from the interaction of a cell-surface protein (CD4) with a cross-linked anti-CD4 antibody.

The broader family of PTKs can be sub-divided on the basis of structural parameters of individual members. For example, the STC family of PTKs now numbers 8 members (Marth et al, 1985; Nishizawa et al., 1986; Semba et al., 1986; Martinez et al., 1987; Sukegawa et al., 1987; Yamanishi et al., 1987; Hotzman et al., 1987; Dymecki et al., 1990), each with a characteristic complement of extra-catalytic domains, including an SH2, an SH3 domain and a variable ligand binding domain. It is clear that a process of gene duplication has taken place in this case, so that the evolutionarily successful thematic structure of this family can be employed in a variety of cellular contexts. Similar PTK structural sub-families exist based around the FGF receptor and the CSF-1 receptor (reviewed in Wilks, 1990).

However, one feature in common with the aforementioned PTKs is that each kinase bears a single highly related "catalytic" domain.

In accordance with the present invention a protein tyrosine kinase is provided which is distinct from those previously known. In particular, the protein tyrosine kinase of the present invention is unique since it possesses more than one protein kinase catalytic domain. Furthermore, the kinase does not bear an SH2 domain. The novel protein tyrosine kinase of the present invention represents a new subfamily or class of protein tyrosine kinase.

Accordingly, one aspect of the present invention is directed to an animal protein tyrosine kinase-like molecule comprising a polypeptide having multiple protein kinase catalytic domains but no SH2 domain.

Preferably, the polypeptide has two protein kinase catalytic domains.

Preferably, the animal is a mammal and is most preferably la human or a mouse.

Hereinafter, a protein having these characteristics will be referred to as a "JAK" (from JAnus Kinase: Janus, in Encyclopaedia Britannica (11th Ed) Vol XV pp 155–156). The present invention is specifically exemplified using JAK1 and JAK2 from humans and mice. This is done, however, with the understanding that the present invention extends to the whole family of JAKs from all animals and to mutants, derivatives, analogues and homologues thereof. The term "protein tyrosine kinase-like molecule" (abbreviated herein to "PTK-like molecule") is used throughout the specification and claims to emphasise that the present invention encompasses all members of the JAK family and to their mutants, derivatives, analogues and homologues.

In accordance with the present invention, there is provided a PTK-like molecule. Preferably the molecule is in biological pure or in substantially pure and/or synthetic form. The purity of the preparation is characterised by a sample comprising at least 70% by weight, preferably at least 80% by weight and most preferably at least 90% by weight PTK-like molecule. Alternatively, where the purity of the enzyme preparation is not critical, the present invention also encompasses an impure PTK-like molecule preparation but which possesses a substantial amount of JAK activity.

The present invention is directed to a naturally occurring PTK-like molecule, biologically pure or substantially pure as hereinbefore defined and to derivatives, functional analogues and homologues thereof. Such derivatives include polypeptides having single or multiple amino acid substitutions, deletions and/or additions relative to the naturally occurring sequence. These derivatives, functional analogues and homologues also encompass single or multiple substitutions, deletions and/or additions to any associated molecules such as carbohydrate, lipid and/or proteinacious moieties. Reference herein to "PTK-like molecules" includes all such derivatives, functional analogues and homologues. The present invention also extends to synthetic forms of the polypeptides which include recombinant molecules and molecules prepared by the stepwise addition of amino acids to groups of amino acids in defined order.

A range of derivatives and analogues of the PTK-like molecule are contemplated herein and include altering the molecule at its nucleotide sequence-encoding level, during its expression within a cell or in vitro or post-synthesis modification. Such derivatives and analogues include, but are not limited to, modifications to side chains, incorporation of unnatural amino acids during polypeptide synthesis and the sue of crosslinkers and other methods which impose conformational constraints on the polypeptide or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6, trinitrobenzene sulphonic acid (TNBS); acylation of amino gropus with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formtion followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ringe of a histidine residue may be accomplished by alkylation with iodoacetic acid derivatives or N-carbethoxylation with diethylpyrocarbonate.

Examples of incorporating unnatural amino acids and derivatives during polypeptide synthesis include, but are not limited to, use of norleucine, 4-amino butyric acid, 4-amino-3-hydroxy-5-phenlpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, polypeptides could be conformationally constrained by, for example, incorporation of $C_a$ and $N_a$-methylamino acids, introduction of double bonds between $C_n$ and $C_\beta$ atoms of amino acids and the formation of cyclic polypeptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof corresponding to regions of PTK-like molecules. Preferably, the PTK-like molecules will retain JAK activity. However, molecules carrying mutations in the catalytic domains rendering these inactive may be useful in, for example, titrating out activity and generation of antibodies such molecules are encompassed by the present invention.

The molecular weights of the PTK-like molecules of the present invention range from 100,000 to 200,000 daltons and preferably from 120,000 to 150,000 daltons.

In a most preferred embodiment, the present inventions provides JAK1 and JAK2. JAK1 is an approximately 1142 amino acid molecule with a molecular weight of about 132,000 daltons and a nucleotide sequence shown in FIG. 2. JAK2 is an approximately 1,100 amino acid molecule with a molecular weight of about 130,000 daltons and with a nucleotide sequence shown in FIG. 8.

The present invention is also directed to genetic sequences including DNA, cDNA and mRNA which encode the PTK-like molecules hereindescribed. Such genetic sequences include single or multiple nucleotide substitutions, deletions and/or additions relative the naturally occurring sequence and extend to sequences encoding the derivatives, functional analogues and homologues of the PTK-like molecules. The present invention also provides these genetic sequences in vector and expression vector systems either in vitro or in a biological system (i.e. eukaryotic or prokaryotic cells) transformed with such vectors or genetic sequences. In a most preferred embodiment the present invention provides cDNA encoding JAK1 and JAK2 as set forth in FIGS. 2 and 8, respectively. A range of mutants can be obtained using standard techniques such as an oligonucleotide mutagenesis and chemical mutagenesis, and all such mutants and derivatives are encompassed by the present invention.

The present invention also provides antibodies to a PTK-like molecule. Such antibodies may be monoclonal or polyclonal.

The PTK-like molecule of the present invention have varying utility such as in the phosphorylation of proteins, incorporation of labels and in the design of analogues, antagonists and agonists of JAKs.

Accordingly, another aspect of the present invention contemplates a method for phosphorylating a protein comprising contacting said protein with a phosphorylating effective amount of a PTK-like molecule, said molecule comprising a polypeptide having multiple protein kinase catalytic domains but no SH2 domain for a time and under conditions sufficient for said first protein to be phosphorylated. Preferably, the polypeptide has two protein kinase catalytic domains and most preferably is JAK1 and/or JAK2 and/or their derivatives.

The present invention is further described by reference to the following non-limiting Figures and Examples.

Figure 1B:
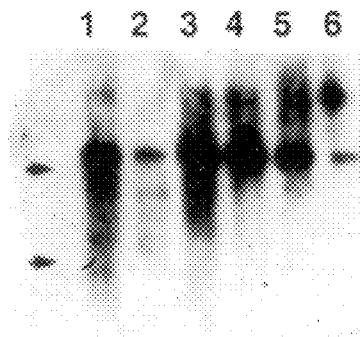

In the Figures:

FIG. 1 is a photographic representation of a Northern analysis of murine and human JAK1.

A. 2 $\mu$g aliquots of poly(A)+ mRNA from murine tissues; lane 1, lung; lane 2, liver; lane 3, kidney; lane 4, intestine; lane 5, brain; lane 6, skeletal muscle; lane 7, spleen; lane 8, salivary gland; lane 9, placenta; lane 10, mammary gland, were fractionated on a 1.0% agarose/formaldehyde (Moran et al, 1988) gel and the RNA transferred onto a Genescreen plus (Dupont) membrane. The transferred RNA was hybridized with a 1.8 kb $^{32}$P-labelled murine JAK1 probe and the filter autoradiographed for 16 hr. at −70° C. with two intensifying screens. The relative mobilities of 28S rRNA (upper arrow) and 18S rRNA (lower arrow) are shown.

B. 2 $\mu$g aliquots of poly(A)+ mRNA from the human haemopoietic cell lines; lane 1, HL60 (myelo-monocytic); lane 2, U937 (monocytic); lane 3, LK63 (pre-B); lane 4, RAJI (B-cell); lane 5, CEM (T-cell); lane 6, K562 (erythroleukaemia) were fractionated on a 1.0% agarose/formaldehyde (Moran et al, 1988) gel and the RNA transferred onto a Genescreen plus (Dupont) membrane. The transferred RNA was hybridized with a full-length $^{32}$P-labelled human JAK1 probe and the filter autoradiographed for 16 hr. at −70° C. with two intensifying screens. The relative mobilities of 28S rRNA (upper arrow) and 18S rRNA (lower arrow) are shown.

Figure 3B:
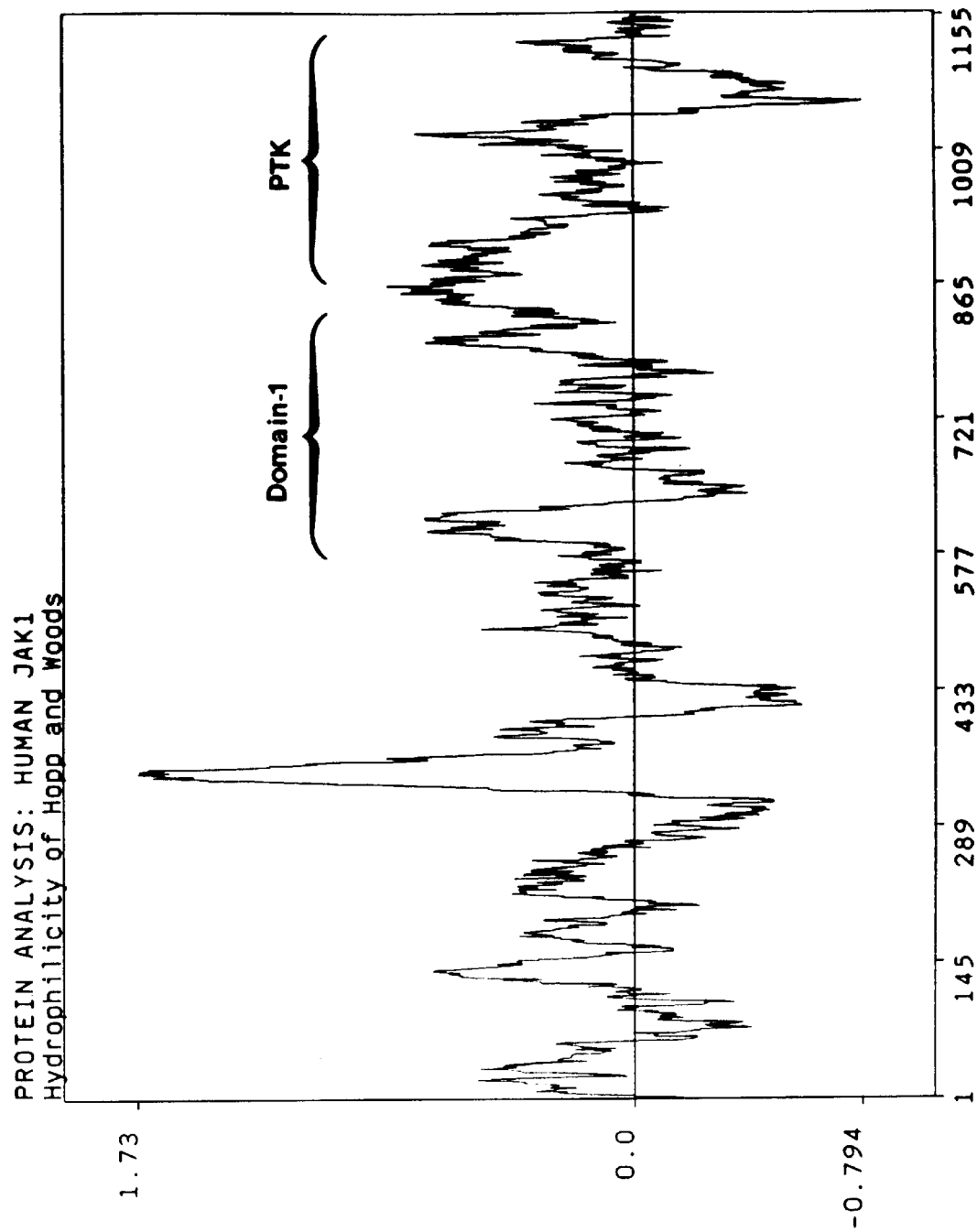

FIG. 2 is a representation showing nucleotide sequence and predicted amino acid sequence of human JAK1. The DNA sequence is numbered at the end of each line of sequence from the first nucleotide of the largest clone (pHJ7.3), the amino acid sequence (in one letter code) is numbered from the putative AUG and appears above the line to which it refers. The two kinase catalytic domains are boxed with arrows, and kinase consensus motifs are enumerated according to the nomenclature of Hanks et al (1988). The suffix a (e.g. IIa) denotes the kinase related motifs present in the first kinase-related domain (designated domain-1 in FIG. 3a) also numbered according to the same nomenclature. The tyrosine residue in an analogous position to the autophosphorylation site of a number of other protein tyrosine kinases is marked with an inverted triangle. (Sequence Id. 1)

FIG. 3 is a representation showing:

Panel A. Amino-acid sequence comparison of the two kinase-related domains of JAK1. The amino-acid sequences (expressed in one-letter amino acid code) of the two kinase-related domains (domain-1 amino-acids 576–825; domain-2 (PTK-domain) amino-acids 868–1130) of JAK1 and the human threonin/serine-specific kinase CDC2 (24) (amino acids 9–272) are aligned in order to maximize identity. The kinase-related domains have been divided into three segments and the number of amino acid residues separating each segment appears at the end of each line. Motifs held in common between at least two of these domains are both bolded and boxed. Roman numerals above the alignment correspond to the conserved domain nomenclature devised by Hanks et al (1988).

Panel B. Hydropathy plot of the human JAK1 protein. The protein sequence of human JAK1 (including the 10 extra amino acids which precede the most likely initiation codon) were analysed by the hydrophilicity algorithm of Kyte and Doolittle (1982) using a span length of 25 amino acids. The relative locations of the two kinase related domains are marked as Domain-1 and PTK. The absence of a hydrophobic transmembrane domain is clearly seen, as can the presence of a highly hydrophilic region between amino acids 323 and 350.

Figure 4A:
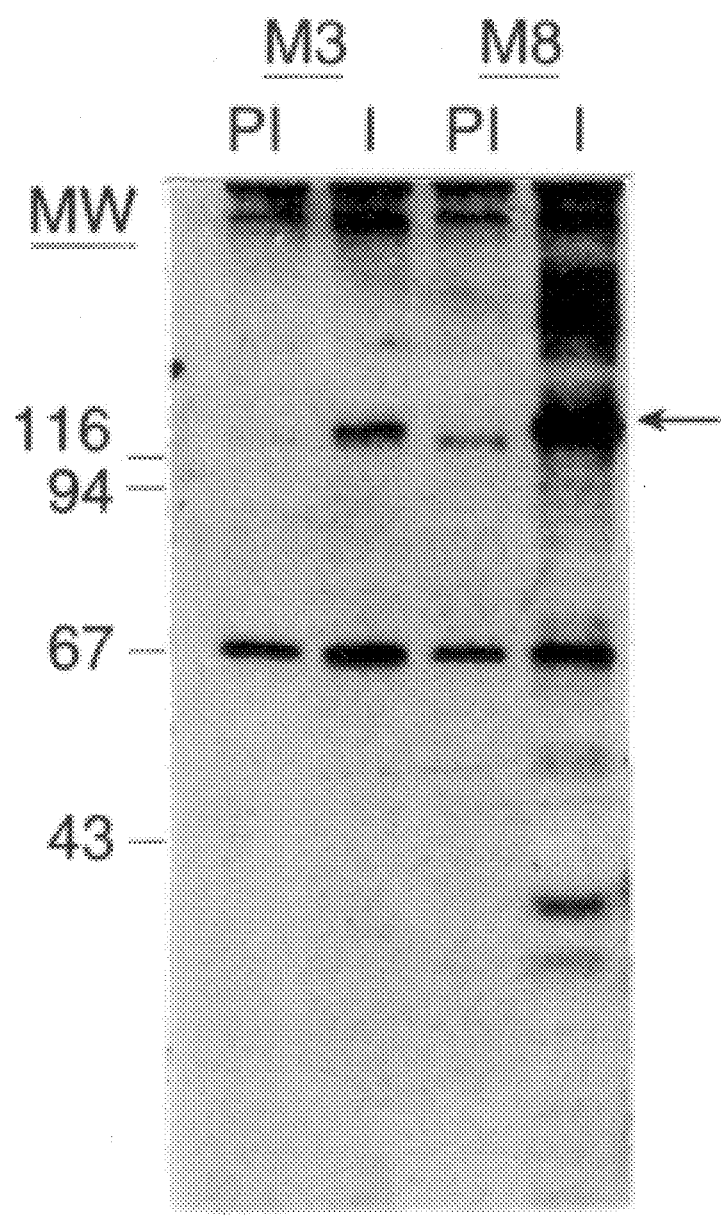
Figure 4B:
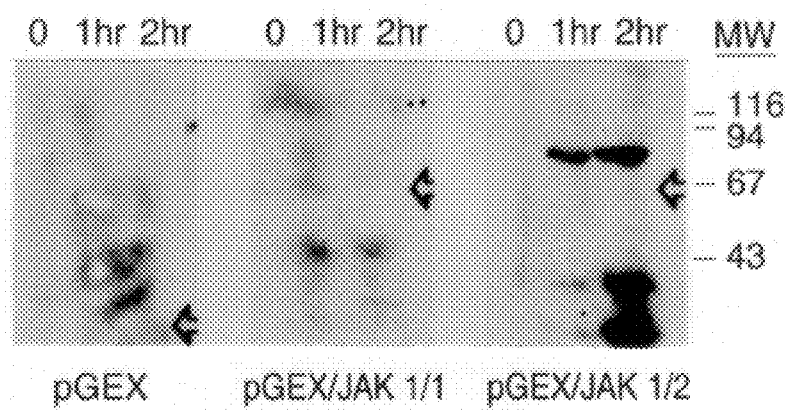
Figure 4C:
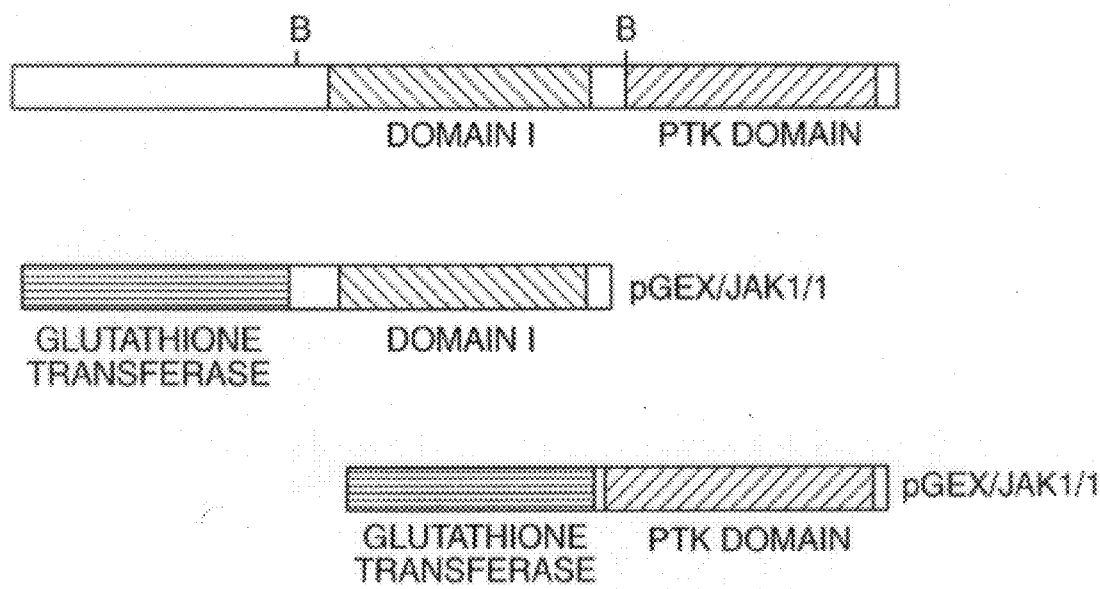

FIG. 4 is a representation of an analysis of the JAK1 protein.

Panel A. Cellular proteins of the murine mammary fibroblast cell line (17) were labelled with $^{35}$S-methionine (panel A) and immunoprecipitated with either pre-immune (PI) or immune (I) anti-JAK rabbit antiserum (raised in rabbit M8 against the pGEX/JAK1/1 fusion protein or the C-terminal peptide [M3]) and fractionated on a 9.5% SDS-PAGE gel (Laemmli, 1970). Both rabbit antisera specifically immunoprecipitated an $^{35}$S-labelled protein of apparent molecular weight 130,000D.

Panel B. Demonstration of tyrosine kinase activity in JAK1 bacterial fusion proteins. JAK1 fusion proteins were generated using pGEX2 (Smith and Johnson, 1988). The entire domain-1 region was included in construct pGEX/JAK1/1. The PTK domain portion of the fusion protein extended to the BamHI site 15 nucleotides 5' of the first glycine codon of the GXGXXG motif of the ATP binding site. An empty vector control was also performed. The bacteria were induced by the addition of 1 mM IPTG as described by Smith and Johnson (1988) and two 1 ml aliquots of the bacteria were removed at 60 minutes and 120 minutes post-induction and lysed with SDS sample buffer. Western analysis of the samples was performed using anti-phosphotyrosine antisera (PY-20 [ICN]). The arrow heads mark the positions of the GEX-JAK fusion proteins, in each induction.

Panel C. Construction of the pGEX/JAK fusion proteins. The locations of the two kinase related domains of JAK1 are shown, and below, the structure of the fusion proteins with the glutathione S-transferase gene.

FIG. 5 is a representation of a sequence comparison between JAK1 and JAK2 kinase-related domains. The deduced amino acid sequence of murine JAK2 was compared to the human JAK1 amino acid sequence by application of an alignment programme of the Staden VAX-based suite of Sequence analysis programmes. Asterisks (*) denote identity, dollar signs ($) denote conservative substitutions. Sequences are numbered with respect to the JAK1 sequence. The extent of the domain-1 and PTK domains is shown by arrows above the amino acid sequence.

Figure 6:
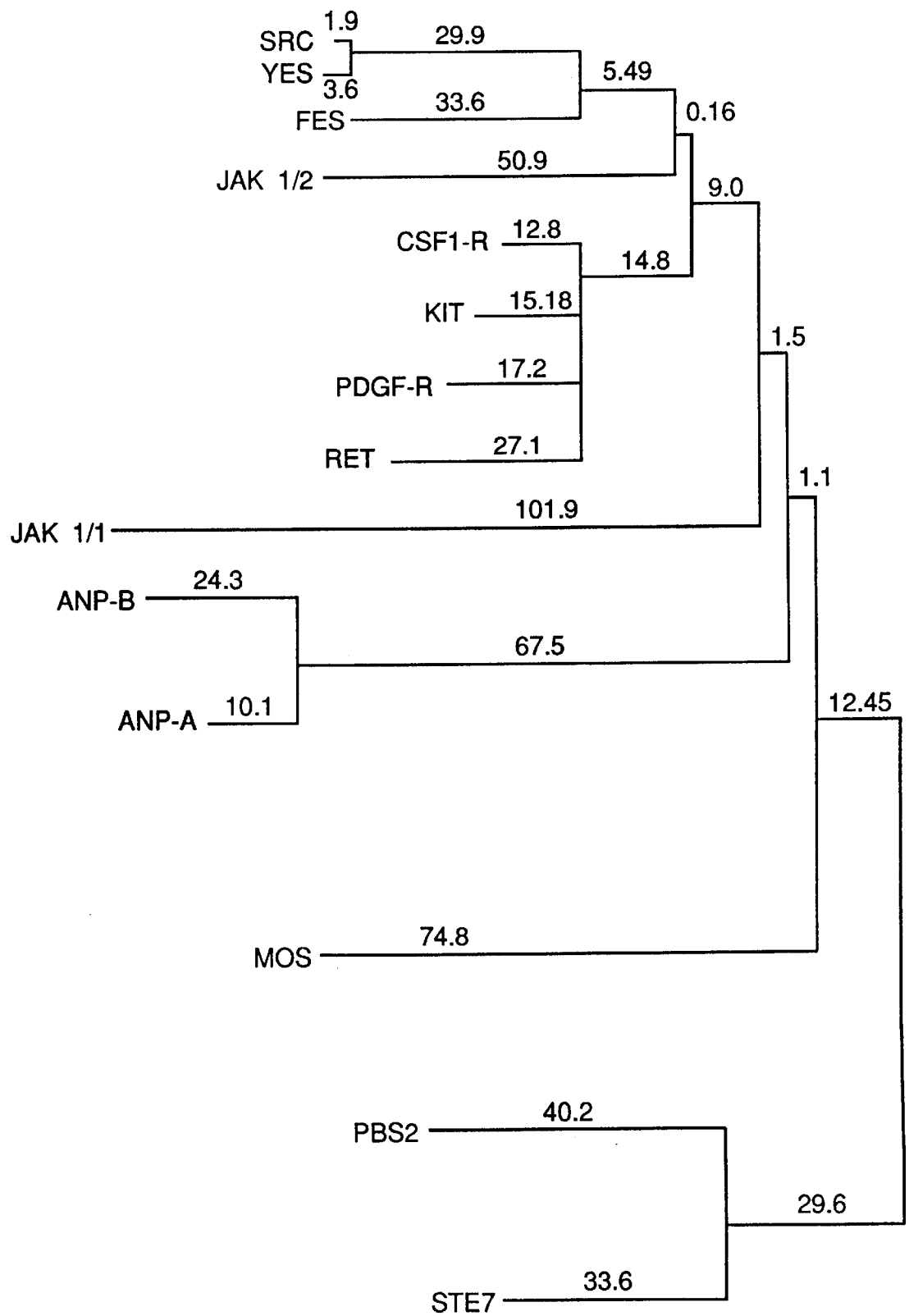

FIG. 6 is a graphical representation of a phylogenetic analysis of the two JAK1 Kinase-like domains. The tree building concept of Fitch and Margoliash (1967) as implemented by Feng and Doolittle (1987) and Hanks et al (1988) was used to generate a phylogenetic tree as described in Example 1. In each case the catalytic domain alone was used for comparison. The two kinase related domains of the JAK1 protein were compared independently. Branch order is a function of structural similarity, branch length a function of sequence identity. The abbreviations used are: SRC=c-src; YES=c-Yes; FES=c-fes; CSF1-R=Colony stimulatin factor-1 receptor; KIT=c-kit; PDGF-R=Platelet derived growth factor receptor-A; RET=c-RET; ANP-A=Atrial naturetic peptide receptor-A; ANP-B=Atrial naturetic peptide receptor-B; MOS=c-mos; PBS2=polyxin B antibiotic resistance gene product; STE7=sterile mutant wild-type allel gene product; JAK1/1=Domain-1 of Human JAK1; JAK1/2=PTK domain of Juan JAK1.

Figure 7A:
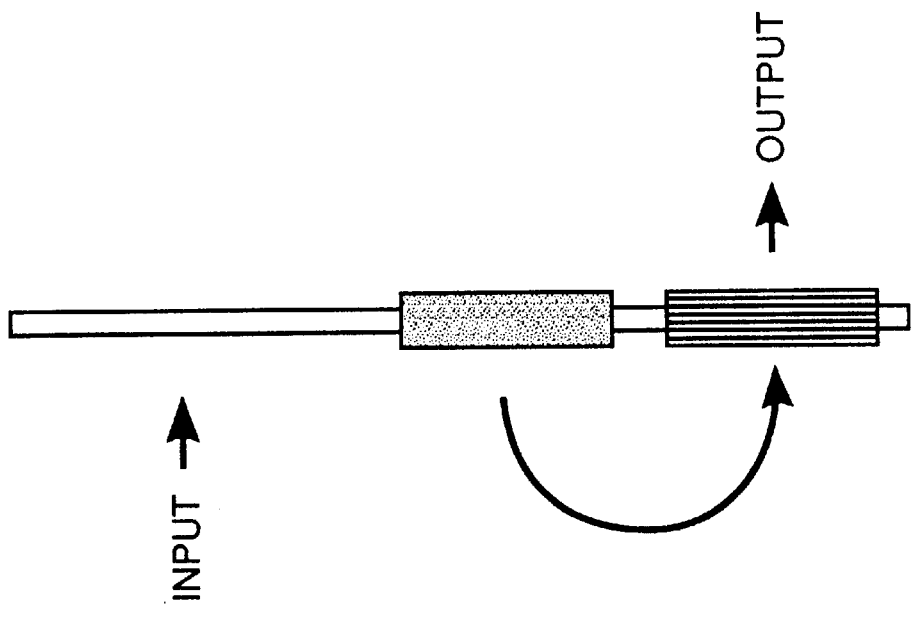
Figure 7B:
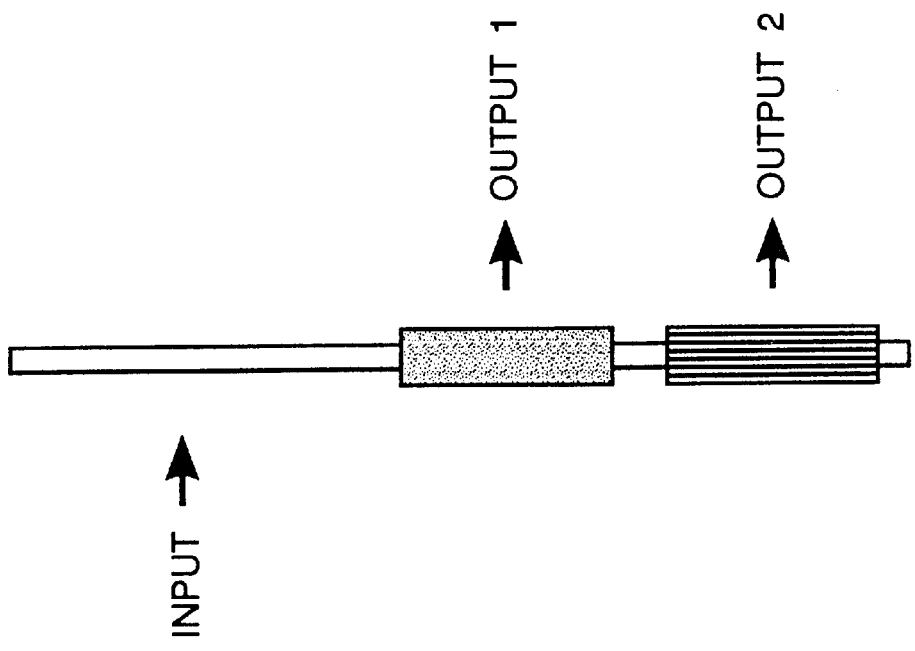

FIG. 7 is a diagrammatic representation showing models for the role of members of the JAK family of PTKs in signal transduction. Two possible scenarios are considered based on an extrapolation of the current notions of the role of PTKs in signal transduction. In panel A the N-terminal domain of the JAK protein serves to sense a particular metabolic cue and convert this input into two distinct outputs. Presumably the output of the second PTK-related domain is tyrosine kinase activity; the activity of Domain-1 remains unknown. In panel B an alternative scenario is considered. In this case the function of Domain-1 is the regulation of the PTK domain. In this scenario the sole output of the JAK protein is the PTK activity.

FIG. 8 is a representation of a nucleotide sequence and predicted amino acid sequence of murine JAK2. The nucleotide sequence is numbered beneath each line of sequence, from the first nucleotide of the most 5' clone. The predicted amino acid sequence, in one letter code, is numbered at the end of each line of sequence. The two putative kinase domains are shown boxed with arrows, and the kinase consensus motifs are enumerated according to the nomenclature of Hanks et al (1988). The subscript a denotes the kinase-related motifs present in the first kinase-related domain, which are numbered according to the same nomenclature. (Sequence Id. 2)

Figure 9:
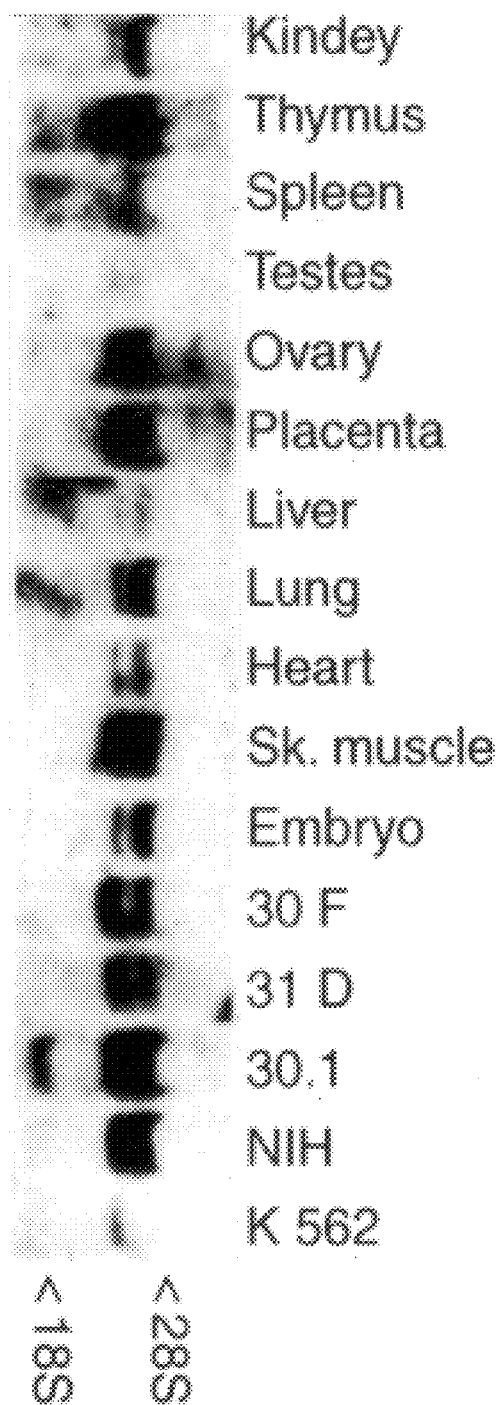

FIG. 9 is a photographic representation showing expression of JAK2 in murine tissues. Northern blot analysis of 5 µg of mRNA from each of the tissues shown on top of the figure and from various murine (30F: mammary fibroblasts; 31A: mammary epithelial cells; 30.1: factor independent subline of the hemopoietic cell line FDC.Pl; NTH: fibroblasts) and human (K562: chronic myelogenous leukaemic cells) cell line. The blots were hybridized with a $^{32}$P-labelled 2.2 kb JAK2 probe and autoradiography was for 4 days. The relative mobilities of the 28S and the 18S rRNA are indicated.

Figure 10:
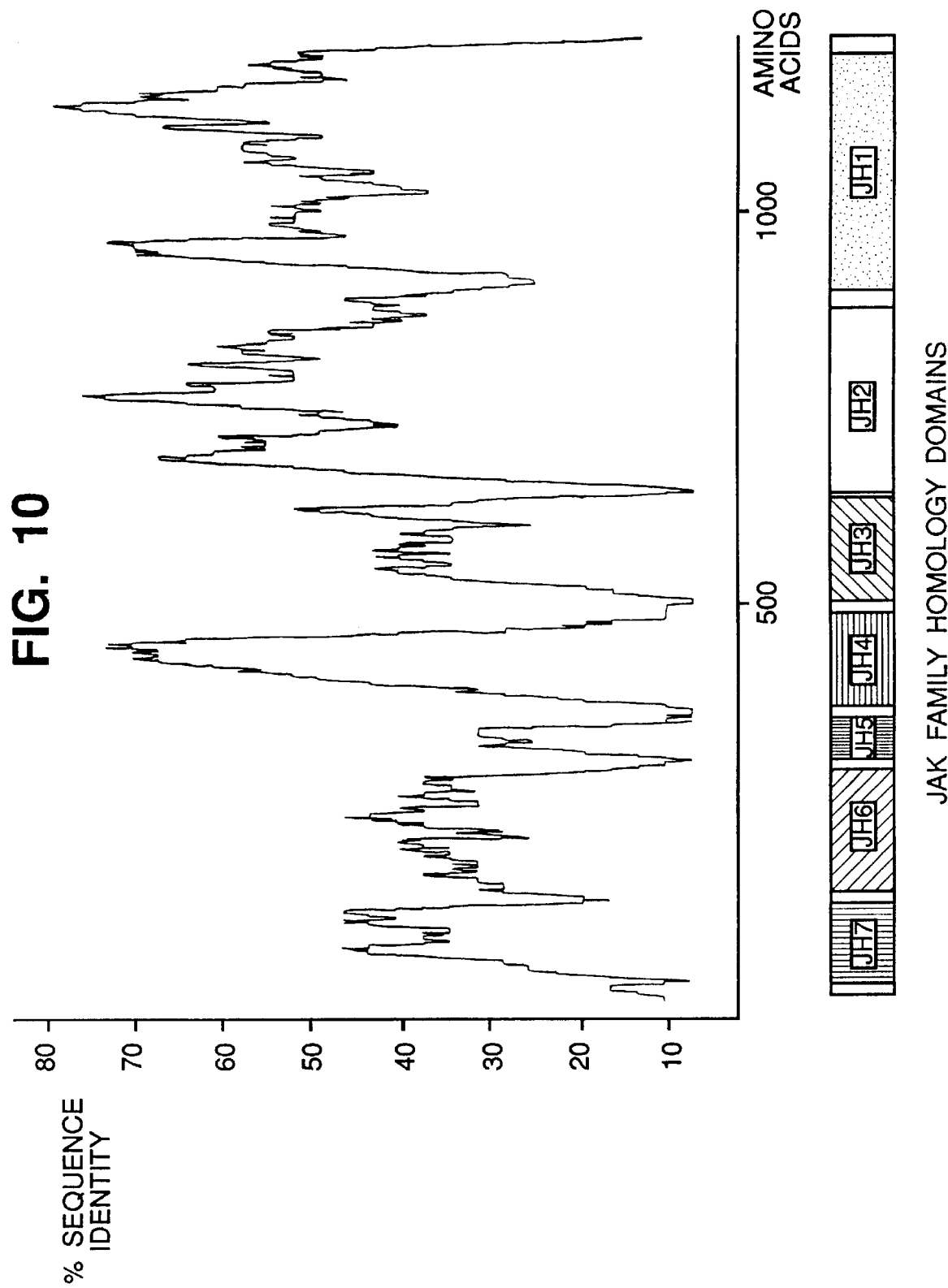

FIG. 10 is a graphical representation showing comparison of JAK1 and TYK2 amino acid sequences. The amino acid sequences of JAK1 (Wilks et al, 1991) and TYK2 (firmback-Kraft et al, 1990) were compared using the HOMOLOGY option in the programme SEQMATCH, using a window length of 21 amino acids. The ordinate of the graph represents the percentage identity between the two sequences, the abscissa represents the amino acid position in JAK1 at which the particular level of identity was calculated. The shaded boxes below the graph represent arbitrarily ascribed JAK homology domains as discussed in the text and further demonstrated in FIG. 11.

FIG. 11 is a representation showing amino acid sequence comparison of members of the JAK family of PTKs. The amino acid sequences of JAK1 (Wilks et al, 1991) (designated J1 in this figure), JAK2 (J2 in this figure), and TYK2 (Firmbach-Kraft et al, 1990) (T2 in this figure) were aligned using the CLUSTAL program (Higgins and Sharp, 1988). The numbering system is relative only to the first amino acid of JAK1, and does not take into account the insertion of gaps into this sequence, it is therefore useful only as a relative measure of location. The extent of each of the JAK homology domains was determined with reference to the homology plot shown in FIG. 10. Amino acid positions conserved in at least 2 out of the 3 sequences presented are bolded and presented below the TYK2 sequence as a consensus sequence.

FIG. 12 is a representation showing a comparison of the JH3/JH4 domain region with SH2 domains. The two SH2 domains of GAP (the more N-terminal domain denominated GAP-N (residues 178–269), the more C-terminal, GAP-C, (residues 348–438) (Trahey et al, 1988), and the SH2 domain of v-crk (residues 248–354) (Mayer et al, 1988) were compared with the JH3/JH4 of JAK1 (residues 425–536) (Wilks et al, 1991), JAK2 (residues 252–359) (this manuscript) and TYK2 (residues 449–555) (Firmbach-Kraft et al, 1990). Amino acids held in common between the two classes of sequence are denoted by vertical lines between the two sets of sequences. Conserved residues held in common by members of the same class of domain are bolded.

EXAMPLE 1

Materials and Methods

Screening of cDNA libraries

Several cDNA libraries were screened according to the protocols outlined in Maniatis et al, (1982). cDNA libraries from Murine NFS TPA activated spleen (Clontech cat.# ML1018), murine swiss-albino 3T3 fibroblast (Clontech cat.# 1023b), murine balb/c bone marrow (Clontech cat.# ML1007), murine swiss-webster whole brain (Clontech cat.# ML1002), murine ICR linoleic acid activated pleural macrophage (Clontech cat.# ML1005b), and human 1st-trimester foetal liver (Clontech cat.# HL1005b) were all generated in λgt11. cDNA libraries from murine Balb/c testis (Clontech cat.# ML1020b), murine day 10 embryonic neuro-epithelium (Reid et al, 1990) and human foreskin fibroblast cell line AG1518 (Claesson-Welsh et al, 1989) were generated in λgt10. Around $10^6$ recombinants of each of these libraries were screened on each occasion.

Library screening was carried out as follows. The FD22 (JAK1) PCR cone was labelled by nick-translation (Maniatis et al, 1982) and used to screen the murine libraries. A murine cDNA clone of 1.8 kb was isolated amongst 3 other positives from the neuro-epithelial and bone marrow cDNA libraries. Two full-length human JAK1 cDNA clones were isolated from the unamplified human foreskin fibroblast cell-line AG1518 by using the murine cDNA as a probe. Hybridisation was at 650 C. in 6×SSC; 1% SDS; 0.5% Blotto; 200 μg/ml sonicated and denatured herring sperm DNA. After hybridisation, the stringency of the final wash was 0.2×SSC; 0.1% SDS at 650 C. Filters were autoradiographed overnight using Kodak XAR-5 X-ray film.

For JAK2, the murine macrophage was screened first with the FD 17 (JAK2) PCR clone, yielding 5 positives, and a portion of the longest cDNA clone isolated and used to screen the remaining cDNA libraries. Hybridisation conditions were as above for JAK1.

DNA sequencing

Two strategies were employed for the sequencing of JAK1 and JAK2 cDNA clones. In the case of the human JAK1 sequence, the Erase-a-Base kit (PROMEGA) was employed to generate nested deletions of the largest EcoRI fragment. All of the murine JAK2 sequence data, and the remainder of the human JAK1 sequence, was determined using oligonucleotide primers based on previously determined DNA sequence. In each case the sequence information was generated using the dideoxynucleotide chain termination method (Sanger et al, 1977). All sequence information was determined on both strands.

Northern Analysis

Poly A+ mRNA samples were prepared as elsewhere described elsewhere (Wilks and Kurban, 1988). Aliquots (1 μg) were analysed by electrophoresis on a 1% agarose gel containing 2.2M formaldehyde; 20 mM MOPS, pH 6.8; 1 mM EDTA; 5 mM sodium acetate, and transferred to Hybond (Amersham, cat πRPN303N) or nitrocellulose (Schleicher & Schuell,BA85, cat #401196) membranes. Filters were prehybridised for 4 hr in 50% formamide containing 3×SSC; 5×Denhardts; 10 mM HEPES pH 7.0; 100 μg.ml 1; poly C;100 μg/ml denatured herring sperm DNA; 10 μg/ml E. coli DNA; 0.1% SDS, and hybridised in the same solution with nick-translated $^{32}$P-labelled murine or human JAK1 or JAK2 insert, for 18 hr. at 42° C. Filters were washed to a final stringency of 0.2×SSC; 0.1% SDS at 65° C., before exposure to Kodak XAR-5 X-ray film, with two intensifying screens.

Antibody Reagents and Protein Analysis

Polyclonal rabbit antisera M7 and M8 were raised against affinity purified pGEX/JAK1/1 bacterial fusion protein (see section on kinase assays). Polyclonal antibodies M3 and M4 against the C-terminal peptide (-TSFQNLIECFEALLKC-) of JAK1 were raised in rabbits. Peptide was coupled to Keyhole Limpet Heamocyanin with 0.05% gluteraldehyde, emulsified in Freunds' complete adjuvant and injected intradermally at several sites. The animals were boosted four and seven weeks later with coupled peptide emulsified in Freunds' incomplete adjuvant and bled ten days after the last injection.

Cells were metabolically labelled with either $^{35}$S-methioinine or $^{32}$P-orthophosphate in methionine- or phosphate-free medium containing 100 μCi/ml and 1 mCi/ml isotope respectively. RIPA-buffer (20 mM Tris, pH7.5 containing 1% Triton X100, 1% Na deoxycholate, 0.1% SDS, 1 mM EDTA, 1 mM PMSF) extracts were incubated on ice with antiserum and immune-complexes isolated using Protein A bearing Staphylococus aureus bacteria. Proteins were resolved by SDS-PAGE (Laemmli, 1970) and radioactively labelled bands detected by exposure to X-ray (Kodak XAR-5). The RIPA buffer for $^{32}$P-labelled cells contained in addition 20 mM EDTA, 10 mM NaF, 100 μM orothovanadate as phosphatase inhibitors.

Phosphoamino-acid analysis of excised $^{32}$P-labelled bands was carried out exactly as described by Hunter and Sefton (1980) Western blot analysis was performed as described by Towbin et al. (1979) as modified in Aiemiecki et al (1990) using either alkaline phosphatase or $^{125}$I-labelled protein-A as a detection system.

Protein Kinase Assays

A variety of protocols have been tried in order to reveal the PTK activity of the JAK1 protein. First, extraction of murine mammary fibroblasts, Reichmann et al (1989) has been performed in a range of buffers, containing Triton-X100 or Nonidet P40 (1.0%) alone, or with added Sodium Deoxycholate (0.5% or 1.0%) or in RIPA buffer (containing 1.0% Triton-X100; 1.0% Sodium Deoxycholate; 0.1% Sodium Dodecylsulphate). Cells have been extracted in the presence or absence of phosphatase inhibitors, such as 20 mM EDTA, 10 mM NaF and 100 μM Na2V04.

After immunoprecipitation, kinase assays have been performed in a range of ATP concentrations (100 nM–10 mM)

or with carrier-free γ-32P-ATP (Amersham cat #10169) in either 20 mM Tris, pH 7.4 or 50 mMM HEPES pH 7.4, with either 10 mM Mn$^{++}$, Mg$^{++}$ or Zn$^{++}$ as divalent cation. Incubations have been performed on ice (15 min), at 25° C. (15 min), at 30° C. (15 min) or at 37° C. (2 min) in the presence or absence of the phosphatase inhibitor Na2V04. Finally, γ-32P-GTP was employed as phosphate donor in lieu of γ-32P-ATP, with no success.

In order to generate the JAK1/glutathione transferase fusion proteins shown in FIG. 4, domain-1 (from nucleotides 1770–2672 in FIG. 2) and the PTK domain (from nucleotides 2672-end in FIG. 2., thus including 5 extra amino acids beyond the ATP binding glycine motif) were each fused into the BamHI site of pGEX2. The fusion protein was induced by the addition of 1 mM IPTG as described elsewhere (Smith and Johnson, 1983) and Western blot analysis performed on an induction time course with the M3 anti-JAK1 serum, and the anti-phosphotyrosine antiserum (Kamps and Sefton, 1988). Several sources of anti-phosphotyrosine antisera were tried. The data in FIG. 4b were obtained using a commercially available monoclonal antibody preparation PY-20 (ICN). In control experiments, induction of the insert-less pGEX or pGEX/JAK1 fusion protein produced no detectable tyrosine phosphorylation of bacterial substrates and the reactivity of the anti-phosphotyrosine antiserum could be completely abolished by the additional of phenyl phosphate.

Computer Aided Sequence Analysis

Amino acid sequence comparisons were performed using an alignment programme from the Staden-based suite of programmes on a VAX VMS 5.2. The phylogenetic analysis of the two kinase-like domains of JAK1 was performed using the tree-building concept of Fitch and Margoliash (1967) as implemented by Feng and Doolittle (1987). The SCORE programme used to construct the difference matrices from which the trees were derived using the BORD and BLEN programmes, were all the gift of Dr. R. Doolittle of the University of California—San Diego.

The sequence alignment shown in FIG. 11 was assembled using the CLUSTRAL program (Higgins and Sharp, 1988) on a VAX VMS 5.2 minocomputer. The homology plot shown in FIG. 10 was assembled using the HOMOLOGY option of the programme SEQMATCH. Database searches with each of the JAK homolgoy domains was reformed using the FASTA programme, based on the Pearson/Lippman algorithm (Pearson and Lippman, 1988).

RACE/Anchor PCR

RACE/Anchor PCR (Frohman et al., 1990; Loh et al., 1990) was performed by a modification of the original protocol. Briefly, 2 μg of poly(A+) mRNA is converted to cDNA using an Amersham cDNA synthesis kit (cat. No. RPN 1256) and 40 ng. of a JAK2 specific oligonucleotide primer (5'-TACACCTTTAAATATTTTTGT-3'). Prior to the addition of the reverse transcriptase, the reaction mixture was heated to 65° C. cDNA synthesis was initiated by the addition of 20 units of reverse transcriptase, and the reaction incubated at 55° C. for 75 minutes. The newly sunthesised cDNA was recovered by passage through a spun sephadex column (Maniatis et al., 1982) followed by ethanol precipitation. The mRNA/cDNA heteroduplex was G-Tailed in 30 μl containing 140 mM potassium cacodylate, 30 mM Tris, (pH7.2), 1 mM CoCl$_2$, 0.1 mM DTT, 6 mM dGTP and 15 units of TdT (IBI), for 10 minutes at 37° C. The reaction was terminated by heating to 65° C. for 15 minutes and then diluted to 500 μl with 10 mM Tris. HCl (pH7.5). 1 mM EDTA. For the RACE/Anchor PCR, 10 μl of the tailed cDNA was reconstituted into 100 μl PCR buffer (50 mM, KCl, 10 mM Tris. HCl[pH8.3], 1.5 mM MgCl$_2$, 0.01% gelatin, 200 μM of each dNTP) to this was added 50 ng of "poly-C" oligonucleotide primer (5'-CTCGAGTCGACGAATTC$_{14}$-3', and 2.5 units of TAQ polymerase (Cetus). The complementary strand of the cDNA was synthesised with one cycle of 95° C. (5 minutes), 52° C. (5 minutes) and 68° C. (40 minutes), whereupon 500 ng of the "RACE/Anchor" primer (5'-CTCGAGTCGACGAATTC-3', and a nested JAK2 specific primer (5'-CTTGCTTAATACTGACATCA-3') were added and the reaction mix subjected to 30 cycles of 95° C. (1 minute), 52° C. (2 minutes) and 68° C. (5 minutes). The PCR product was phenol/chloroform extracted, precipitated and resuspended in 100 μl of water. The amplified material was then kinased, size fractionated on a low-melting temperature agarose gel and cloned into SmaI cleaved M13mp8. Plaques were screened by hybridisation with a JAK2 cDNA and positives sequenced.

EXAMPLE 2

Isolation and DNA Sequencing of cDNA Clones Encoding JAK1

JAK1 cDNA was cloned using PCR. Northern analysis (FIG. 1a and b) demonstrated that in both mouse and human tissues and cell lines FD22 (JAK1) was encoded by a single widely expressed 5.4 kb mRNA. Human cDNA clones of FD22 (JAK1) were isolated from a human foreskin fibroblast cell line (AG 1518) cDNA library (Claesson-Welsh et al, 1989). Two of the 8 primary isolates cloned contained inserts which were candidates for being full-length cDNAs (~5.3 kb).

The nucleotide sequence of human JAK1 is shown in FIG. 2. The 5' end of the clone has stop codons in all 3 reading frames prior to the putative initiation ATG. Two ATG start codons in frame with the longest open reading frame were found at positions 40 and 70 in the nucleotide sequence shown in FIG. 2. The first of these is embedded in a particularly poor "Kozak" consensus sequence (Kozak, 1984) (-TAAATGCAG-), whereas the second matches strongly with the optimal consensus sequence defined by Kozak, namely -GCCATGGCT-. The second ATG is considered to be the initiation codon for this protein, since the first one transgresses one of the strongest correlations found in the sequences which precede initiation codons, namely the presence of a T residue (in lieu of an A residue) 3 nucleotides before the ATG sequence. At the 3'end, an in-frame stop codon at position 3502 defines the C-terminus of the protein. A large (1.405 kb) 3' untranslated region containing a polyadenylation signal completes the mRNA sequence.

The JAK1coding region of 3426 bp encodes a protein of 1142 amino-acids with a calculated molecular mass of 132,000 daltons. The PTK catalytic domain is located towards the C-terminus of the JAK1 protein (FIG. 2). In describing the structural features of this domain we have chosen to adopt the nomenclature of Hanks et al (1988). The putative ATP binding site composed of the motif GLY-X-GLY-X-X-GLY- (subdomain I) followed by an invariant lysine residue )subdomain II) is located between amino acid residues 871 and 896 of the JAK1 protein. The core motifs of the PTK catalytic domain (sub-domains VI to IX) are also in their appropriate locations, and are well conserved with respect to their primary sequence and their relationship to each other. The presence of a tyrosine residue at position 1022 in the JAK1 protein, 11 residues C-terminal to subdomain VII (a similarly placed tyrosine is a site of tyrosine autophosphorylation in v-fps; Weinmaster et al 1984) is a consistent feature of members of the PTK family and is considered diagnostic of membership of this class of kinases. The arginine residue at position 1126 (domain XI) marks the end of the highly conserved regions of the PTK catalytic domain and the entire catalytic domain of 255 amino acids is approximately 28% (with c-fes; Wilks and Kurbon, 1988) to 37% (with TRK; Kozman et al 1988) identical to other functionally defined PTKs. Finally, there is a rare variant of the highly conserved subdomain VIII motif (residues 1032–1039), which is believed to lie close to the active site (Hanks et al 1988). The presence of phenylalanine and tyrosine flanking the conserved tryptophan in this motif is unique to JAK1 and JAK2.

A second protein kinase-related domain (designated here Domain-1) is located between amino acids 578 and 824, 47 amino acids N-terminal to the putative PTK domain. All of the conserved elements of protein kinases are preserved spatially in this domain. In FIG. 2 these elements are numbered with respect to their similarity to the subdomains of protein kinases described by Hanks et al (1988) (with the suffix$_a$, e.g. III$_a$) and the amino acid sequences of the two kinases-related domains of JAK1 are compared to each other and to human CDC2 (Lee and Nurse, 1987) in FIG. 3a. The overall structural similarity of this domain to the kinase domains of both the PTK and threonine/serine kinase families strongly suggest that this region of the protein also functions as a protein kinase. There are, however, significant differences in the sequences of key motifs within this domain which suggest that Domain-1 may confer a catalytic activity other than serine/threonine or tyrosine phosphorylation. For example, sub-domain VI$_a$ is poorly conserved with respect to the equivalent motifs in the other kinase families, and the normally invariant -ASP-PHE-GLY- sequence of the PTK and threonine/serine kinase families (sub-domain VII$_a$) is replaced by the motif ASP-PRO-GLY- in Domain-1 of JAK1. As has been noted elsewhere, the conservation of the precise sequence of sub-domain VI in the PTK and threonine/serin kinase families appears to correlate with the substrate specificity of the kinase. Thus, it is possible that Domain-1 of the JAK1 kinase has a substrate specificity other than that exhibited by the PTK and threonine/serine kinase has a substrate specificity other than that exhibited by the PTK and threonine/serine kinases. In support of this notion there are subtle differences in the normally consistent spacing between certain key motifs in Domain-1 of JAK1. The components of the ATP binding site (sub-domains I$_a$ and II$_a$) are some 7 amino acids further apart in this domain that they are both the PTK family and the threonine/serine kinase family. Moreover, the spacing between sub-domains VI$_a$ and VII$_a$ in this region is also longer by 9 amino acids. Conversely, the distance between sub-domains VII$_a$ and IX$_a$ is 7 amino acids shorter than the corresponding region in the PTK catalytic domain. The overall structure of this domain can be expected to be somewhat different to the catalytic domains of the members of the PTK and threonine/serine kinase families.

The sequences N-terminal to Domain-1 bear no homology to any other portion of a previously described protein kinase. Specifically, no homology was detected to the SH2 domain described for the cytoplasmic PTKs such as c-fes/fps (Sadowski et al 1986) GAP (Trahey et al 1988) and the phospholipase-C family of proteins (Sub et al 1988). This is a particularly interesting observation since no other non-receptor PTK has been described which lacks this feature. A hydrophilicity plot failed to demonstrate the present of a hydrophobic domain characteristic of the growth factor receptor type of PTK (FIG. 3b) suggesting that this protein is wholly intracellular like other members of the non-receptor class of PTKs. The one outstanding feature of the JAK1 hydropathy plot is the highly hydrophilic sequence between residues 320–350. This sequence is not conserved in the murine JAK2 protein, however, its remarkable nature suggests that it may well be involved in some function of the JAK1 protein.

Expression of JAK1 protein

Several antisera were generated against the human JAK1 protein. Poplyclonal antisera directed against the hexadecamer -TSFQNLIECFALLKC- (the C-terminal 15 amino acids of JAK1) were raised in rabbits and used to investigate the nature of the JAK1 protein. A second rabbit antiserum was generated using a pGEX bacterial fusion protein containing the entire Domain-1 region of the human JAK1 protein (see Example 1). Preliminary sequence analysis of cDNA clones of murine JAK1 demonstrated that the C-terminus of the human and murine versions of this protein were identical whereas the murine and human Domain-1 regions exhibited a very high degree of identity. Both systems have thus been used interchangably in the investigation of the properties of the JAK1 protein.

Both antisera have been used for Western blot analyses and immunoprecipitation studies and the data confirm the mRNA expression studies shown in FIG. 1. For example, antisera M3 and M8 both immunoprecipitate a protein of the same apparent molecular weight (130 kDaltons) from $^{35}$S-methionine labelled murine breast fibroblasts (FIG. 4a). From the same source, $^{32}$P-orthophosphate labelled JAK1 was immunoprecipitated as a phosphothreonine and phosphoserine containing phosphorprotein. It is a feature characteristic of members of the protein tyrosine kinase family that they are able to accomplish an act of self phosphorylation in vitro. Intriguingly, despite the high degree of sequence similarity held by the PTK-related sequence of JAK1 to the PTK family in general, it was not possible to demonstrate tyrosine kinase catalytic activity in immuno-precipitates of this protein from any of the murine or human sources tested. A wide range of possibilities has been tested in search of suitable conditions for the demonstration of this activity. These are listed in Example 1. The reason for the lack of activity may lie with a steric effect of the antibody in the active site of the enzyme.

In order to determine whether domain-1 or the PTK domain, in isolation, bore catalytic activity, bacterial fusion proteins of each were generated with the glutathione transferase protein of *Schistosoma japonigum* (Smith and Johnson, 1988) and an attempt was made to demonstrate with the aid of anti-phosphotyrosine antibodies (Kamps and Sefton, 1988) the co-ordinate induction of the fusion protein and tyrosine phosphorylated protein. In this system there is no cross-reactive background of the anti-phosphotyrosine antiserum, since there are no tyrosine kinases in bacteria (FIG. 4b). The phosphorylation of bacterial proteins on tyrosine is thus easily detectable with such a serum. In this series of experiments neither pGEX without insert nor pGESX bearing Domain-1(pGEX/JAK/1/1) demonstrated any tyrosine kinase activity. The pGEX/JAK/1 fusion protein was further purified by affinity chromatography on a reduced glutathione column and have failed to detect any kinase activity using either histones, casaein or enolase as an exogenous substrate. The pattern of inducible tyrosine phosphorylation exhibited by the pGEX PTK fusion protein (pGEX/JAK/2 ) (FIG. 4b) is usually simple for an ectopically expressed PTK fusion protein. Remarkably, the autophosphorylation of the fusion protein itself does not seem to occur, an observation which may go some way toward explaining why we have had difficulty in demonstrating PTK activity in the intact protein.

cDNA clones covering the coding region of the PCR clone FD17(JAK2) have been isolated from a range of murine cDNA libraries. The predicted amino acid sequences of JAK2 and JAK1 show several regions of significant similarity to each other (FIG. 5, see also Example 3).

Phylogenetic Analysis

The phlogenetic relationship of the catalytic domains of most of the protein kinases has been determined using the tree-building programme of Feng and Doolittle (1987). FIG. 6 shows the phylogenetic relationship of the two kinase-related domains of the JAK1 protein to the rest of the kinase family. It is concluded from this family tree that these two domains had a common ancestor which pre-dated the development of the PTK sub-family. It is of interest to note that the kinase-related domains of the ANP-receptor/guanylate cyclase family diverge at a point close by.

EXAMPLE 3

Cloning and Sequencing of JAK2

Sequence of Murine JAK2

The PCR clone FD17 was used as a basis to begin the cloning of longer cDNA clones of murine JAK2. cDNAs were isolated from a range of cDNA libraries, and by RACE (Frohman et al, 1989, Loh et al, 1989). The sequence of murine JAK2 is presented in FIG. 8. The predicted amino acid sequence indicates that this protein is highly related to JAK1. At the C-terminus, and extending approximately 270 amino acids towards the N-terminus (AA 715 980), are sequences bearing all the hallmarks of a PTK catalytic domain. These are labelled in FIG. 8 according to the Hanks nomenclature. Immediately N-terminal to this (AA 400–660) lies the kinase-related domain characteristic of this class of PTKs (Wilks et al, 1991). The approach outlined in Example 2 in relation to JAK1 was followed and assigned these kinase related domains according to the Hanks nomenclature, appending the suffix Na to denote their origin. One unusual feature of this domain is an apparent insertion of seven amino acids between elements VIIa and VIIIa (Hanks nomenclature; Hanks and Quinn, 1991) with respect to other members of the family. This feature appeared in only one clone of the four sequenced which covered this region, and it remains possible that its presence is due to an infrequent splicing aberration, rather than being of functional significance.

Distribution of JAK2

Northern analysis of the expression of JAK2 in the mouse demonstrated two mRNA transcripts (4.8 and 4.4 kb) hybridizing to the JAK 2 probe under low and high stringency hybridization conditions (FIG. 9). It is intriguing to note that the levels of these transcripts alter with respect to one another in different tissues. For example, the kidney, spleen and lung appear to express predominantly the larger form, whereas ovary, placenta, skeletal (sk) muscle and all murine cell lines analyzed express both forms at about equal levels. Under lower stringency hybridization conditions the murine JAK2 probe recognizes human JAK 2 RNA (K562), however, only the smaller transcript of 4.4 kb could be detected. At this point, the origins of either of the two transcripts are unclear and no differential splicing events which could account for the differences between them could be detected. However, the major source of size differential in these transcripts may lie in the use of different polyadenylation signals. JAK2 is widely expressed in mouse organs, albeit to different levels. High expression was found in thymus, skeletal muscle, ovary and placenta, but JAK2 transcripts were barely detectable in testes or liver. In addition, JAK2 expression was detected in murine cell lines of fibroblastic (30F, NIH), epithelial (31D) and hemopoietic (30.1) origin.

JAK Family Homology Domains

The cloning of JAK1 and JAK2 has facilitated the identification of JAK family homology domains. FIG. 10 shows a comparison of the amino acid sequences of JAK1. Sequence identity between these two proteins manifests itself as seven clearly defined homology domains. These seven domains are defined at a primary sequence level in FIG. 11. The PTK domain is classified as the JAK-homology Domain 1 (JH1), the second kinase related domain as the JH2 Domain, and so on to JH7. The boundaries of the JAK homology domains are arbitrary, and may or may not define functional domains. However, their delineation is a useful device to aid the consideration of the overall structural similarity of this class of proteins. The structure of the JH1 and JH2 Domains are described in Example 2. The JH3 is one of the least highly conserved of the JAK homology domains, each family member bearing between 35% (JAK2) to 50% (JAK1) of the deduced consensus sequence. The JH4 domain bears the sequence -GLYVLRWS- close to its C-terminal boundary, which has some degree of homology to the SH2 domain core sequence (see below). In addition, the most highly conserved sub-domain of this region bears a potential tyrosine phosphorylation site, namely, -VDGYFRI-. Overall, the JH4 domain has between 51% (JAK2) and 64% (JAK1) of the deduced consensus sequence for this domain. Each of the remaining JAK homology domains has been independently screened against the NBRL and EMBASG databases using the FASTA programme. There were no compelling homologous found with anything in these databases. It is concluded that these domains are structurally and functionally conserved in members of the JAK family of PTKs, but may not, in contradistinction to the SH2 and SH3 domains of the src family of PTKs, have a role to play in other signal transduction molecules.

The apparent absence of an SH2 domain in any of the JAK family of PTKs is intriguing. Subtle sequence similarities have been detected between SH2 consensus sequences and portions of the JH3 and JH4 domains (H. Hanafusa and A. Bemards, personal communication). FIG. 12 shows an alignment of these two domains. Whilst the similarity of the JH3 domain to SH2 domains is most evident in the region surrounding the SH2 core sequence (FLVRES), the homology does not extend far in either direction beyond this region, and only reappears again close to the C-terminal boundary of the SH2 domain. This lack of extensive homology, particularly in many of those elements most highly conserved between SH2 domains (Koch et al, 1991) (presumably indicating those residues most intimately involved in the conserved function of this domain), suggests that the homology detected is either happenstance, or the product of considerable sequence divergence in evolution. The SH2 domain is currently believed to interact with phosphorylated tyrosine residues on the substrates of PTKs (reviewed in Pawson, 1989; Koch et al, 1991). Whether the JH3/JH4 domains play a similar functional role remains to be determined.

EXAMPLE 4

To show that the JAKs are represented in a range of animals, oligonucleotide probes were prepared and used to amplify and screen genomes from a variety of animals. JAK DNA was detected in Drosophila, xenopus, mouse and human genomes. The main conserved sequence was DPG common to all animals tested.

REFERENCES:

Claesson-Welsh, L., Eriksson, A., Westermark, B. and Heldin, C. H., *Proc. Nat. Acad. Sci. USA* 86: 4917–4921, 1989.

Feng, D. F. and Doolittle, R. F. *Jour. Mol. Evolution* 25: 351–360, 1987.

Fitch, W. M. and Margoliash, E., *Science* 12: 279–284, 1967.

Hunter, T., and Sefton, B. M. *Proc. Nat. Acad. Sci.* 77: 1311–1315, 1980.

Kamps, M. P., and Sefton, B. M. *Oncogene* 2: 305–315, 1988.

Kozak, M. *Nucleic Acids Res.* 12: 857–872, 1984.

Kozma, S. C. Redmond, S. M. S., Xiano-Chang, F., Saurer, S. M. Groner, B., and Hynes, N. E. *EMBO J.* 7: 147–154, 1988.

Kyle, J. and Doolittle, R. F. *J. Mol. Biol.* 157: 105–132, 1982.

Laemmli, U. K. *Nature* (London) 227: 680–685, 1970.

Lee, M. G. and Nurse, P. *Nature (London)* 327: 31–35, 1987.

Maniatis, T., Fritsch, E. F., and Sambrook, J., in *Molecular Cloning: A Laboratory Manual* Cold Spring Harbor, N. Y. 1982.

Moran, M. F., Koch, C. A., Sadowski, I., and Pawson, T. *Oncogene* 3: 665–672, 1988.

Reichmann, E., Ball, R., Groner, B., and Friis, R. R., *J. Cell Biol.* 108: 1127–1138, 1989.

Smith, D. B. and Johnson, K. S. *Gene* 67: 31–40, 1988.

Suh, P., Ryu, S. H., Moon, K. H., Suh, H. W., and Rhee, S. G. *Cell* 54: 161:169, 1988.

Towbin, H., Stehelin, T., and Gordon, J., *Proc. Nat. Acad. Sci. USA* 76: 4350–4354, 1979.

Weinmaster, G., Zoller, M. M., Smith, M., Hinze, E., and Pawson, T. *Cell* 37: 559–568, 1984.

Wilks, A. F. and Kurban, R. R. *Oncogene*, 3: 289–294, 1988.

Ziemiecki, A., Mueller, R. G., Xiao-Chang, F., Hynes, N. E. and Kozma, S., *EMBO J.* 9 191–196, 1990.

Dymecki, S. M., Neiderhuber, J. E., and Desiderio, S. V. *Science* 247: 332–336, 1990.

Firmbach-Kraft, I., Byers, M., Showes, T., Dalla-Favera, R., and Krolewski, J. J., *Oncogene* 5: 1329–1336, 1990.

Frohman, M. A., Dush, M. K. and Martin, G., *Proc. Nat. Acad. Sci. USA* 85: 8998–9002, 1988.

Hanks, S. K. and Quinn, A. M. *Methods in Enzymology* 200: 38–62, 1991.

Hanks, S., K., Quinn, A. M. and Hunter, T. *Science* 241: 42–52, 1988.

Higgins, D. G. and Sharp, P. M. *Gene* 73: 237–244, 1988.

Holtzman, D. A., Cook, W. D. and Dunn, A. R. *Proc. Natl. Acad. Sci. USA* 84: 8325–8329, 1987.

Koch, C. A., Anderson, D., Moran, M. F., Ellis, C., and Pawson, T., 252: 668–674, 1991.

Loh, E. Y., Elliott, J. F., Cwirla, S., Lanier, L. L. and Davis, M. M. *Science* 243: 217–220, 1989.

Marth, J. D., Peet, R., Krebs, E. G., and Perimutter, R. M. *Cell* 43: 393–404, 1985.

Martinez, R., Mathey-Prevot, B., Bernards, A. and Baltimore, D. *Science* 237: 411–414, 1987.

Mayer, B. J., Hamaguchi, H., and Hanafusa, H., *Nature* 332: 272–274, 1988.

Nishizawa, M., Semba, K., Yoshida, M. C. Yamamotto, T., Sasaki, M., and Toyoshima, K. *Mol. Cell Biol.* 6: 511–517, 1986.

Pawson, T., *Oncogene* 3: 491–495, 1988.

Pearson, W. R. and Lippman, D. J. *Proc. Natl. Acad. Sci.* 85: 2444–2448, 1988.

Reid, H. H., Wilks, A. F., and Bernard, O., *Proc. Natl. Acad. Sci.* 87: 1596–1600, 1990.

Sadowski, I., Stone, J. C., and Pawson, T. *Mol. Cell Biol.* 6: 4396–4408, 1986.

Sanger, F., Nicklen, S., and Couson, A. R., *Proc. Nat. Acad. Sci. USA* 74: 5463–5467, 1977.

Semba, K., Nishizawa, M., Myajima, N., Yoshida, M. C., Sukagawa, J., Yamanishi, Y., Sasaki, M., Yamamoto, T., and Toyoshima, K., *Proc. Natl. Acad. Sci.* 83: 5459–5463, 1986.

Sukegawa, J., Semba, K., Yamanishi, Y., Nishizawa, M., Myajima, N., Kamamoto, T., and Toyoshima, K., *Mol. Cell Biol.* 7: 41–47, 1987.

Trahey, M., Wong, G., Halenbeck, R., Rubinfeld, B., Martin, G. A., Ladner, M., Long, C. M., Crosier, W. J., Watt, K., Koths, K., and McCormick, F., *Science* 243: 1697–1700, 1988.

Wilks, A. F., *Process in Growth Factor Research* 2: 97–111, 1990.

Wilks, A. F., Harpur, A., Kurban, R. R., Ralph, S. J., Zuercher, G., and Ziemiecki, A. *Molecular and Cellular Biology* 11: 2057–2065, 1991.

Yamamishi, Y., Fukushige, S. I., Semba, K., Sukegawa, J., Miyajima, N., Matsubara, K. I., Yamamoto, T., and Toyoshima, K., *Molec. Cell Biol.* 7: 237–243, 1987.

We claim:

1. A method for phosphorylating a protein, comprising contacting said protein with a phosphorylating effective amount of an isolated mammalian polypeptide comprising an amino acid sequence encoded by a nucleic acid molecule, the complementary sequence of which hybridizes to SEQ ID NO: 1 or to SEQ ID NO: 2, at 65° C., 6XSSC, 1% SDS, with a final wash of 0.2×SSC, 0.1% SDS, at 65° C., wherein said polypeptide comprises multiple catalytic domains, but no SH2 domains, for a time and under conditions sufficient for said protein to be phosphorylated.

2. The method of claim 1, wherein the mammalian polypeptide is a human protein or a mouse protein.

3. The method of claim 1, wherein said polypeptide comprises two protein kinase catalytic domains.

4. The method of claim 1, wherein said polypeptide has molecular weight of from about 120,000 daltons to about 140,000 daltons as determined by SDS-PAGE.

5. The method of claim 1, wherein said polypeptide has a molecular weight of from about 100,000 daltons to about 200,000 daltons as determined by SDS-PAGE.

6. The method of claim 1, wherein said polypeptide consists of the amino acid sequence set forth in SEQ ID NO: 24.

7. The method of claim 1, wherein said polypeptide consists of the amino acid sequence set forth in SEQ ID NO: 25.

* * * * *

UNITED STATES PATENT AND TRADEMARK OFFICE
CERTIFICATE OF CORRECTION

PATENT NO. : 5,910,426
DATED : June 8, 1999
INVENTOR(S) : Wilks, et al

It is certified that error appears in the above-identified patent and that said Letters Patent is hereby corrected as shown below:

In column 1, line 53, change "la" to -- a --.

In column 2, line 35, change "sue" to -- use --.

In column 8, line 46, change "X-ray (Kodak XAR-5)" to -- X-ray film (Kodak XAR-5) --.

In column 6, line 44, change "NTH" to -- NIH --.

In column 8, line 52, change "Aiemiecki" to -- Ziemiecki --.

In column 10, line 38, change "70" to -- 76 --.

In column 12, line 33, change "phosphorprotein" to -- phosphoprotein --.

In column 12, line 63, change "casaein" to -- casein --.

In column 14, line 35, change "homologous" to -- homologies --.

In column 63, line 29, change "phosphorylating" to -- tyrosine phosphorylating --.

UNITED STATES PATENT AND TRADEMARK OFFICE
CERTIFICATE OF CORRECTION

PATENT NO.   : 5,910,426
DATED        : June 8, 1999
INVENTOR(S)  : Wilks, et al It is certified that error appears in the above-identified patent and that said Letters Patent is hereby corrected as shown below:

In column 64, line 37, change "24" to -- 18 --.

In column 64, line 40, change "25" to -- 19 --.

Signed and Sealed this

Twenty-sixth Day of September, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 4234 base pairs
      (B) TYPE:  nucleic acid
      (C) STRANDEDNESS:  single
      (D) TOPOLOGY:  linear (ii) MOLECULE TYPE:  nucleic acid (xi) SEQUENCE DESCRIPTION:  SEQ ID NO: 1:

```
TGGCCGCCTA GCGAGCTGCC GGTCGACCCC AGCCAGCCGA GCGACGGGCG CTGCCTGGCC      60
```

-continued

```
CAGGGCACAC GGAAGTGCGC TTCTCTGAAG TAGCTTTGGA AAGTAGAGAA GAAAATCCAG            120

TTTGCTTCTT GGAGAACACT GGACAGCTGA ATAA ATG CAG TAT CTA AAT                   169
                                     Met Gln Tyr Leu Asn
                                        -10

ATA AAA GAG GAC TGC AAT GCC ATG GCT TTC TGT GCT AAA ATG AGG                 214
Ile Lys Glu Asp Cys Asn Ala Met Ala Phe Cys Ala Lys Met Arg
    -5              +1              5

AGC TCC AAG AAG ACT GAG GTG AAC CTG GAG GCC CCT GAG CCA GGG                 259
Ser Ser Lys Lys Thr Glu Val Asn Leu Glu Ala Pro Glu Pro Gly
10              15                  20

GTG GAA GTG ATC TTC TAT CTG TCG GAC AGG GAG CCC CTC CGG CTG                 304
Val Glu Val Ile Phe Tyr Leu Ser Asp Arg Glu Pro Leu Arg Leu
25              30                  35

GGC AGT GGA GAG TAC ACA GCA GAG GAA CTG TGC ATC AGG GCT GCA                 349
Gly Ser Gly Glu Tyr Thr Ala Glu Glu Leu Cys Ile Arg Ala Ala
40              45                  50

CAG GCA TGC CGT ATC TCT CCT CTT TGT CAC AAC CTC TTT GCC CTG                 394
Gln Ala Cys Arg Ile Ser Pro Leu Cys His Asn Leu Phe Ala Leu
55              60                  65

TAT GAC GAG AAC ACC AAG CTC TGG TAT GCT CCA AAT CGC ACC ATC                 439
Tyr Asp Glu Asn Thr Lys Leu Trp Tyr Ala Pro Asn Arg Thr Ile
70              75                  80

ACC GTT GAT GAC AAG ATG TCC CTC CGG CTC CAC TAC CGG ATG AGG                 484
Thr Val Asp Asp Lys Met Ser Leu Arg Leu His Tyr Arg Met Arg
85              90                  95

TTC TAT TTC ACC AAT TGG CAT GGA ACC AAC GAC AAT GAG CAG TCA                 529
Phe Tyr Phe Thr Asn Trp His Gly Thr Asn Asp Asn Glu Gln Ser
100             105                 110

GTG TGG CGT CAT TCT CCA AAG AAG CAG AAA AAT GGC TAC GAG AAA                 574
Val Trp Arg His Ser Pro Lys Lys Gln Lys Asn Gly Tyr Glu Lys
115             120                 125

AAA AAG ATT CCA GAT GCA ACC CCT CTC CTT GAT GCC AGC TCA CTG                 619
Lys Lys Ile Pro Asp Ala Thr Pro Leu Leu Asp Ala Ser Ser Leu
130             135                 140

GAG TAT CTG TTT GCT CAG GGA CAG TAT GAT TTG GTG AAA TGC CTG                 664
Glu Tyr Leu Phe Ala Gln Gly Gln Tyr Asp Leu Val Lys Cys Leu
145             150                 155

GCT CCT ATT CGA GAC CCC AAG ACC GAG CAG GAT GGA CAT GAT ATT                 709
Ala Pro Ile Arg Asp Pro Lys Thr Glu Gln Asp Gly His Asp Ile
160             165                 170

GAG AAC GAG TGT CTA GGG ATG GCT GTC CTG GCC ATC TCA CAC TAT                 754
Glu Asn Glu Cys Leu Gly Met Ala Val Leu Ala Ile Ser His Tyr
175             180                 185

GCC ATG ATG AAG AAG ATG CAG TTG CCA GAA CTG CCC AAG GAC ATC                 799
Ala Met Met Lys Lys Met Gln Leu Pro Glu Leu Pro Lys Asp Ile
190             195                 200

AGC TAC AAG CGA TAT ATT CCA GAA ACA TTG AAT AAG TCC ATC AGA                 844
Ser Tyr Lys Arg Tyr Ile Pro Glu Thr Leu Asn Lys Ser Ile Arg
205             210                 215

CAG AGG AAC CTT CTC ACC AGG ATG CGG ATA AAT AAT GTT TTC AAG                 889
Gln Arg Asn Leu Leu Thr Arg Met Arg Ile Asn Asn Val Phe Lys
220             225                 230

GAT TTC CTA AAG GAA TTT AAC AAC AAG ACC ATT TGT GAC AGC AGC                 934
Asp Phe Leu Lys Glu Phe Asn Asn Lys Thr Ile Cys Asp Ser Ser
235             240                 245

GTG TCC ACG CAT GAC CTG AAG GTG AAA TAC TTG GCT ACC TTG GAA                 979
Val Ser Thr His Asp Leu Lys Val Lys Tyr Leu Ala Thr Leu Glu
250             255                 260

ACT TTG ACA AAA CAT TAC GGT GCT GAA ATA TTT GAG ACT TCC ATG                 1024
```

|  |  |  |
|---|---|---|
| Thr Leu Thr Lys His Tyr Gly Ala Glu Ile Phe Glu Thr Ser Met<br>265        270        275 | | |
| TTA CTG ATT TCA TCA GAA AAT GAG ATG AAT TGG TTT CAT TCG AAT<br>Leu Leu Ile Ser Ser Glu Asn Glu Met Asn Trp Phe His Ser Asn<br>280        285        290 | 1069 | |
| GAC GGT GGA AAC GTT CTC TAC TAC GAA GTG ATG GTG ACT GGG AAT<br>Asp Gly Gly Asn Val Leu Tyr Tyr Glu Val Met Val Thr Gly Asn<br>295        300        305 | 1114 | |
| CTT GGA ATC CAG TGG AGG CAT AAA CCA AAT GTT GTT TCT GTT GAA<br>Leu Gly Ile Gln Trp Arg His Lys Pro Asn Val Val Ser Val Glu<br>310        315        320 | 1159 | |
| AAG GAA AAA AAT AAA CTG AAG CGG AAA AAA CTG GAA AAT AAA GAC<br>Lys Glu Lys Asn Lys Leu Lys Arg Lys Lys Leu Glu Asn Lys Asp<br>325        330        335 | 1204 | |
| AAG AAG GAT GAG GAG AAA AAC AAG ATC CGG GAA GAG TGG AAC AAT<br>Lys Lys Asp Glu Glu Lys Asn Lys Ile Arg Glu Glu Trp Asn Asn<br>340        345        350 | 1249 | |
| TTT TCA TTC TTC CCT GAA ATC ACT CAC ATT GTA ATA AAG GAG TCT<br>Phe Ser Phe Phe Pro Glu Ile Thr His Ile Val Ile Lys Glu Ser<br>355        360        365 | 1294 | |
| GTG GTC AGC ATT AAC AAG CAG GAC AAC AAG AAA ATG GAA CTG AAG<br>Val Val Ser Ile Asn Lys Gln Asp Asn Lys Lys Met Glu Leu Lys<br>370        375        380 | 1339 | |
| CTC TCT TCC CAC GAG GAG GCC TTG TCC TTT GTG TCC CTG GTA GAT<br>Leu Ser Ser His Glu Glu Ala Leu Ser Phe Val Ser Leu Val Asp<br>385        390        395 | 1384 | |
| GGC TAC TTC CGG CTC ACA GCA GAT GCC CAT CAT TAC CTC TGC ACC<br>Gly Tyr Phe Arg Leu Thr Ala Asp Ala His His Tyr Leu Cys Thr<br>400        405        410 | 1429 | |
| GAC GTG GCC CCC CCG TTG ATC GTC CAC AAC ATA CAG AAT GGC TGT<br>Asp Val Ala Pro Pro Leu Ile Val His Asn Ile Gln Asn Gly Cys<br>415        420        425 | 1474 | |
| CAT GGT CCA ATC TGT ACA GAA TAC GCC ATC AAT AAA TTG CGG CAA<br>His Gly Pro Ile Cys Thr Glu Tyr Ala Ile Asn Lys Leu Arg Gln<br>430        435        440 | 1519 | |
| GAA GGA AGC GAG GAG GGG ATG TAC GTG CTG AGG TGG AGC TGC ACC<br>Glu Gly Ser Glu Glu Gly Met Tyr Val Leu Arg Trp Ser Cys Thr<br>445        450        455 | 1564 | |
| GAC TTT GAC AAC ATC CTC ATG ACC GTC ACC TGC TTT GAG AAG TCT<br>Asp Phe Asp Asn Ile Leu Met Thr Val Thr Cys Phe Glu Lys Ser<br>460        465        470 | 1609 | |
| GAG CAG GTG CAG GGT GCC CAG AAG CAG TTC AAG AAC TTT CAG ATC<br>Glu Gln Val Gln Gly Ala Gln Lys Gln Phe Lys Asn Phe Gln Ile<br>475        480        485 | 1654 | |
| GAG GTG CAG AAG GGC CGC TAC AGT CTG CAC GGT TCG GAC CGC AGC<br>Glu Val Gln Lys Gly Arg Tyr Ser Leu His Gly Ser Asp Arg Ser<br>490        495        500 | 1699 | |
| TTC CCC AGC TTG GGA GAC CTC ATG AGC CAC CTC AAG AAG CAG ATC<br>Phe Pro Ser Leu Gly Asp Leu Met Ser His Leu Lys Lys Gln Ile<br>505        510        515 | 1744 | |
| CTG CGC ACG GAT AAC ATC AGC TTC ATG CTA AAA CGC TGC TGC CAG<br>Leu Arg Thr Asp Asn Ile Ser Phe Met Leu Lys Arg Cys Cys Gln<br>520        525        530 | 1789 | |
| CCC AAG CCC CGA GAA ATC TCC AAC CTG CTG GTG GCT ACT AAG AAA<br>Pro Lys Pro Arg Glu Ile Ser Asn Leu Leu Val Ala Thr Lys Lys<br>535        540        545 | 1834 | |
| GCC CAG GAG TGG CAG CCC GTC TAC CCC ATG AGC CAG CTG AGT TTC<br>Ala Gln Glu Trp Gln Pro Val Tyr Pro Met Ser Gln Leu Ser Phe<br>550        555        560 | 1879 | |
| GAT CGG ATC CTC AAG AAG GAT CTG GTG CAG GGC GAG CAC CTT GGG | 1924 | |

-continued

```
                Asp Arg Ile Leu Lys Lys Asp Leu Val Gln Gly Glu His Leu Gly
                565                 570                 575

AGA GGC ACG AGA ACA CAC ATC TAT TCT GGG ACC CTG ATG GAT TAC           1969
Arg Gly Thr Arg Thr His Ile Tyr Ser Gly Thr Leu Met Asp Tyr
580                 585                 590

AAG GAT GAC GAA GGA ACT TCT GAA GAG AAG AAG ATA AAA GTG ATC           2014
Lys Asp Asp Glu Gly Thr Ser Glu Glu Lys Lys Ile Lys Val Ile
595                 600                 605

CTC AAA GTC TTA GAC CCC AGC CAC AGG GAT ATT TCC CTG GCC TTC           2059
Leu Lys Val Leu Asp Pro Ser His Arg Asp Ile Ser Leu Ala Phe
605                 615                 620

TTC GAG GCA GCC AGC ATG ATG AGA CAG GTC TCC CAC AAA CAC ATC           2104
Phe Glu Ala Ala Ser Met Met Arg Gln Val Ser His Lys His Ile
625                 630                 635

GTG TAC CTC TAT GGC GTC TGT GTC CGC GAC GTG GAG AAT ATC ATG           2149
Val Tyr Leu Tyr Gly Val Cys Val Arg Asp Val Glu Asn Ile Met
640                 645                 650

GTG GAA GAG TTT GTG GAA GGG GGT CCT CTG GAT CTC TTC ATG CAC           2194
Val Glu Glu Phe Val Glu Gly Gly Pro Leu Asp Leu Phe Met His
655                 660                 665

CGG AAA AGT GAT GTC CTT ACC ACA CCA TGG AAA TTC AAA GTT GCC           2239
Arg Lys Ser Asp Val Leu Thr Thr Pro Trp Lys Phe Lys Val Ala
670                 675                 680

AAA CAG CTG GCC AGT GCC CTG AGC TAC TTG GAG GAT AAA GAC CTG           2284
Lys Gln Leu Ala Ser Ala Leu Ser Tyr Leu Glu Asp Lys Asp Leu
685                 690                 695

GTC CAT GGA AAT GTG TGT ACT AAA AAC CTC CTC CTG GCC CGT GAG           2329
Val His Gly Asn Val Cys Thr Lys Asn Leu Leu Leu Ala Arg Glu
700                 705                 710

GGA ATC GAC AGT GAG TGT GGC CCA TTC ATC AAG CTC AGT GAC CCC           2374
Gly Ile Asp Ser Glu Cys Gly Pro Phe Ile Lys Leu Ser Asp Pro
715                 720                 725

GGC ATC CCC ATT ACG GTG CTG TCT AGG CAA GAA TGC ATT GAA CGA           2419
Gly Ile Pro Ile Thr Val Leu Ser Arg Gln Glu Cys Ile Glu Arg
730                 735                 740

ATC CCA TGG ATT GCT CCT GAG TGT GTT GAG GAC TCC AAG AAC CTG           2464
Ile Pro Trp Ile Ala Pro Glu Cys Val Glu Asp Ser Lys Asn Leu
745                 750                 755

AGT GTG GCT GCT GAC AAG TGG AGC TTT GGA ACC ACG CTC TGG GAA           2509
Ser Val Ala Ala Asp Lys Trp Ser Phe Gly Thr Thr Leu Trp Glu
760                 765                 770

ATC TGC TAC AAT GGC GAG ATC CCC TTG AAA GAC AAG ACG CTG ATT           2554
Ile Cys Tyr Asn Gly Glu Ile Pro Leu Lys Asp Lys Thr Leu Ile
775                 780                 785

GAG AAA GAG AGA TTC TAT GAA AGC CGG TGC AGG CCA GTG ACA CCA           2599
Glu Lys Glu Arg Phe Tyr Glu Ser Arg Cys Arg Pro Val Thr Pro
790                 795                 800

TCA TGT AAG GAG CTG GCT GAC CTC ATG ACC CGC TGC ATG AAC TAT           2644
Ser Cys Lys Glu Leu Ala Asp Leu Met Thr Arg Cys Met Asn Tyr
805                 810                 815

GAC CCC AAT CAG AGG CCT TTC TTC CGA GCC ATC ATG AGA GAC ATT           2689
Asp Pro Asn Gln Arg Pro Phe Phe Arg Ala Ile Met Arg Asp Ile
820                 825                 830

AAT AAG CTT GAA GAG CAG AAT CCA GAT ATT GTT TCC AGA AAA AAA           2734
Asn Lys Leu Glu Glu Gln Asn Pro Asp Ile Val Ser Arg Lys Lys
835                 840                 845

AAC CAG CCA ACT GAA GTG GAC CCC ACA CAT TTT GAG AAG CGC TTC           2779
Asn Gln Pro Thr Glu Val Asp Pro Thr His Phe Glu Lys Arg Phe
850                 855                 860

CTA AAG AGG ATC CGT GAC TTG GGA GAG GGC CAC TTT GGG AAG GTT           2824
```

```
                                                              -continued

Leu Lys Arg Ile Arg Asp Leu Gly Glu Gly His Phe Gly Lys Val
865                 870                 875

GAG CTC TGC AGG TAT GAC CCC GAA GAC AAT ACA GGG GAG CAG GTG      2869
Glu Leu Cys Arg Tyr Asp Pro Glu Asp Asn Thr Gly Glu Gln Val
880                 885                 890

GCT GTT AAA TCT CTG AAG CCT GAG AGT GGA GGT AAC CAC ATA GCT      2914
Ala Val Lys Ser Leu Lys Pro Glu Ser Gly Gly Asn His Ile Ala
895                 900                 905

GAT CTG AAA AAG GAA ATC GAG ATC TTA AGG AAC CTC TAT CAT GAG      2959
Asp Leu Lys Lys Glu Ile Glu Ile Leu Arg Asn Leu Tyr His Glu
910                 915                 920

AAC ATT GTG AAG TAC AAA GGA ATC TGC ACA GAA GAC GGA GGA AAT      3004
Asn Ile Val Lys Tyr Lys Gly Ile Cys Thr Glu Asp Gly Gly Asn
925                 930                 935

GGT ATT AAG CTC ATC ATG GAA TTT CTG CCT TCG GGA AGC CTT AAG      3049
Gly Ile Lys Leu Ile Met Glu Phe Leu Pro Ser Gly Ser Leu Lys
940                 945                 950

GAA TAT CTT CCA AAG AAT AAG AAC AAA ATA AAC CTC AAA CAG CAG      3094
Glu Tyr Leu Pro Lys Asn Lys Asn Lys Ile Asn Leu Lys Gln Gln
955                 960                 965

CTA AAA TAT GCC GTT CAG ATT TGT AAG GGG ATG GAC TAT TTG GGT      3139
Leu Lys Tyr Ala Val Gln Ile Cys Lys Gly Met Asp Tyr Leu Gly
970                 975                 980

TCT CGG CAA TAC GTT CAC CGG GAC TTG GCA GCA AGA AAT GTC CTT      3184
Ser Arg Gln Tyr Val His Arg Asp Leu Ala Ala Arg Asn Val Leu
985                 990                 995

GTT GAG AGT GAA CAC CAA GTG AAA ATT GGA GAC TTC GGT TTA ACC      3229
Val Glu Ser Glu His Gln Val Lys Ile Gly Asp Phe Gly Leu Thr
1000                1005                1010

AAA GCA ATT GAA ACC GAT AAG GAG TAT TAC ACC GTC AAG GAT GAC      3274
Lys Ala Ile Glu Thr Asp Lys Glu Tyr Tyr Thr Val Lys Asp Asp
1015                1020                1025

CGG GAC AGC CCT GTG TTT TGG TAT GCT CCA GAA TGT TTA ATG CAA      3319
Arg Asp Ser Pro Val Phe Trp Tyr Ala Pro Glu Cys Leu Met Gln
1030                1035                1040

TCT AAA TTT TAT ATT GCC TCT GAC GTC TGG TCT TTT GGA GTC ACT      3364
Ser Lys Phe Tyr Ile Ala Ser Asp Val Trp Ser Phe Gly Val Thr
1045                1050                1055

CTG CAT GAG CTG CTG ACT TAC TGT GAT TCA GAT TCT AGT CCC ATG      3409
Leu His Glu Leu Leu Thr Tyr Cys Asp Ser Asp Ser Ser Pro Met
1060                1065                1070

GCT TTG TTC CTG AAA ATG ATA GGC CCA ACC CAT GGC CAG ATG ACA      3454
Ala Leu Phe Leu Lys Met Ile Gly Pro Thr His Gly Gln Met Thr
1075                1080                1085

GTC ACA AGA CTT GTG AAT ACG TTA AAA GAA GGA AAA CGC CTG CCG      3499
Val Thr Arg Leu Val Asn Thr Leu Lys Glu Gly Lys Arg Leu Pro
1090                1095                1100

TGC CCA CCT AAC TGT CCA GAT GAG GTT TAT CAG CTT ATG AGA AAA      3544
Cys Pro Pro Asn Cys Pro Asp Glu Val Tyr Gln Leu Met Arg Lys
1105                1110                1115

TGC TGG GAA TTC CAA CCA TCC AAT CGG ACA AGC TTT CAG AAC CTT      3589
Cys Trp Glu Phe Gln Pro Ser Asn Arg Thr Ser Phe Gln Asn Leu
1120                1135                1130

ATT GAA GGA TTT GAA GCA CTT TTA AAA TAAGAAGCAT GAATAACATT        3636
Ile Glu Gly Phe Glu Ala Leu Leu Lys
1135                1140

TAAATTCCAC AGATTATCAA GTCCTTCTCC TGCAACAAAT GCCCAAGTCA TTTTTTAAAA   3696

ATTTCTAATG AAAGAAGTTT GTGTTCTGTC CAAAAAGTCA CTGAACTCAT ACTTCAGTAC   3756

ATATACATGT ATAAGGCACA CTGTAGTGCT TAATATGTGT AAGGACTTCC TCTTTAAATT   3816
```

| | | |
|---|---|---|
| TGCACCAGTA ACTTAGTGAC ACATAATGAC AACCAAAATA TTTGAAAGCA CTTAAGCACT | 3876 |
| CCTCCTTGTG GAAAGAATAT ACCACCATTT CATCTGGCTA GTTCACCATC ACAACTGCAT | 3936 |
| TACCAAAAGG GGATTTTTGA AAACGAGGAG TTGACCAAAA TAATATCTGA AGATGATTGC | 3996 |
| TTTTCCCTGC TGCCAGCTGA CTGAAATGTT TTCCTGGCAC ATTAATCATA GATAAAGAAG | 4056 |
| ATTGATGGAC TTAGCCCTCA AACAGTATCT ATACAGTACT AGACCATGCA TTCTTAAAAT | 4116 |
| ATTAGATACC AGGTAGTATA TATTGTTTCT GTACAAAAAT GACTGTATTC TCTCACCAGT | 4176 |
| AGGACTTAAA CTTTGTTTCT CCAGTGGCTT AGCTCCTGTT CCTTTGGGTG ATCACTAG | 4234 |

(2) INFORMATION FOR SEQ ID NO:2:

(i) SEQUENCE CHARACTERISTICS:
        (A) LENGTH: 3495 base pairs
        (B) TYPE: nucleic acid
        (D) STRANDEDNESS: single
        (D) TOPOLOGY: linear (ii) MOLECULE TYPE: nucleic acid (xi) SEQUENCE DESCRIPTION: SEQ ID NO: 2:

```
CTG CTT GAT GAC TTT GTC ATG TCT TAC CTT TCC CCT CAG TGG CGG        45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA        90
His Asp Phe Val His Gly Trp Ile Lys Val Pro Val Thr His Glu
                20                  25                  30

ACT CAG GAA GAG TGT CTT GGG ATG GCG GTG TTA GAC ATG ATG AGA       135
Thr Gln Glu Glu Cys Leu Gly Met Ala Val Leu Asp Met Met Arg
         35                  40                  45

ATA GCT AAG GAG AAA GAC CAG ACT CCA CTG GCT GTC TAT AAC TCT       180
Ile Ala Lys Glu Lys Asp Gln Thr Pro Leu Ala Val Tyr Asn Ser
                50                  55                  60

GTC AGC TAC AAG ACA TTC TTA CCA AAG TGC GTT CGA GCG AAG ATC       225
Val Ser Tyr Lys Thr Phe Leu Pro Lys Cys Val Arg Ala Lys Ile
 65                  70                  75

CAA GAC TAT CAC ATT TTA ACC CGG AAG CGA ATC AGG TAC AGA TTT       270
Gln Asp Tyr His Ile Leu Thr Arg Lys Arg Ile Arg Tyr Arg Phe
                80                  85                  90

CGC AGA TTC ATT CAG CAA TTC AGT CAA TGT AAA GCC ACT GCC AGG       315
Arg Arg Phe Ile Gln Gln Phe Ser Gln Cys Lys Ala Thr Ala Arg
         95                 100                 105

AAC CTA AAA CTT AAG TAT CTT ATA AAC CTG GAA ACC CTG CAG TCT       360
Asn Leu Lys Leu Lys Tyr Leu Ile Asn Leu Glu Thr Leu Gln Ser
                110                 115                 120

GCC TTC TAC ACA GAA CAG TTT GAA GTA AAA GAA TCT GCA AGA GGT       405
Ala Phe Tyr Thr Glu Gln Phe Glu Val Lys Glu Ser Ala Arg Gly
        125                 130                 135

CCT TCA GGT GAG GAG ATT TTT GCA ACC ATT ATA ATA ACT GGA AAC       450
Pro Ser Gly Glu Glu Ile Phe Ala Thr Ile Ile Ile Thr Gly Asn
                140                 145                 150

GGT GGA ATT CAG TGG TCA AGA GGG AAA CAT AAG GAA AGT GAG ACA       495
Gly Gly Ile Gln Trp Ser Arg Gly Lys His Lys Glu Ser Glu Thr
        155                 160                 165

CTG ACA GAA CAG GAC GTA CAG TTA TAT TGT GAT TTC CCT GAT ATT       540
Leu Thr Glu Gln Asp Val Gln Leu Tyr Cys Asp Phe Pro Asp Ile
                170                 175                 180

ATT GAT GTC AGT ATT AAG CAA GCA AAT CAG GAA TGC TCA ACT GAA       585
Ile Asp Val Ser Ile Lys Gln Ala Asn Gln Glu Cys Ser Thr Glu
        185                 190                 195

AGT AGA GTT GTG ACC GTC CAC AAG CAG GAC GGG AAG GTC TTG GAA       630
```

```
Ser Arg Val Val Thr Val His Lys Gln Asp Gly Lys Val Leu Glu
            200                 205                 210

ATA GAA CTT AGC TCA TTA AAA GAA GCC TTG TCA TTC GTG TCA TTA        675
Ile Glu Leu Ser Ser Leu Lys Glu Ala Leu Ser Phe Val Ser Leu
            215                 220                 225

ATT GAC GGG TAT TAC AGA CTA ACT GCG GAT GCA CAC CAT TAC CTC        720
Ile Asp Gly Tyr Tyr Arg Leu Thr Ala Asp Ala His His Tyr Leu
            230                 235                 240

TGC AAA GAG GTG GCT CCC CCA GCT GTG TTC GAG AAC ATA CAC AGC        765
Cys Lys Glu Val Ala Pro Pro Ala Val Phe Glu Asn Ile His Ser
            245                 250                 255

AAC TGC CAC GGC CCA ATT TCA ATG GAT TTT GCC ATC AGC AAA CTA        810
Asn Cys His Gly Pro Ile Ser Met Asp Phe Ala Ile Ser Lys Leu
            260                 265                 270

AAG AAG GCA GGA AAC CAG ACT GGA CTG TAT GTA CTT CGA TGT AGC        855
Lys Lys Ala Gly Asn Gln Thr Gly Leu Tyr Val Leu Arg Cys Ser
            275                 280                 285

CCT AAG GAC TTC AAC AAA TAC TTC CTG ACC TTT GCC GTT GAG CGA        900
Pro Lys Asp Phe Asn Lys Tyr Phe Leu Thr Phe Ala Val Glu Arg
            290                 295                 300

GAA AAT GTT ATT GAA TAT AAA CAC TGT TTG ATT ACA AAG AAT GAG        945
Glu Asn Val Ile Glu Tyr Lys His Cys Leu Ile Thr Lys Asn Glu
            305                 310                 315

AAT GGA GAG TAC AAC CTC AGT GGG ACT AAG AGG AAC TTC AGT AGT        990
Asn Gly Glu Tyr Asn Leu Ser Gly Thr Lys Arg Asn Phe Ser Ser
            320                 325                 330

CTT AAG GAC CTT TTG AAT TGC TAC CAG ATG GAA ACT GTG CGC TCA       1035
Leu Lys Asp Leu Leu Asn Cys Tyr Gln Met Glu Thr Val Arg Ser
            335                 340                 345

GAC AGT ATC ATC TTC CAG TTC ACC AAA TGC TGT CCT CCA AAG CCG       1080
Asp Ser Ile Ile Phe Gln Phe Thr Lys Cys Cys Pro Pro Lys Pro
            350                 355                 360

AAA GAT AAA TCA AAC CTT CTT GTC TTC AGA ACA AAT GGT GTT TCT       1125
Lys Asp Lys Ser Asn Leu Leu Val Phe Arg Thr Asn Gly Val Ser
            365                 370                 375

GAT GTT CAG CTC TCA CCA ACA TTA CAG AGG CAT AAT AAT GTG AAT       1170
Asp Val Gln Leu Ser Pro Thr Leu Gln Arg His Asn Asn Val Asn
            380                 385                 390

CAA ATG GTG TTT CAC AAA ATC AGG AAT GAA GAT TTG ATA TTT AAT       1215
Gln Met Val Phe His Lys Ile Arg Asn Glu Asp Leu Ile Phe Asn
            395                 400                 405

GAA AGC CTT GGC CAA GGC ACT TTT ACA AAA ATA TTT AAA GGT GTA       1260
Glu Ser Leu Gly Gln Gly Thr Phe Thr Lys Ile Phe Lys Gly Val
            410                 415                 420

AGA AGA GAA GTT GGA GAT TAT GGT CAG CTG CAC GAA ACC GAA GTT       1305
Arg Arg Glu Val Gly Asp Tyr Gly Gln Leu His Glu Thr Glu Val
            425                 430                 435

CTT TTG AAA GTC CTA GAT AAA GCA CAT AGA AAC TAT TCA GAG TCT       1350
Leu Leu Lys Val Leu Asp Lys Ala His Arg Asn Tyr Ser Glu Ser
            440                 445                 450

TTC TTT GAA GCA GCA AGC ATG ATG AGT CAG CTT TCT CAC AAG CAT       1395
Phe Phe Glu Ala Ala Ser Met Met Ser Gln Leu Ser His Lys His
            455                 460                 465

TTG GTT TTG AAT TAT GGA GTA TGT GTC TGT GGA GAG GAG AAC ATT       1440
Leu Val Leu Asn Tyr Gly Val Cys Val Cys Gly Glu Glu Asn Ile
            470                 475                 480

TTG GTT CAA GAG TTT GTA AAA TTT GGA TCA CTG GAT ACA TAC CTG       1485
Leu Val Gln Glu Phe Val Lys Phe Gly Ser Leu Asp Thr Tyr Leu
            485                 490                 495

AAG AAG AAC AAA AAT TCT ATA AAT ATA TTA TGG AAA CTT GGA GTG       1530
```

|  |  |
|---|---|
| Lys Lys Asn Lys Asn Ser Ile Asn Ile Leu Trp Lys Leu Gly Val<br>500 505 510 | |
| GCG AAG CAG TTG GCA TGG GCC ATG CAC TTC CTC GAA GAA AAA TCC<br>Ala Lys Gln Leu Ala Trp Ala Met His Phe Leu Glu Glu Lys Ser<br>515 520 525 | 1575 |
| CTT ATT CAT GGG AAT GTG TGT GCT AAA AAT ATC CTG CTT ATC AGA<br>Leu Ile His Gly Asn Val Cys Ala Lys Asn Ile Leu Leu Ile Arg<br>530 535 540 | 1620 |
| GAA GAA GAC AGG AGA ACG GGG AAC CCA CCT TTC ATC AAA CTT AGT<br>Glu Glu Asp Arg Arg Thr Gly Asn Pro Pro Phe Ile Lys Leu Ser<br>545 550 555 | 1665 |
| GAT CCT GGC ATT AGC ATT ACA GTT CTA CCG AAG GAC ATT TCT TCC<br>Asp Pro Gly Ile Ser Ile Thr Val Leu Pro Lys Asp Ile Ser Ser<br>560 565 570 | 1710 |
| TGT TGT TTC CAA GTT CTT CAG GAG AGA ATA CCA TGG GTA CCA CCT<br>Cys Cys Phe Gln Val Leu Gln Glu Arg Ile Pro Trp Val Pro Pro<br>575 580 585 | 1755 |
| GAG TGC ATT GAG AAT CCT AAA AAT CTA ACT CTG GCA ACA GAC AAG<br>Glu Cys Ile Glu Asn Pro Lys Asn Leu Thr Leu Ala Thr Asp Lys<br>590 595 600 | 1800 |
| TGG AGC TTC GGG ACC ACT CTG TGG GAG ATC TGC AGT GGA GGA GAT<br>Trp Ser Phe Gly Thr Thr Leu Trp Glu Ile Cys Ser Gly Gly Asp<br>605 610 615 | 1845 |
| AAG CCC CTG AGT GCT CTG GAT TCT CAA AGA AAG CTG CAG TTC TAT<br>Lys Pro Leu Ser Ala Leu Asp Ser Gln Arg Lys Leu Gln Phe Tyr<br>620 625 630 | 1890 |
| GAA GAT AAG CAT CAG CTT CCT GCA CCC AAG TGG ACA GAG TTG GCA<br>Glu Asp Lys His Gln Leu Pro Ala Pro Lys Trp Thr Glu Leu Ala<br>635 640 645 | 1935 |
| AAC CTT ATA AAT AAT TGC ATG GAC TAT GAG CCA GAT TTC AGG CCT<br>Asn Leu Ile Asn Asn Cys Met Asp Tyr Glu Pro Asp Phe Arg Pro<br>650 655 660 | 1980 |
| GCT TTC AGA GCT GTC ATC CGT GAT CTT AAC AGC CTG TTT ACT CCA<br>Ala Phe Arg Ala Val Ile Arg Asp Leu Asn Ser Leu Phe Thr Pro<br>665 670 675 | 2025 |
| GAT TAT GAA CTA CTA ACA GAA AAT GAC ATG CTA CCA AAC ATG AGA<br>Asp Tyr Glu Leu Leu Thr Glu Asn Asp Met Leu Pro Asn Met Arg<br>680 685 690 | 2070 |
| ATA GGT GCC CTA GGG TTT TCT GGT GCT TTT GAA GAC AGG GAC CCT<br>Ile Gly Ala Leu Gly Phe Ser Gly Ala Phe Glu Asp Arg Asp Pro<br>695 700 705 | 2115 |
| ACA CAG TTT GAA GAG AGA CAC TTG AAG TTT CTA CAG CAG CTT GGC<br>Thr Gln Phe Glu Glu Arg His Leu Lys Phe Leu Gln Gln Leu Gly<br>710 715 720 | 2160 |
| AAA GGT AAC TTC GGG AGT GTG GAG ATG TGC CGC TAT GAC CCG CTG<br>Lys Gly Asn Phe Gly Ser Val Glu Met Cys Arg Tyr Asp Pro Leu<br>725 730 735 | 2205 |
| CAG GAC AAC ACT GGC GAG GTG GTC GCT GTG AAG AAA CTC CAG CAC<br>Gln Asp Asn Thr Gly Glu Val Val Ala Val Lys Lys Leu Gln His<br>740 745 750 | 2250 |
| AGC ACT GAA GAG CAC CTC CGA GAC TTT GAG AGG GAG ATC GAG ATC<br>Ser Thr Glu Glu His Leu Arg Asp Phe Glu Arg Glu Ile Glu Ile<br>755 760 765 | 2295 |
| CTG AAA TCC TTG CAG CAT GAC AAC ATC GTC AAG TAC AAG GGA GTG<br>Leu Lys Ser Leu Gln His Asp Asn Ile Val Lys Tyr Lys Gly Val<br>770 775 780 | 2340 |
| TGC TAC AGT GCG GGT CGG CGC AAC CTA AGA TTA ATT ATG GAA TAT<br>Cys Tyr Ser Ala Gly Arg Arg Asn Leu Arg Leu Ile Met Glu Tyr<br>785 790 795 | 2385 |
| TTA CCA TAT GGA AGT TTA CGA GAC TAT CTC CAA AAA CAT AAA GAA | 2430 |

```
                Leu Pro Tyr Gly Ser Leu Arg Asp Tyr Leu Gln Lys His Lys Glu
                                800                 805                 810

CGG ATA GAT CAC AAA AAA CTT CTT CAA TAC ACA TCT CAG ATA TGC               2475
Arg Ile Asp His Lys Lys Leu Leu Gln Tyr Thr Ser Gln Ile Cys
            815                 820                 825

AAG GGC ATG GAA TAT CTT GGT ACA AAA AGG TAT ATC CAC AGG GAC               2520
Lys Gly Met Glu Tyr Leu Gly Thr Lys Arg Tyr Ile His Arg Asp
                830                 835                 840

CTG GCA ACA AGG AAC ATA TTG GTG GAA AAT GAG AAC AGG GTT AAA               2565
Leu Ala Thr Arg Asn Ile Leu Val Glu Asn Glu Asn Arg Val Lys
            845                 850                 855

ATA GGA GAC TTC GGA TTA ACC AAA GTC TTG CCG CAG GAC AAA GAA               2610
Ile Gly Asp Phe Gly Leu Thr Lys Val Leu Pro Gln Asp Lys Glu
                860                 865                 870

TAC TAC AAA GTA AAG GAG CCA GGG GAA AGC CCC ATA TTC TGG TAC               2655
Tyr Tyr Lys Val Lys Glu Pro Gly Glu Ser Pro Ile Phe Trp Tyr
            875                 880                 885

GCA CCT GAA TCC TTG ACG GAG AGC AAG TTT TCT GTG GCC TCA GAT               2700
Ala Pro Glu Ser Leu Thr Glu Ser Lys Phe Ser Val Ala Ser Asp
                890                 895                 900

GTG TGG AGC TTT GGA GTG GTT CTA TAC GAA CTT TTC ACA TAC ATC               2745
Val Trp Ser Phe Gly Val Val Leu Tyr Glu Leu Phe Thr Tyr Ile
            905                 910                 915

GAG AAG AGT AAA AGT CCA CCC GTG GAA TTT ATG CGA ATG ATT GGC               2790
Glu Lys Ser Lys Ser Pro Pro Val Glu Phe Met Arg Met Ile Gly
                920                 925                 930

AAT GAT AAA CAA GGG CAA ATG ATT GTG TTC CAT TTG ATA GAG CTA               2835
Asn Asp Lys Gln Gly Gln Met Ile Val Phe His Leu Ile Glu Leu
            935                 940                 945

CTG AAG AGC AAC GGA AGA TTG CCA AGG CCA GAA GGA TGC CCA GAT               2880
Leu Lys Ser Asn Gly Arg Leu Pro Arg Pro Glu Gly Cys Pro Asp
                950                 955                 960

GAG ATT TAT GTG ATC ATG ACA GAG TGC TGG AAC AAC AAT GTG AGC               2925
Glu Ile Tyr Val Ile Met Thr Glu Cys Trp Asn Asn Asn Val Ser
            965                 970                 975

CAG CGT CCC TCC TTC AGG GAC CTT TCC TTC GGG TGG ATC AAA TCC               2970
Gln Arg Pro Ser Phe Arg Asp Leu Ser Phe Gly Trp Ile Lys Ser
                980                 985                 990

GGG ACA GTA TAGCTGCGTG AAAGAGATGG CCTTACTCAG AGACCAAGCA                   3019
Gly Thr Val

GACTTCCAGA ACCAGAACAA AGCTCTGTAG CCTTGTGTCT ACACATCCTT                    3069

ATCATGACGC TAGCTAGGCA GAAAGAAAAC TGTGACGCCG TCTGCTCAAA                    3119

AGCTTTGGAA AACGCCGTGC AGGTTTGTTT CATCACCATC TGTAAAAACC                    3169

ACTGCTCAAG TCTGGCAGCA TGCTTGTGGG CTGATGCATG GAGCTCACCA                    3219

CAGAGTCTCT GCATCTCCTC TGACAGAAGA AGAAAAATAG ACAATTTTCA                    3269

ACTCACTTTT TTGAGAAATG GAAAAAAATT ATAATGTAAA TTTTTCAGTG                    3319

TAGGAAATAC ACAGAACATA CATGTACAGT TTTTACCACG TGGAGTGTAT                    3369

AATACTTTGG CCTCTTGTGT GATTTACATG AGGGCTGATG TTTGTTAATG                    3419

TTTTCTAATT TTTCCATAGG TGATCTATAA TAACTTCATG ATACAAATTA                    3469

AAATGCTCAG AAAATTAAAA AAAAAA                                              3495

(2) INFORMATION FOR SEQ ID NO:3:

(i) SEQUENCE CHARACTERISTICS:
        (A) LENGTH: 6 amino acid residues
        (B) TYPE:  amino acid
```

(D) TOPOLOGY:  linear (ix) FEATURE:
         (D) OTHER INFORMATION:  Xaa in positions 2, 4 and 5 is
                                 unknown.

(xi) SEQUENCE DESCRIPTION:  SEQ ID NO: 3:

Gly Xaa Gly Xaa Xaa Gly
                  5

(2) INFORMATION FOR SEQ ID NO:4:

(i) SEQUENCE CHARACTERISTICS:
        (A) LENGTH: 16 amino acid residues
        (B) TYPE:  amino acid
        (D) TOPOLOGY:  linear (xi) SEQUENCE DESCRIPTION:  SEQ ID NO: 4:

Thr Ser Phe Gln Asn Leu Ile Glu Cys Phe Glu Ala Leu Leu Lys Cys
                  5                  10                  15

(2) INFORMATION FOR SEQ ID NO:5:

(i) SEQUENCE CHARACTERISTICS:
        (A) LENGTH: 21 base pairs
        (B) TYPE:  nucleic acid
        (C) STRANDEDNESS:  single
        (D) TOPOLOGY:  linear (xi) SEQUENCE DESCRIPTION:  SEQ ID NO: 5:

TACACCTTTA AATATTTTTG T                                              21

(2) INFORMATION FOR SEQ ID NO:6:

(i) SEQUENCE CHARACTERISTICS:
        (A) LENGTH: 17 base pairs
        (B) TYPE:  nucleic acid
        (C) STRANDEDNESS:  single
        (D) TOPOLOGY:  linear (xi) SEQUENCE DESCRIPTION:  SEQ ID NO: 6:

CTCGAGTCGA CGAATTC                                                   17

(2) INFORMATION FOR SEQ ID NO:7:

(i) SEQUENCE CHARACTERISTICS:
        (A) LENGTH: 20 base pairs
        (B) TYPE:  nucleic acid
        (C) STRANDEDNESS:  single
        (D) TOPOLOGY:  linear (xi) SEQUENCE DESCRIPTION:  SEQ ID NO: 7:

CTTGCTTAAT ACTGACATCA                                                20

(2) INFORMATION FOR SEQ ID NO:8:

(i) SEQUENCE CHARACTERISTICS:
        (A) LENGTH: 20 base pairs
        (B) TYPE:  nucleic acid
        (C) STRANDEDNESS:  single
        (D) TOPOLOGY:  linear (xi) SEQUENCE DESCRIPTION:  SEQ ID NO: 8:

CTTGCTTAAT ACTGACATCA                                                20

(2) INFORMATION FOR SEQ ID NO:9:

(i) SEQUENCE CHARACTERISTICS:

(A) LENGTH: 9 base pairs
            (B) TYPE: nucleic acid
            (C) STRANDEDNESS: single
            (D) TOPOLOGY: linear (xi) SEQUENCE DESCRIPTION: SEQ ID NO: 9:

TAAATGCAG                                                                            9

(2) INFORMATION FOR SEQ ID NO:10:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (xi) SEQUENCE DESCRIPTION: SEQ ID NO: 10:

GCCATGGCT                                                                            9

(2) INFORMATION FOR SEQ ID NO:11:

(i) SEQUENCE CHARACTERISTICS:
            (A) LENGTH: 8 amino acid residues
            (B) TYPE: amino acid
            (D) TOPOLOGY: linear (xi) SEQUENCE DESCRIPTION: SEQ ID NO: 11:

Gly Leu Tyr Val Leu Arg Trp Ser
                              8

(2) INFORMATION FOR SEQ ID NO:12:

(i) SEQUENCE CHARACTERISTICS:
            (A) LENGTH: 7 amino acid residues
            (B) TYPE: amino acid
            (D) TOPOLOGY: linear (xi) SEQUENCE DESCRIPTION: SEQ ID NO: 12:

Val Asp Gly Tyr Phe Arg Ile
              5

(2) INFORMATION FOR SEQ ID NO: 13:

(i) SEQUENCE CHARACTERISTICS:
            (A) LENGTH: 47 amino acids
            (B) TYPE: amino acid
            (D) TOPOLOGY: linear (xi) SEQUENCE DESCRIPTION: SEQ ID NO: 13:

Lys Ile Gly Glu Gly Thr Tyr Gly Val Val Tyr Lys Gly Arg His
              5                   10                  15

Lys Thr Thr Gly Gln Val Val Ala Met Lys Lys Ile Arg Leu Glu
              20                  25                  30

Ser Glu Glu Glu Gly Val Pro Ser Thr Ala Ile Arg Glu Ile Ser
              35                  40                  45

Leu Leu (2) INFORMATION FOR SEQ ID NO: 14:

(i) SEQUENCE CHARACTERISTICS:
            (A) LENGTH: 82 amino acids
            (B) TYPE: amino acid
            (D) TOPOLOGY: linear (xi) SEQUENCE DESCRIPTION: SEQ ID NO: 14:

Val Phe Cys His Ser Arg Arg Val Leu His Arg Asp Leu Lys Pro

```
                     5              10                  15
Gln Asn Leu Leu Ile Asp Asp Lys Gly Thr Ile Lys Leu Ala Asp
                 20                  25                  30

Phe Gly Leu Ala Arg Ala Phe Gly Ile Pro Ile Arg Val Tyr Thr
                 35                  40                  45

His Glu Val Val Thr Leu Trp Tyr Arg Ser Pro Glu Val Leu Leu
                 50                  55                  60

Gly Ser Ala Arg Tyr Ser Thr Pro Val Asp Ile Trp Ser Ile Gly
                 65                  70                  75

Thr Ile Phe Ala Glu Leu Ala
                 80

(2) INFORMATION FOR SEQ ID NO: 15:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO: 15:

Leu Ala Ser His His Val Lys Asn Leu Asp Glu Asn Gly Leu Asp
                 5                   10                  15

Leu Leu Ser Lys Met Leu Ile Tyr Asp Pro Ala Lys Arg Ile Ser
                 20                  25                  30

(2) INFORMATION FOR SEQ ID NO: 16:

(i) SEQUENCE CHARACTERISTICS:
        (A) LENGTH: 601 amino acids
        (B) TYPE: amino acid
        (D) TOPOLOGY: linear (xi) SEQUENCE DESCRIPTION: SEQ ID NO: 16:

Val Phe His Lys Ile Arg Asn Glu Asp Leu Ile Phe Asn Glu Ser
                 5                   10                  15

Leu Gly Gln Gly Thr Phe Thr Lys Ile Phe Lys Gly Val Arg Arg
                 20                  25                  30

Glu Val Gly Asp Tyr Gly Gln Leu His Glu Thr Glu Val Leu Leu
                 35                  40                  45

Lys Val Leu Asp Lys Ala His Arg Asn Tyr Ser Glu Ser Phe Phe
                 50                  55                  60

Glu Ala Ala Ser Met Met Ser Gln Leu Ser His Lys His Leu Val
                 65                  70                  75

Leu Asn Tyr Gly Val Cys Val Cys Gly Glu Glu Asn Ile Leu Val
                 80                  85                  90

Gln Glu Phe Val Lys Phe Gly Ser Leu Asp Thr Tyr Leu Lys Lys
                 95                  100                 105

Asn Lys Asn Ser Ile Asn Ile Leu Trp Lys Leu Gly Val Ala Lys
                 110                 115                 120

Gln Leu Ala Trp Ala Met His Phe Leu Glu Glu Lys Ser Leu Ile
                 125                 130                 135

His Gly Asn Val Cys Ala Lys Asn Ile Leu Leu Ile Arg Glu Glu
                 140                 145                 150

Asp Arg Arg Thr Gly Asn Pro Pro Phe Ile Lys Leu Ser Asp Pro
                 155                 160                 165

Gly Ile Ser Ile Thr Val Leu Pro Lys Asp Ile Ser Ser Cys Cys
                 170                 175                 180

Phe Gln Val Leu Gln Glu Arg Ile Pro Trp Val Pro Pro Glu Cys
```

```
                  185                 190                 195
Ile Glu Asn Pro Lys Asn Leu Thr Leu Ala Thr Asp Lys Trp Ser
                200                 205                 210
Phe Gly Thr Thr Leu Trp Glu Ile Cys Ser Gly Gly Asp Lys Pro
                215                 220                 225
Leu Ser Ala Leu Asp Ser Gln Arg Lys Leu Gln Phe Tyr Glu Asp
                230                 235                 240
Lys His Gln Leu Pro Ala Pro Lys Trp Thr Glu Leu Ala Asn Leu
                245                 250                 255
Ile Asn Asn Cys Met Asp Tyr Glu Pro Asp Phe Arg Pro Ala Phe
                260                 265                 270
Arg Ala Val Ile Arg Asp Leu Asn Ser Leu Phe Thr Pro Asp Tyr
                275                 280                 285
Glu Leu Leu Thr Glu Asn Asp Met Leu Pro Asn Met Arg Ile Gly
                290                 295                 300
Ala Leu Gly Phe Ser Gly Ala Phe Glu Asp Arg Asp Pro Thr Gln
                305                 310                 315
Phe Glu Glu Arg His Leu Lys Phe Leu Gln Gln Leu Gly Lys Gly
                320                 325                 330
Asn Phe Gly Ser Val Glu Met Cys Arg Tyr Asp Pro Leu Gln Asp
                335                 340                 345
Asn Thr Gly Glu Val Val Ala Val Lys Lys Leu Gln His Ser Thr
                350                 355                 360
Glu Glu His Leu Arg Asp Phe Glu Arg Glu Ile Glu Ile Leu Lys
                365                 370                 375
Ser Leu Gln His Asp Asn Ile Val Lys Tyr Lys Gly Val Cys Tyr
                380                 385                 390
Ser Ala Gly Arg Arg Asn Leu Arg Leu Ile Met Glu Tyr Leu Pro
                395                 400                 405
Tyr Gly Ser Leu Arg Asp Tyr Leu Gln Lys His Lys Glu Arg Ile
                410                 415                 420
Asp His Lys Lys Leu Leu Gln Tyr Thr Ser Gln Ile Cys Lys Gly
                425                 430                 435
Met Glu Tyr Leu Gly Thr Lys Arg Tyr Ile His Arg Asp Leu Ala
                440                 445                 450
Thr Arg Asn Ile Leu Val Glu Asn Glu Asn Arg Val Lys Ile Gly
                455                 460                 465
Asp Phe Gly Leu Thr Lys Val Leu Pro Gln Asp Lys Glu Tyr Tyr
                470                 475                 480
Lys Val Lys Glu Pro Gly Glu Ser Pro Ile Phe Trp Tyr Ala Pro
                485                 490                 495
Glu Ser Leu Thr Glu Ser Lys Phe Ser Val Ala Ser Asp Val Trp
                500                 505                 510
Ser Phe Gly Val Val Leu Tyr Glu Leu Phe Thr Tyr Ile Glu Lys
                515                 520                 525
Ser Lys Ser Pro Pro Val Glu Phe Met Arg Met Ile Gly Asn Asp
                530                 535                 540
Lys Gln Gly Gln Met Ile Val Phe His Leu Ile Glu Leu Leu Lys
                545                 550                 555
Ser Asn Gly Arg Leu Pro Arg Pro Glu Gly Cys Pro Asp Glu Ile
                560                 565                 570
Tyr Val Ile Met Thr Glu Cys Trp Asn Asn Asn Val Ser Gln Arg
                575                 580                 585
```

-continued

```
Pro Ser Phe Arg Asp Leu Ser Phe Gly Trp Ile Lys Ser Gly Thr
            590                 595                 600

Val
```

(2) INFORMATION FOR SEQ ID NO: 17:

(i) SEQUENCE CHARACTERISTICS:
       (A) LENGTH: 581 amino acids
       (B) TYPE: amino acid
       (D) TOPOLOGY: linear (xi) SEQUENCE DESCRIPTION: SEQ ID NO: 17:

```
Ser Phe Asp Arg Ile Leu Lys Lys Asp Leu Val Gln Gly Glu His
              5                  10                  15

Leu Gly Arg Gly Thr Arg Thr His Ile Tyr Ser Gly Thr Leu Met
             20                  25                  30

Asp Tyr Lys Asp Asp Glu Gly Thr Ser Glu Glu Lys Lys Ile Lys
             35                  40                  45

Val Ile Leu Lys Val Leu Asp Pro Ser His Arg Asp Ile Ser Leu
             50                  55                  60

Ala Phe Phe Glu Ala Ala Ser Met Met Arg Gln Val Ser His Lys
             65                  70                  75

His Ile Val Tyr Leu Tyr Gly Val Cys Val Arg Asp Val Glu Asn
             80                  85                  90

Ile Met Val Glu Glu Phe Val Glu Gly Gly Pro Leu Asp Leu Phe
             95                 100                 105

Met His Arg Lys Ser Asp Val Leu Thr Thr Pro Trp Lys Phe Lys
            110                 115                 120

Val Ala Lys Gln Leu Ala Ser Ala Leu Ser Tyr Leu Glu Asp Lys
            125                 130                 135

Asp Leu Val His Gly Asn Val Cys Thr Lys Asn Leu Leu Leu Ala
            140                 145                 150

Arg Glu Gly Ile Asp Ser Glu Cys Gly Pro Phe Ile Lys Leu Ser
            155                 160                 165

Asp Pro Gly Ile Pro Ile Thr Val Leu Ser Arg Gln Glu Cys Ile
            170                 175                 180

Glu Arg Ile Pro Trp Ile Ala Pro Glu Cys Val Glu Asp Ser Lys
            185                 190                 195

Asn Leu Ser Val Ala Ala Asp Lys Trp Ser Phe Gly Thr Thr Leu
            200                 205                 210

Trp Glu Ile Cys Tyr Asn Gly Glu Ile Pro Leu Lys Asp Lys Thr
            215                 220                 225

Leu Ile Glu Lys Glu Arg Phe Tyr Glu Ser Arg Cys Arg Pro Val
            230                 235                 240

Thr Pro Ser Cys Lys Glu Leu Ala Asp Leu Met Thr Arg Cys Met
            245                 250                 255

Asn Tyr Asp Pro Asn Gln Arg Pro Phe Phe Arg Ala Ile Met Arg
            260                 265                 270

Asp Ile Asn Lys Leu Glu Glu Gln Asn Pro Asp Ile Val Ser Arg
            275                 280                 285

Lys Lys Asn Gln Pro Thr Glu Val Asp Pro Thr His Phe Thr Lys
            290                 295                 300

Arg Phe Leu Lys Arg Ile Arg Asp Leu Gly Glu Gly His Phe Gly
            305                 310                 315

Lys Val Glu Leu Cys Arg Tyr Asp Pro Glu Asp Asn Thr Gly Glu
            320                 325                 330
```

```
Gln Val Ala Val Lys Ser Leu Lys Pro Glu Ser Gly Gly Asn His
            335                 340                 345

Ile Ala Asp Leu Lys Lys Glu Ile Glu Ile Leu Arg Asn Leu Tyr
            350                 355                 360

His Glu Asn Ile Val Lys Tyr Lys Gly Ile Cys Thr Glu Asp Gly
            365                 370                 375

Gly Asn Gly Ile Lys Leu Ile Met Glu Phe Leu Pro Ser Gly Ser
            380                 385                 390

Leu Lys Glu Tyr Leu Pro Lys Asn Lys Asn Lys Ile Asn Leu Lys
            395                 400                 405

Gln Gln Leu Lys Tyr Ala Val Gln Ile Cys Lys Gly Met Asp Tyr
            410                 415                 420

Leu Gly Ser Arg Gln Tyr Val His Arg Asp Leu Ala Ala Arg Asn
            425                 430                 435

Val Leu Val Glu Ser Glu His Gln Val Lys Ile Gly Asp Phe Gly
            440                 445                 450

Leu Thr Lys Ala Ile Glu Thr Asp Lys Glu Tyr Tyr Thr Val Lys
            455                 460                 465

Asp Asp Arg Asp Ser Pro Val Phe Trp Tyr Ala Pro Glu Cys Leu
            470                 475                 480

Met Gln Ser Lys Phe Tyr Ile Ala Ser Asp Val Trp Ser Phe Gly
            485                 490                 495

Val Thr Leu His Glu Leu Leu Thr Tyr Cys Asp Ser Asp Ser Ser
            500                 505                 510

Pro Met Ala Leu Phe Leu Lys Met Ile Gly Pro Thr His Gly Gln
            515                 520                 525

Met Thr Val Thr Arg Leu Val Asn Thr Leu Lys Glu Gly Lys Arg
            530                 535                 540

Leu Pro Cys Pro Pro Asn Cys Pro Asp Glu Val Tyr Gln Leu Met
            545                 550                 555

Arg Lys Cys Trp Glu Phe Gln Pro Ser Asn Arg Thr Ser Phe Gln
            560                 565                 570

Asn Leu Ile Glu Gly Phe Glu Ala Leu Leu Lys
            575                 580
```

(2) INFORMATION FOR SEQ ID NO: 18:

(i) SEQUENCE CHARACTERISTICS:
        (A) LENGTH: 1132 amino acids
        (B) TYPE: amino acid
        (D) TOPOLOGY: linear (xi) SEQUENCE DESCRIPTION: SEQ ID NO: 18:

```
Met Gln Tyr Leu Asn Ile Lys Glu Asp Cys Asn Ala Met Ala Phe
              5                  10                  15

Cys Ala Lys Met Arg Ser Ser Lys Lys Thr Glu Val Asn Leu Glu
             20                  25                  30

Ala Pro Glu Pro Gly Val Glu Val Ile Phe Tyr Leu Ser Asp Arg
             35                  40                  45

Glu Pro Leu Arg Leu Gly Ser Gly Glu Tyr Thr Ala Glu Glu Leu
             50                  55                  60

Cys Ile Arg Ala Ala Gln Ala Cys Arg Ile Ser Pro Leu Cys His
             65                  70                  75

Asn Leu Phe Ala Leu Tyr Asp Glu Asn Thr Lys Leu Trp Tyr Ala
             80                  85                  90
```

-continued

```
Pro Asn Arg Thr Ile Thr Val Asp Asp Lys Met Ser Leu Arg Leu
             95                 100                 105

His Tyr Arg Met Arg Phe Tyr Phe Thr Asn Trp His Gly Thr Asn
            110                 115                 120

Asp Asn Glu Gln Ser Val Trp Arg His Ser Pro Lys Lys Gln Lys
            125                 130                 135

Asn Gly Tyr Glu Lys Lys Ile Pro Asp Ala Thr Pro Leu Leu
            140                 145                 150

Asp Ala Ser Ser Leu Glu Tyr Leu Phe Ala Gln Gly Gln Tyr Asp
            155                 160                 165

Leu Val Lys Cys Leu Ala Pro Ile Arg Asp Pro Lys Thr Glu Gln
            170                 175                 180

Asp Gly His Asp Ile Glu Asn Glu Cys Leu Gly Met Ala Val Leu
            185                 190                 195

Ala Ile Ser His Tyr Ala Met Met Lys Lys Met Gln Leu Pro Glu
            200                 205                 210

Leu Pro Lys Asp Ile Ser Tyr Lys Arg Tyr Ile Pro Glu Thr Leu
            215                 220                 225

Asn Lys Ser Ile Arg Gln Arg Asn Leu Leu Thr Arg Met Arg Ile
            230                 235                 240

Asn Asn Val Phe Lys Asp Phe Leu Lys Glu Phe Asn Asn Lys Thr
            245                 250                 255

Ile Cys Asp Ser Ser Val Ser Thr His Asp Leu Lys Val Lys Tyr
            260                 265                 270

Leu Ala Thr Leu Glu Thr Leu Thr Lys His Tyr Gly Ala Glu Ile
            275                 280                 285

Phe Glu Thr Ser Met Leu Leu Ile Ser Ser Gly Asn Glu Met Asn
            290                 295                 300

Trp Phe His Ser Asn Asp Gly Gly Asn Val Leu Tyr Tyr Glu Val
            305                 310                 315

Met Val Thr Gly Asn Leu Gly Ile Gln Trp Arg His Lys Pro Asn
            320                 325                 330

Val Val Ser Val Glu Lys Glu Lys Asn Lys Leu Lys Arg Lys Lys
            335                 340                 345

Leu Glu Asn Lys Asp Lys Lys Asp Glu Glu Lys Asn Lys Ile Arg
            350                 355                 360

Glu Glu Trp Asn Asn Phe Ser Phe Phe Pro Glu Ile Thr His Ile
            365                 370                 375

Val Ile Lys Glu Ser Val Val Ser Ile Asn Lys Gln Asp Asn Lys
            380                 385                 390

Lys Met Glu Leu Lys Leu Ser Ser His Glu Ala Leu Ser Phe
            395                 400                 405

Val Ser Leu Val Asp Gly Tyr Phe Arg Leu Thr Ala Asp Ala His
            410                 415                 420

His Tyr Leu Cys Thr Asp Val Ala Pro Pro Leu Ile Val His Asn
            425                 430                 435

Ile Gln Asn Gly Cys His Gly Pro Ile Cys Glu Tyr Ala Ile Asn
            440                 445                 450

Lys Leu Arg Gln Glu Gly Ser Glu Glu Gly Met Tyr Val Leu Arg
            455                 460                 465

Trp Ser Cys Thr Asp Phe Asp Asn Ile Leu Met Thr Val Thr Cys
            470                 475                 480

Phe Glu Lys Ser Glu Gln Val Gln Gly Ala Gln Lys Gln Phe Lys
            485                 490                 495
```

```
Asn Phe Gln Ile Glu Val Gln Lys Gly Arg Tyr Ser Leu His Gly
                500                 505                 510
Ser Asp Arg Ser Phe Pro Ser Leu Gly Asp Leu Met Ser His Leu
            515                 520                 525
Lys Lys Gln Ile Leu Arg Thr Asp Asn Ile Ser Phe Met Leu Lys
            530                 535                 540
Arg Cys Cys Gln Pro Lys Pro Arg Glu Ile Ser Asn Leu Leu Val
            545                 550                 555
Ala Thr Lys Lys Ala Gln Glu Trp Gln Pro Val Tyr Pro Met Ser
            560                 565                 570
Gln Leu Ser Phe Asp Arg Ile Leu Lys Lys Asp Leu Val Gln Gly
            575                 580                 585
Glu His Leu Gly Arg Gly Thr Arg Thr His Ile Tyr Ser Gly Thr
            590                 595                 600
Leu Met Asp Tyr Lys Asp Asp Glu Gly Thr Ser Glu Glu Lys Lys
            605                 610                 615
Ile Lys Val Ile Leu Lys Val Leu Asp Pro Ser His Arg Asp Ile
            620                 625                 630
Ser Leu Ala Phe Phe Glu Ala Ala Ser Met Met Arg Gln Val Ser
            635                 640                 645
His Lys His Ile Val Tyr Leu Tyr Gly Val Cys Val Arg Asp Val
            650                 655                 660
Glu Asn Ile Met Val Glu Glu Phe Val Glu Gly Gly Pro Leu Asp
            665                 670                 675
Leu Phe Met His Arg Lys Ser Asp Val Leu Thr Thr Pro Trp Lys
            680                 685                 690
Phe Lys Val Ala Lys Gln Leu Ala Ser Ala Leu Ser Tyr Leu Glu
            695                 700                 705
Asp Lys Asp Leu Val His Gly Asn Val Cys Thr Lys Asn Leu Leu
            710                 715                 720
Leu Ala Arg Glu Gly Ile Asp Ser Glu Cys Gly Pro Phe Ile Lys
            725                 730                 735
Leu Ser Asp Pro Gly Ile Pro Ile Thr Val Leu Ser Arg Gln Glu
            740                 745                 750
Cys Ile Glu Arg Ile Pro Trp Ile Ala Pro Glu Cys Val Glu Asp
            755                 760                 765
Ser Lys Asn Leu Ser Val Ala Ala Asp Lys Trp Ser Phe Gly Thr
            770                 775                 780
Thr Leu Trp Glu Ile Cys Tyr Asn Gly Glu Ile Pro Leu Lys Asp
            785                 790                 795
Lys Thr Leu Ile Glu Lys Glu Arg Phe Tyr Glu Ser Arg Cys Arg
            800                 805                 810
Pro Val Thr Pro Ser Cys Lys Glu Leu Ala Asp Leu Met Thr Arg
            815                 820                 825
Cys Met Asn Tyr Asp Pro Asn Gln Arg Pro Phe Phe Arg Ala Ile
            830                 835                 840
Met Arg Asp Ile Asn Lys Leu Glu Glu Gln Asn Pro Asp Ile Val
            845                 850                 855
Ser Arg Lys Lys Asn Gln Pro Thr Glu Val Asp Pro Thr His Phe
            860                 865                 870
Lys Arg Phe Leu Lys Arg Ile Arg Asp Leu Gly Glu Gly His Phe
            875                 880                 885
Gly Lys Val Glu Leu Cys Arg Tyr Asp Pro Glu Asp Asn Thr Gly
```

890                 895                 900
Glu Gln Val Ala Val Lys Ser Leu Lys Pro Glu Ser Gly Gly Asn
                 905                 910                 915
His Ile Ala Asp Leu Lys Lys Glu Ile Glu Ile Leu Arg Asn Leu
                 920                 925                 930
Tyr His Glu Asn Ile Val Lys Tyr Lys Gly Ile Cys Thr Glu Asp
                 935                 940                 945
Gly Gly Asn Gly Ile Lys Leu Ile Met Glu Phe Leu Pro Ser Gly
                 950                 955                 960
Ser Leu Lys Glu Tyr Leu Pro Lys Asn Lys Asn Lys Ile Asn Leu
                 965                 970                 975
Lys Gln Gln Leu Lys Tyr Ala Val Gln Ile Cys Lys Gly Met Asp
                 980                 985                 990
Tyr Leu Gly Ser Arg Gln Tyr Val His Arg Asp Leu Ala Ala Arg
                 995                 1000                1005
Asn Val Leu Val Glu Ser His Gln Val Lys Ile Gly Asp Phe
                 1010                1015                1020
Gly Leu Thr Lys Ala Ile Glu Thr Asp Lys Glu Tyr Tyr Thr Val
                 1025                1030                1035
Lys Asp Asp Arg Asp Ser Pro Val Phe Trp Tyr Ala Pro Glu Cys
                 1040                1045                1050
Leu Met Gln Ser Lys Phe Tyr Ile Ala Ser Asp Val Trp Ser Phe
                 1055                1060                1065
Gly Val Thr Leu His Glu Leu Leu Thr Tyr Cys Asp Ser Asp Ser
                 1070                1075                1080
Ser Pro Met Ala Leu Phe Leu Lys Met Ile Gly Pro Thr His Gly
                 1085                1090                1095
Gln Met Thr Val Thr Arg Leu Val Asn Thr Leu Lys Glu Gly Lys
                 1100                1105                1110
Arg Leu Pro Cys Pro Pro Asn Cys Pro Asp Glu Val Tyr Gln Leu
                 1115                1120                1125
Met Arg Lys Cys Trp Glu Phe
                 1130

(2) INFORMATION FOR SEQ ID NO: 19:

(i) SEQUENCE CHARACTERISTICS:
        (A) LENGTH: 971 amino acids
        (B) TYPE: amino acid
        (D) TOPOLOGY: linear (xi) SEQUENCE DESCRIPTION: SEQ ID NO: 19:

Leu Leu Asp Asp Phe Val Met Ser Tyr Leu Ser Pro Gln Trp Arg
                 5                   10                  15
His Asp Phe Val His Gly Trp Ile Lys Val Pro Val Thr His Glu
                 20                  25                  30
Thr Gln Glu Glu Cys Leu Gly Met Ala Val Leu Asp Met Met Arg
                 35                  40                  45
Ile Ala Lys Glu Lys Asp Gln Thr Pro Leu Ala Val Tyr Asn Ser
                 50                  55                  60
Val Ser Tyr Lys Thr Phe Leu Pro Lys Cys Val Arg Ala Lys Ile
                 65                  70                  75
Gln Asp Tyr His Ile Leu Thr Arg Lys Arg Ile Arg Tyr Arg Phe
                 80                  85                  90
Arg Arg Phe Ile Gln Gln Phe Ser Gln Cys Lys Ala Thr Ala Arg
                 95                  100                 105

```
Asn Leu Lys Leu Lys Tyr Leu Ile Asn Leu Glu Thr Leu Gln Ser
            110                 115                 120

Ala Phe Tyr Thr Glu Gln Phe Glu Val Lys Glu Ser Ala Arg Gly
            125                 130                 135

Pro Ser Gly Glu Glu Ile Phe Ala Thr Ile Ile Thr Gly Asn
            140                 145                 150

Gly Gly Ile Gln Trp Ser Arg Gly Lys His Lys Glu Ser Glu Thr
            155                 160                 165

Leu Thr Glu Gln Asp Leu Gln Leu Tyr Cys Asp Phe Pro Asp Ile
            170                 175                 180

Ile Asp Val Ser Ile Lys Gln Ala Asn Gln Glu Cys Ser Thr Glu
            185                 190                 195

Ser Arg Ile Val Thr Val His Lys Gln Asp Gly Glu Val Leu Glu
            200                 205                 210

Ile Glu Leu Ser Ser Leu Lys Glu Ala Leu Ser Phe Val Ser Leu
            215                 220                 225

Ile Asp Gly Tyr Tyr Arg Leu Thr Ala Asp Ala His His Tyr Leu
            230                 235                 240

Cys Lys Glu Val Ala Pro Pro Ala Val Leu Glu Asn Ile His Ser
            245                 250                 255

Asn Cys His Gly Pro Ile Ser Met Asp Phe Ala Ile Ser Lys Leu
            260                 265                 270

Lys Lys Ala Gly Asn Gln Thr Gly Leu Tyr Val Leu Arg Cys Ser
            275                 280                 285

Pro Lys Asp Phe Asn Lys Tyr Phe Leu Thr Phe Ala Val Glu Arg
            290                 295                 300

Glu Asn Val Ile Glu Tyr Lys His Cys Leu Ile Thr Lys Asn Glu
            305                 310                 315

Asn Gly Glu Tyr Asn Leu Ser Gly Thr Lys Arg Asn Phe Ser Ser
            320                 325                 330

Leu Lys Asp Leu Leu Asn Cys Tyr Gln Met Glu Thr Val Arg Ser
            335                 340                 345

Asp Ser Ile Ile Phe Gln Phe Thr Lys Cys Cys Pro Pro Lys Pro
            350                 355                 360

Lys Asp Lys Ser Asn Leu Leu Val Phe Arg Thr Asn Gly Val Ser
            365                 370                 375

Asp Val Gln Leu Ser Pro Thr Leu Gln Arg His Asn Asn Val Asn
            380                 385                 390

Gln Met Val Phe His Lys Ile Arg Asn Glu Asp Leu Ile Phe Asn
            395                 400                 405

Glu Ser Leu Gly Gln Gly Thr Phe Thr Lys Ile Phe Lys Gly Val
            410                 415                 420

Arg Arg Glu Val Gly Asp Tyr Gly Gln Leu His Glu Thr Glu Val
            425                 430                 435

Leu Leu Lys Val Leu Asp Lys Ala His Arg Asn Tyr Ser Glu Ser
            440                 445                 450

Phe Phe Glu Ala Ala Ser Met Met Ser Gln Leu Ser His Lys His
            455                 460                 465

Leu Val Leu Asn Tyr Gly Val Cys Val Cys Gly Glu Glu Asn Ile
            470                 475                 480

Leu Val Gln Glu Phe Val Lys Phe Gly Ser Leu Asp Thr Tyr Leu
            485                 490                 495

Lys Lys Asn Lys Asn Ser Ile Asn Ile Leu Trp Lys Leu Gly Val
```

-continued

```
                  500                 505                 510
Ala Lys Gln Leu Ala Trp Ala Met His Phe Leu Glu Glu Lys Ser
            515                 520                 525
Leu Ile His Gly Asn Val Cys Ala Lys Asn Ile Leu Leu Ile Arg
            530                 535                 540
Glu Glu Asp Arg Arg Thr Gly Asn Pro Phe Ile Lys Leu Ser Asp
            545                 550                 555
Pro Gly Ile Ser Ile Thr Val Leu Pro Lys Asp Ile Ser Ser Cys
            560                 565                 570
Cys Phe Gln Val Leu Gln Glu Arg Ile Pro Trp Val Pro Pro Glu
            575                 580                 585
Cys Ile Glu Asn Pro Lys Asn Leu Thr Leu Ala Thr Asp Lys Trp
            590                 595                 600
Ser Phe Gly Thr Thr Leu Trp Glu Ile Cys Ser Gly Gly Asp Lys
            605                 610                 615
Pro Leu Ser Ala Leu Asp Ser Gln Arg Lys Leu Gln Phe Tyr Glu
            620                 625                 630
Asp Lys His Gln Leu Pro Ala Pro Lys Trp Thr Glu Leu Ala Asn
            635                 640                 645
Leu Ile Asn Asn Cys Met Asp Tyr Glu Pro Asp Phe Arg Pro Ala
            650                 655                 660
Phe Arg Ala Val Ile Arg Asp Leu Asn Ser Leu Phe Thr Pro Asp
            665                 670                 675
Tyr Glu Leu Leu Thr Glu Asn Asp Met Leu Pro Asn Met Arg Ile
            680                 685                 690
Gly Ala Leu Gly Phe Ser Gly Ala Phe Glu Asp Arg Asp Pro Thr
            695                 700                 705
Gln Phe Glu Glu Arg His Leu Lys Phe Leu Gln Gln Leu Gly Lys
            710                 715                 720
Gly Asn Phe Gly Ser Val Glu Met Cys Arg Tyr Asp Pro Leu Gln
            725                 730                 735
Asp Asn Thr Gly Glu Val Val Ala Val Lys Lys Leu Gln His Ser
            740                 745                 750
Thr Glu Glu His Leu Arg Asp Phe Glu Arg Glu Ile Glu Ile Leu
            755                 760                 765
Lys Ser Leu Gln His Asp Asn Ile Val Lys Tyr Lys Gly Val Cys
            770                 775                 780
Tyr Ser Ala Gly Arg Arg Asn Leu Arg Leu Ile Met Glu Tyr Leu
            785                 790                 795
Pro Tyr Gly Ser Leu Arg Asp Tyr Leu Gln Lys His Lys Glu Arg
            800                 805                 810
Ile Asp His Lys Lys Leu Leu Gln Tyr Thr Ser Gln Ile Cys Lys
            815                 820                 825
Gly Met Glu Tyr Leu Gly Thr Lys Arg Tyr Ile His Arg Asp Leu
            830                 835                 840
Ala Thr Arg Asn Ile Leu Val Glu Asn Glu Asn Arg Val Lys Ile
            845                 850                 855
Gly Asp Phe Gly Leu Thr Lys Val Leu Pro Gln Asp Lys Glu Tyr
            860                 865                 870
Tyr Lys Val Lys Glu Pro Gly Glu Ser Pro Ile Phe Trp Tyr Ala
            875                 880                 885
Pro Glu Ser Leu Thr Glu Ser Lys Phe Ser Val Ala Ser Asp Val
            890                 895                 900
```

Trp Ser Phe Gly Val Val Leu Tyr Glu Leu Phe Thr Tyr Ile Glu
                905                 910                 915

Lys Ser Lys Ser Pro Val Glu Phe Met Arg Met Ile Gly Asn
                920                 925                 930

Asp Lys Gln Gly Gln Met Ile Val Phe His Leu Ile Glu Leu Leu
                935                 940                 945

Lys Ser Asn Gly Arg Leu Pro Arg Pro Glu Gly Cys Pro Asp Glu
                950                 955                 960

Ile Tyr Val Ile Met Thr Glu Cys Trp Asn Asn
                965                 970

(2) INFORMATION FOR SEQ ID NO:20:

(i) SEQUENCE CHARACTERISTICS:
        (A) LENGTH: 1184 amino acids
        (B) TYPE: amino acid
        (D) TOPOLOGY: linear (xi) SEQUENCE DESCRIPTION: SEQ ID NO:20:

Met Pro Leu Arg His Trp Gly Met Ala Arg Gly Ser Lys Pro Val
                  5                  10                  15

Gly Asp Gly Ala Gln Pro Met Ala Ala Met Gly Gly Leu Lys Val
                 20                  25                  30

Leu Leu His Trp Ala Gly Pro Gly Gly Gly Glu Pro Trp Val Thr
                 35                  40                  45

Phe Ser Glu Ser Ser Leu Ile Ala Glu Glu Val Cys Ile His Ile
                 50                  55                  60

Ala His Lys Val Gly Ile Thr Pro Pro Cys Phe Asn Leu Phe Ala
                 65                  70                  75

Leu Phe Asp Ala Gln Ala Gln Val Trp Leu Pro Pro Asn His Ile
                 80                  85                  90

Leu Glu Ile Pro Arg Asp Ala Ser Leu Met Leu Tyr Phe Arg Ile
                 95                 100                 105

Arg Phe Tyr Phe Arg Asn Trp His Gly Met Asn Pro Arg Glu Pro
                110                 115                 120

Ala Gly Tyr Arg Cys Gly Pro Pro Gly Thr Glu Ala Ser Ser Asp
                125                 130                 135

Gln Thr Ala Gln Gly Met Gln Leu Leu Asp Pro Ala Ser Phe Glu
                140                 145                 150

Tyr Leu Phe Glu Gln Gly Lys His Glu Phe Glu Asn Asp Val Ala
                155                 160                 165

Ser Leu Trp Glu Leu Ser Thr Glu Glu Ile His His Phe Lys
                170                 175                 180

Asn Glu Ser Leu Gly Met Ala Phe Leu His Leu Cys His Leu Ala
                185                 190                 195

Leu Arg His Gly Ile Pro Leu Glu Glu Val Ala Lys Lys Thr Ser
                200                 205                 210

Phe Lys Asp Cys Ile Pro Arg Ser Phe Arg Arg His Ile Arg Gln
                215                 220                 225

His Ser Ala Leu Thr Arg Leu Arg Leu Arg Asn Val Phe Arg Arg
                230                 235                 240

Phe Leu Arg Asp Phe Gln Pro Gly Arg Leu Ser Gln Gln Met Val
                245                 250                 255

Met Val Lys Tyr Leu Ala Thr Leu Glu Arg Leu Ala Pro Arg Phe
                260                 265                 270

Gly Thr Glu Arg Val Pro Val Cys His Leu Arg Leu Leu Ala Gln

```
                      275                 280                 285
Ala Glu Gly Glu Pro Cys Tyr Ile Arg Asp Ser Gly Val Ala Pro
                290                 295                 300
Thr Asp Pro Gly Pro Glu Ser Ala Ala Gly Pro Pro Thr His Glu
            305                 310                 315
Val Leu Val Thr Gly Thr Gly Gly Ile Gln Trp Trp Pro Val Glu
        320                 325                 330
Glu Glu Val Asn Lys Glu Glu Gly Ser Ser Gly Ser Ser Ala Arg
    335                 340                 345
Asn Pro Gln Ala Ser Leu Phe Gly Lys Lys Ala Lys Ala His Lys
350                 355                 360
Ala Phe Gly Gln Pro Ala Asp Arg Pro Arg Glu Pro Leu Trp Ala
        365                 370                 375
Tyr Phe Cys Asp Ile Thr His Val Val Leu Lys Glu His Cys Val
            380                 385                 390
Ser Ile His Arg Gln Asp Asn Lys Cys Leu Glu Leu Ser Leu Pro
                395                 400                 405
Ser Arg Ala Ala Ala Leu Ser Phe Glu Ser Leu Val Asp Gly Tyr
                    410                 415                 420
Phe Arg Leu Thr Ala Asp Ser Ser His Tyr Leu Cys His Glu Val
                        425                 430                 435
Ala Pro Pro Arg Leu Val Met Ser Ile Arg Asp Gly Ile His Gly
                            440                 445                 450
Pro Leu Leu Glu Pro Phe Val Gln Gln Ala Lys Leu Arg Pro Leu
                                455                 460                 465
Glu Asp Gly Leu Tyr Leu Ile His Trp Ser Thr Ser His Pro Tyr
                                    470                 475                 480
Arg Leu Ile Leu Thr Val Ala Gln Arg Ser Gln Ala Pro Asp Gly
                                        485                 490                 495
Met Gln Ser Leu Arg Leu Arg Lys Phe Pro Ile Glu Gln Gln Asp
                                            500                 505                 510
Gly Ala Phe Val Leu Glu Gly Trp Gly Arg Ser Phe Pro Ser Val
                                                515                 520                 525
Arg Glu Leu Gly Ala Ala Leu Gln Gly Cys Leu Leu Arg Ala Gly
                                                    530                 535                 540
Asp Asp Cys Phe Ser Leu Arg Arg Cys Cys Leu Pro Gln Pro Gly
                                                        545                 550                 555
Glu Thr Ser Asn Leu Ile Ile Met Arg Gly Ala Arg Ala Ser Pro
                                                            560                 565                 570
Arg Thr Leu Asn Leu Ser Gln Leu Ser Phe His Arg Val Asp Gln
                                                                575                 580                 585
Lys Glu Ile Thr Gln Leu Ser His Leu Gly Gln Gly Thr Arg Thr
                                                                    590                 595                 600
Asn Val Tyr Glu Gly Arg Leu Arg Val Glu Gly Ser Gly Asp Pro
                                                                        605                 610                 615
Glu Glu Gly Lys Met Asp Asp Glu Asp Pro Leu Val Pro Gly Arg
                                                                            620                 625                 630
Asp Arg Gly Gln Glu Leu Arg Val Val Leu Lys Val Leu Asp Pro
                                                                                635                 640                 645
Ser His His Asp Ile Ala Leu Ala Phe Tyr Glu Thr Ala Ser Leu
                                                                                    650                 655                 660
Met Ser Gln Val Ser His Thr His Leu Ala Phe Val His Gly Val
                                                                                        665                 670                 675
```

```
Cys Val Arg Gly Pro Glu Asn Ser Met Val Thr Glu Tyr Val Glu
            680                 685                 690

His Gly Pro Leu Asp Val Trp Leu Arg Glu Arg Gly His Val
            695                 700                 705

Pro Met Ala Trp Lys Met Val Val Ala Gln Gln Leu Ala Ser Ala
            710                 715                 720

Leu Ser Tyr Leu Glu Asn Lys Asn Leu Val His Gly Asn Val Cys
            725                 730                 735

Gly Arg Asn Ile Leu Leu Ala Arg Leu Gly Leu Ala Glu Gly Thr
            740                 745                 750

Ser Pro Phe Ile Lys Leu Ser Asp Pro Gly Cys Gly Leu Gly Ala
            755                 760                 765

Leu Ser Arg Glu Glu Arg Val Glu Arg Ile Pro Trp Leu Ala Pro
            770                 775                 780

Glu Cys Leu Pro Gly Gly Ala Asn Ser Leu Ser Thr Ala Met Asp
            785                 790                 795

Lys Trp Gly Phe Gly Ala Thr Leu Leu Glu Ile Cys Phe Asp Gly
            800                 805                 810

Glu Ala Pro Leu Gln Ser Arg Ser Pro Ser Glu Lys Glu His Phe
            815                 820                 825

Tyr Gln Arg Gln His Arg Leu Pro Glu Pro Ser Cys Pro Gln Leu
            830                 835                 840

Ala Thr Leu Thr Ser Gln Cys Leu Thr Tyr Glu Pro Thr Gln Arg
            845                 850                 855

Pro Ser Phe Ala Thr Ile Leu Arg Asp Leu Thr Arg Val Gln Pro
            860                 865                 870

His Asn Leu Ala Asp Val Leu Thr Val Asn Arg Asp Ser Pro Ala
            875                 880                 885

Val Gly Pro Thr Thr Phe His Lys Arg Tyr Leu Lys Lys Ile Arg
            890                 895                 900

Asp Leu Gly Glu Gly His Phe Gly Lys Val Ser Leu Tyr Cys Tyr
            905                 910                 915

Asp Pro Thr Asn Asp Gly Thr Gly Glu Met Val Ala Val Lys Ala
            920                 925                 930

Leu Lys Ala Asp Cys Gly Pro Gln His Arg Ser Gly Trp Lys Gln
            935                 940                 945

Glu Ile Asp Ile Leu Arg Thr Leu Tyr His Glu His Ile Ile Lys
            950                 955                 960

Tyr Lys Gly Cys Cys Glu Asp Gln Gly Glu Lys Ser Leu Val Met
            965                 970                 975

Glu Tyr Val Pro Leu Gly Ser Leu Arg Asp Tyr Leu Pro Arg His
            980                 985                 990

Ser Ile Gly Leu Ala Gln Leu Leu Leu Phe Ala Gln Gln Ile Cys
            995                 1000                1005

Glu Gly Met Ala Tyr Leu His Ala His Asp Tyr Ile His Arg Asp
            1010                1015                1020

Leu Ala Ala Arg Asn Val Leu Leu Asp Asn Asp Arg Leu Val Lys
            1025                1030                1035

Ile Gly Asp Phe Gly Leu Ala Lys Ala Val Pro Glu Gly His Glu
            1040                1045                1050

Tyr Tyr Arg Val Arg Glu Asp Gly Asp Ser Pro Val Phe Trp Tyr
            1055                1060                1065

Ala Pro Glu Cys Leu Lys Glu Tyr Asn Phe Tyr Tyr Ala Ser Asp
            1070                1075                1080
```

```
Val Trp Ser Phe Gly Val Thr Leu Tyr Glu Leu Leu Thr His Cys
            1085                1090                1095

Asp Ser Ser Gln Ser Pro Pro Thr Lys Phe Leu Glu Leu Ile Gly
            1100                1105                1110

Ile Ala Gln Gly Gln Met Thr Val Leu Arg Leu Thr Glu Leu Leu
            1115                1120                1125

Glu Arg Gly Glu Arg Leu Pro Arg Pro Asp Lys Cys Pro Cys Glu
            1130                1135                1140

Val Tyr His Leu Met Lys Asn Cys Trp Glu Thr Glu Ala Ser Phe
            1145                1150                1155

Arg Pro Thr Phe Glu Asn Ser Ile Pro Ile Leu Lys Thr Val His
            1160                1165                1170

Glu Lys Tyr Gln Gly Gln Ala Pro Ser Val Ser Ser Val Cys
            1175                1180
```

(2) INFORMATION FOR SEQ ID NO:21:

(i) SEQUENCE CHARACTERISTICS:
        (A) LENGTH: 92 amino acids
        (B) TYPE: amino acid
        (D) TOPOLOGY: linear (xi) SEQUENCE DESCRIPTION: SEQ ID NO:21:

```
Trp Tyr His Gly Lys Leu Asp Arg Thr Ile Ala Glu Glu Arg Leu
                5                  10                  15

Arg Gln Ala Gly Lys Ser Gly Ser Tyr Leu Ile Arg Glu Ser Asp
               20                  25                  30

Arg Arg Pro Gly Ser Phe Val Leu Ser Phe Leu Ser Gln Thr Asn
               35                  40                  45

Val Val Asn His Phe Arg Ile Ile Ala Met Cys Gly Asp Tyr Tyr
               50                  55                  60

Ile Gly Gly Arg Arg Phe Ser Ser Leu Ser Asp Leu Ile Gly Tyr
               65                  70                  75

Tyr Ser His Val Ser Cys Leu Leu Lys Gly Glu Lys Leu Leu Tyr
               80                  85                  90

Pro Val
```

(2) INFORMATION FOR SEQ ID NO:22:

(i) SEQUENCE CHARACTERISTICS:
        (A) LENGTH: 91 amino acids
        (B) TYPE: amino acid
        (D) TOPOLOGY: linear (xi) SEQUENCE DESCRIPTION: SEQ ID NO:22:

```
Trp Phe His Gly Lys Ile Ser Lys Gln Glu Ala Tyr Asn Leu Leu
                5                  10                  15

Met Thr Val Gly Gln Ala Cys Ser Phe Leu Val Arg Pro Ser Asp
               20                  25                  30

Asn Thr Pro Gly Asp Tyr Ser Leu Tyr Phe Arg Thr Ser Glu Asn
               35                  40                  45

Ile Gln Arg Phe Lys Ile Cys Pro Thr Pro Asn Asn Gln Phe Met
               50                  55                  60

Met Gly Gly Arg Tyr Tyr Asn Ser Ile Gly Asp Ile Ile Asp His
               65                  70                  75

Tyr Arg Lys Glu Gln Ile Val Glu Gly Tyr Tyr Leu Lys Glu Pro
               80                  85                  90
```

Val (2) INFORMATION FOR SEQ ID NO: 23:

(i) SEQUENCE CHARACTERISTICS:
        (A) LENGTH: 89 amino acids
        (B) TYPE: amino acid
        (D) TOPOLOGY: linear (xi) SEQUENCE DESCRIPTION: SEQ ID NO: 23:

```
Trp Tyr Trp Gly Arg Leu Ser Arg Gly Asp Ala Val Ser Leu Leu
                5                   10                  15

Gln Gly Gln Arg His Gly Thr Phe Leu Val Arg Asp Ser Gly Ser
                20                  25                  30

Ile Pro Gly Asp Phe Val Leu Ser Val Ser Glu Ser Ser Arg Val
                35                  40                  45

Ser His Tyr Ile Val Asn Ser Leu Gly Pro Ala Gly Gly Arg Arg
                50                  55                  60

Ala Gly Gly Glu Phe Asp Ser Leu Pro Ser Leu Leu Glu Phe Tyr
                65                  70                  75

Lys Ile His Tyr Leu Asp Thr Thr Thr Leu Ile Glu Pro Val
                80                  85
```